(12) United States Patent
Bach et al.

(10) Patent No.: US 9,902,754 B2
(45) Date of Patent: *Feb. 27, 2018

(54) MODIFIED PEPTIDES AS POTENT INHIBITORS OF THE PSD-95/NMDA RECEPTOR INTERACTION

(71) Applicant: University of Copenhagen, Copenhagen (DK)

(72) Inventors: Anders Bach, Valby (DK); Kristian Stromgaard, Roskilde (DK)

(73) Assignee: University of Copenhagen, Copenhagen (DK)

( * ) Notice: Subject to any disclaimer, the term of this patent is extended or adjusted under 35 U.S.C. 154(b) by 26 days.

This patent is subject to a terminal disclaimer.

(21) Appl. No.: 14/971,432

(22) Filed: Dec. 16, 2015

(65) Prior Publication Data
US 2016/0176924 A1 Jun. 23, 2016

Related U.S. Application Data

(63) Continuation of application No. 13/002,638, filed as application No. PCT/EP2009/058752 on Jul. 9, 2009, now Pat. No. 9,241,967.

(60) Provisional application No. 61/107,933, filed on Oct. 23, 2008, provisional application No. 61/079,290, filed on Jul. 9, 2008.

(51) Int. Cl.
| | |
|---|---|
| *C07K 7/06* | (2006.01) |
| *C07K 5/103* | (2006.01) |
| *A61K 38/00* | (2006.01) |
| *A61K 38/07* | (2006.01) |
| *A61K 38/08* | (2006.01) |
| *C07K 5/113* | (2006.01) |
| *C07K 14/705* | (2006.01) |
| *A61K 47/64* | (2017.01) |

(52) U.S. Cl.
CPC .............. *C07K 7/06* (2013.01); *A61K 38/07* (2013.01); *A61K 38/08* (2013.01); *A61K 47/64* (2017.08); *C07K 5/1008* (2013.01); *C07K 5/1013* (2013.01); *C07K 5/1021* (2013.01); *C07K 14/70571* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 2005/0059597 A1 | 3/2005 | Tymianski | |
| 2006/0148711 A1* | 7/2006 | Lu ......................... | C07K 5/081 530/330 |
| 2013/0156704 A1* | 6/2013 | Tymianski ............. | A61K 38/10 424/9.2 |
| 2015/0126460 A1* | 5/2015 | Tymianski ............ | A61K 31/275 514/21.4 |

FOREIGN PATENT DOCUMENTS

| | | |
|---|---|---|
| WO | WO-2003014303 | 2/2003 |
| WO | WO-2008008348 A2 | 1/2008 |

OTHER PUBLICATIONS

Andreasen J., et al., "UCCB01-125, A Dimeric Inhibitor of PSD-95, Reduces Inflammatory Pain Without Disrupting Cognitive or Motor Performance: Comparison with the NMDA Receptor Antagonist MK-801," Neuropharmacology 67:193-200, 2013.
Bach A., et al., "Modified Peptides as Potent Inhibitors of the Postsynaptic Density-95/N-Methyl-$_D$-Aspartate Receptor Interaction," J. Med. Chem, 51:6450-6459, 2008.
Bach A., et al., "Design and Synthesis of Highly Potent and Plasma-Stable Dimeric Inhibitors of the PSD-95-NMDA Receptor Interaction," Angew. Chem. Int. Ed., 48:9685-9689, 2009.
Bach A., et al., "Cell-Permeable and Plasma-Stable Peptidomimetic Inhibitors of the Postsynaptic Density-95/N-Methyl-$_D$-Aspartate Receptor Interaction," J. Med. Chem. 54:1333-1346, 2011.
Bach A., et al., "A High-Affinity, Dimeric Inhibitor of PSD-95 Bivalently Interacts with PDZ1-2 and Protects Against Ischemic Brain Damage," PNAS, 109(9):3317-3322, 2012.
Saro, Dorina, "A Thermodynamic Ligand Binding Study of the Third PDZ Domain (PDZ3) from the Mammalian Neuronal Protein PSD 95," American Chemical Society, May 3, 2007.
Aarts, Michelle, "Treatment of Ischemic Brain Damage by Perturbing NMDA Receptor-PSD-95 Protein Interactions," Science, vol. 298, pp. 846-850, Oct. 25, 2002.
Weinstein, Boris, "Chemistry and Biochemistry of Amino Acids, Peptides, and proteins," Chapter 5, vol. 7, Jan. 1971.
Harris, Milton, "Pegylation A Novel Process for Modifying Pharmacokinetics," Clin Pharmacokinet 2001: 40 (7); 539-551.

(Continued)

*Primary Examiner* — Adam Weidner
(74) *Attorney, Agent, or Firm* — Dinsmore & Shohl LLP

(57) ABSTRACT

The present invention is directed to the provision of small molecule inhibitors of the PSD-95/NMDA receptor interaction, employing an undecapeptide corresponding to the C-terminal of the NMDA as a template for finding lead candidates. A compound (NMDAR/PSD-95 inhibitor) of the invention includes a peptide or peptide analog comprising at least four peptide bonded residues having the sequence YTXV or YSXV, wherein Y is selected from among E, Q, and A, or an analog thereof, and X is selected from among A, Q, D, N, N-Me-A, N-Me-Q, N-Me-D, and N-Me-N or an analog thereof, wherein an amino-terminal residue of the peptide is N-alkylated. Alternatively the compound of the invention comprises a first peptide or peptide analog linked to a second peptide or peptide analog by a linker, where the first and second peptide or peptide analog each comprise at least four peptide bonded residues having the sequence YTXV or YSXV, wherein Y is selected from among E, Q, and A, or an analog thereof, and X is selected from among A, Q, D, N, N-Me-A, N-Me-Q, N-Me-D, and N-Me-N or an analog thereof.

19 Claims, 8 Drawing Sheets

(56) References Cited

OTHER PUBLICATIONS

Egholm, Michael, "PNA hybridizes to complementary oligonucleotides obeying the Watson-Crick hydrogen-bnoding rules," Nature, vol. 365, Oct. 7, 1993; pp. 566-568.
Yang, Lihu, "Sold Phase Synthesis of Fmoc N-Methyl Amino Acids: Application of the Fukuyama Amine Synthesis," Tetrahedron Letters, vol. 38, No. 42, pp. 7307-7310, 1997.
Wen, Wenyu, "Targeting PDZ Domain Proteins for Treating NMDA Receptor-Mediated Excitotoxicity," Current Topics in Medical Chemistry, 2006, 6, 711-721.
Szewczuk, Zbigniew, "Design of a Linker for Trivalent Thrombin Inhibitors: Interaction of the Main Chain of the Linker with Thrombin," Biochemistry 1993, 32, 3396-3404.
Stiffler, Michael A., "PDZ Domain Binding Selectivity is Optimized Across the Mouse Proteome," Science 317, 364 (2007).
Singh, Sanjay K., "LNA (locked nucleic acids): synthesis and high-affinity nucleic acid recognition," Chem. Commun, 1998, pp. 455-456.
Hammond, Ming C., "Strand Peptidomimetics as Potent PDZ Domain Ligands," Chemistry & Biology 13, 1247-1251, Dec. 2006.
Pierce, Michael M., "Isothermal Titration Calorimetry of Protein-Protein Interactions," Methods 19, 213-221 (1999).
Paduch, Marcin, "Bivalent Peptides as Models for Multimeric Targets of PDZ Domains," ChemBioChem 2007,8, 443-452.
Nikolovska-Coleska, Zaneta, "Development and optimization of a binding assay for the XIAP BIR3, domain using fluorescence polarization," Analytical Biochemistry 332 (2004), 261-273.
Niethammer, Martin, Cript, "A Novel Postsynaptic Protein that Binds to the Third PDZ Domain of PSD-95/SAP90," Neuron, vol. 20, 693-707, Apr. 1998.
Long, Jia-Fu, Supramodular structure and synergistic target binding of the N-terminal tandem PDZ domains of PSD-95, J. Mol. Biol. (2003) 327, 203-214.
Lim, Indra Adi, "Selectivity and Promiscuity of the First and Second PDZ Domains of PSD-95 and Synapse-associated Protein 102," The Journal of Biological Chemistry, vol. 277, No. 24, Issue of Jun. 14, 2002, 21697-21711.
Hruby, Victor J., "Designing peptide Receptor Agonists and Antagonists," Nature Reviews, vol. 1, Nov. 2002, pp. 847-858.
Hopfner, Karl-Peter, "Chemical Compensation in Macromolecular Bridge-Binding to Thrombin," Biochemistry 1993, 32, 2947-2953.
Aarts, Michelle M., "Novel treatment of excitotoxicity: targeted distruption of intracellular signaling from glutamate receptors," Biochemical Pharmacology 66 (2003) 877-886.
Herve, Francoise, "CNS Delivery Via Adsorptive Transcytosis," The AAPS Journal (2008).
Harris, Baruch Z., "Role of Electrostatic Interactions in PDZ Domain Ligand Recognition," Biochemistry 2003, 42, 2797-2805.
Gianni, Stefano, "The Kinietics of PDZ Domain-Ligand Interactions and Implications for the Binding Mechanism," The Journal of Biological Chemistry, vol. 280, No. 41, pp. 34805-34812, Oct. 14, 2005.
Fukuyama, Tohru, "2-and 4-Nitrobenzenesulfonamides: Exceptionally Versatile Means for Preparation of Secondary Amines and Protection of Amines," Tetrahedron Letters, vol. 36, No. 36,, pp. 6373-6374, 1995.
Doyle, Declan A., "Crystal Structures of a Complexed and Peptide-Free Membrane Protein-Binding Domain: Molecular Basis of Peptide Recognition by PDZ," Cell, vol. 85, 1067-1076, Jun. 28, 1996.
Cul, Hong, "PDZ Protein Interations Underlying NMDA Receptor-Mediated Excitotoxicity and Neuroprotection by PSD-95 Inhibitors," The Journal of Neuroscience, 27(37):9901-9915, Sep. 12, 2007.
Clemons, Paul A., "Design and discovery of protein dimerizers," Current Opinion in Chemical Biology, 1999, 3:112-115.
Chi, Celestine N., "A conserved folding mechanism for PDZ domains," FEBS Letters 581 (2007) 1109-1113.
Chi, Celestine N., "Two Conserved Residues Govern the Salt and pH Dependencies of the Binding Reaction of a PDZ Domain," Journal of Biological Chemistry, Dec. 1, 2006, vol. 281, No. 48; pp. 36811-36818.
Demmer, O., "Introduction of Functional Groups into Peptides via N-Alkylation," Organic Letters, 2008, vol. 10, No. 10, 2015-2018.
Veronese et al., Adv Drug Delivery, 54:435-456, 2002.
Seiler, N., Pharmacology and Therapeutics, 107:99-119, 2005.
Hermanson, Bioconjugate Techniques, 2nd Edition, Elsevier Inc., May 2, 2008, p. 363 and Chapter 18.
Polyethylene Glycol (PEG) and Pegylation of Proteins, Thermo Fisher, product sheet (online Sep. 20, 2008), Retrieved from: https://web.archive.org/web/20110920034902/http://www.fisersci.com/ecomm/serlet/dmstatic?pagename=404&storeId=10652. Retrieved on Mar. 13, 2015.
ClinicalTrials.gov identifier NCT00728182, first published Aug. 2008.

* cited by examiner

Scheme 1[a]

74: (IESDV)₂PEG12

75: (GE[N-Ethylcyclohexyl]TDV)₂PEG12

- 7: IESDV
- 74: (IESDV)$_2$PEG12
- 76: (IESDV)$_2$PEG8
- 77: (IESDV)$_2$PEG6
- 78: (IESDV)$_2$PEG4
- 79: (IESDV)$_2$PEG2
- 80: (IESDV)$_2$PEG1
- 81: (IESDV)$_2$PEG0

SEQUENCE LISTING

<160> NUMBER OF SEQ ID NOS: 26

<210> SEQ ID NO 1
<211> LENGTH: 310
<212> TYPE: DNA
<213> ORGANISM: Homo sapiens
<220> FEATURE:
<221> NAME/KEY: CDS
<222> LOCATION: (1)..(306)
<223> OTHER INFORMATION: HIS-PDZ1 DNA

<400> SEQUENCE: 1

```
atg cac cac cac cac cac ccg cgc gga tcc atg gaa tac gag gaa atc      48
Met His His His His His Pro Arg Gly Ser Met Glu Tyr Glu Glu Ile
1               5                   10                  15 aca ttg gaa agg ggt aac tca ggt ctg ggc ttc agc atc gca ggt ggc      96
Thr Leu Glu Arg Gly Asn Ser Gly Leu Gly Phe Ser Ile Ala Gly Gly
            20                  25                  30 act gac aac cca cac atc ggt gac gac cca tcc att ttc atc acc aag    144
Thr Asp Asn Pro His Ile Gly Asp Asp Pro Ser Ile Phe Ile Thr Lys
        35                  40                  45 atc att cct ggt ggg gct gcg gcc cag gat ggc cgc ctc agg gtc aac    192
Ile Ile Pro Gly Gly Ala Ala Ala Gln Asp Gly Arg Leu Arg Val Asn
50                  55                  60 gac agc atc ctg ttt gta aat gaa gtg gac gtg cgc gag gtg acc cac    240
Asp Ser Ile Leu Phe Val Asn Glu Val Asp Val Arg Glu Val Thr His
65                  70                  75                  80 tca gcg gcg gtg gaa gcc ctc aaa gag gca ggc tcc atc gtt cgc ctc    288
Ser Ala Ala Val Glu Ala Leu Lys Glu Ala Gly Ser Ile Val Arg Leu
                85                  90                  95 tat gtc atg cgc cgg tga attc                                        310
Tyr Val Met Arg Arg
            100
```

<210> SEQ ID NO 2
<211> LENGTH: 101
<212> TYPE: PRT
<213> ORGANISM: Homo sapiens

<400> SEQUENCE: 2

```
Met His His His His His Pro Arg Gly Ser Met Glu Tyr Glu Glu Ile
1               5                   10                  15

Thr Leu Glu Arg Gly Asn Ser Gly Leu Gly Phe Ser Ile Ala Gly Gly
            20                  25                  30

Thr Asp Asn Pro His Ile Gly Asp Asp Pro Ser Ile Phe Ile Thr Lys
        35                  40                  45

Ile Ile Pro Gly Gly Ala Ala Ala Gln Asp Gly Arg Leu Arg Val Asn
50                  55                  60

Asp Ser Ile Leu Phe Val Asn Glu Val Asp Val Arg Glu Val Thr His
65                  70                  75                  80

Ser Ala Ala Val Glu Ala Leu Lys Glu Ala Gly Ser Ile Val Arg Leu
                85                  90                  95

Tyr Val Met Arg Arg
            100
```

<210> SEQ ID NO 3
<211> LENGTH: 322
<212> TYPE: DNA
<213> ORGANISM: Homo sapiens
<220> FEATURE:
<221> NAME/KEY: CDS
<222> LOCATION: (1)..(318)

<223> OTHER INFORMATION: HIS-PDZ2 DNA

<400> SEQUENCE: 3

```
atg cac cac cac cac cac ccg cgc gga tcc gct gag aag gtc atg gag     48
Met His His His His His Pro Arg Gly Ser Ala Glu Lys Val Met Glu
1               5                   10                  15 atc aag ctc atc aag ggg cct aaa ggt ctt ggc ttc agc atc gca ggg     96
Ile Lys Leu Ile Lys Gly Pro Lys Gly Leu Gly Phe Ser Ile Ala Gly
                20                  25                  30 ggc gta ggg aac cag cac atc cca gga gat aat agc atc tat gta aca    144
Gly Val Gly Asn Gln His Ile Pro Gly Asp Asn Ser Ile Tyr Val Thr
            35                  40                  45 aag atc atc gaa ggg ggt gct gcc cac aag gat ggg agg ttg cag att    192
Lys Ile Ile Glu Gly Gly Ala Ala His Lys Asp Gly Arg Leu Gln Ile
        50                  55                  60 gga gac aag atc ctg gcg gtc aac agt gtg ggg cta gag gac gtc atg    240
Gly Asp Lys Ile Leu Ala Val Asn Ser Val Gly Leu Glu Asp Val Met
65                  70                  75                  80 cat gaa gat gct gtg gca gcc ctg aag aac acg tat gat gtt gtc tac    288
His Glu Asp Ala Val Ala Ala Leu Lys Asn Thr Tyr Asp Val Val Tyr
                85                  90                  95 cta aag gtg gcc aag ccc agc aat gcc tga attc                       322
Leu Lys Val Ala Lys Pro Ser Asn Ala
                100                 105
```

<210> SEQ ID NO 4
<211> LENGTH: 105
<212> TYPE: PRT
<213> ORGANISM: Homo sapiens

<400> SEQUENCE: 4

```
Met His His His His His Pro Arg Gly Ser Ala Glu Lys Val Met Glu
1               5                   10                  15

Ile Lys Leu Ile Lys Gly Pro Lys Gly Leu Gly Phe Ser Ile Ala Gly
                20                  25                  30

Gly Val Gly Asn Gln His Ile Pro Gly Asp Asn Ser Ile Tyr Val Thr
            35                  40                  45

Lys Ile Ile Glu Gly Gly Ala Ala His Lys Asp Gly Arg Leu Gln Ile
        50                  55                  60

Gly Asp Lys Ile Leu Ala Val Asn Ser Val Gly Leu Glu Asp Val Met
65                  70                  75                  80

His Glu Asp Ala Val Ala Ala Leu Lys Asn Thr Tyr Asp Val Val Tyr
                85                  90                  95

Leu Lys Val Ala Lys Pro Ser Asn Ala
                100                 105
```

<210> SEQ ID NO 5
<211> LENGTH: 312
<212> TYPE: DNA
<213> ORGANISM: Homo sapiens
<220> FEATURE:
<221> NAME/KEY: CDS
<222> LOCATION: (1)..(312)
<223> OTHER INFORMATION: HIS-PDZ3

<400> SEQUENCE: 5

```
atg cac cac cac cac cac ccg cgc gga tcc cga gaa ccg agg cga att     48
Met His His His His His Pro Arg Gly Ser Arg Glu Pro Arg Arg Ile
1               5                   10                  15 gtg atc cac cgg ggc tcc acg ggc ctg ggc ttc aac atc gtg ggt ggc     96
Val Ile His Arg Gly Ser Thr Gly Leu Gly Phe Asn Ile Val Gly Gly
```

```
                20                  25                  30
gag gac ggt gaa ggc atc ttc atc tcc ttt atc ctg gcc ggg ggc cct       144
Glu Asp Gly Glu Gly Ile Phe Ile Ser Phe Ile Leu Ala Gly Gly Pro
         35                  40                  45 gca gac ctc agt ggg gag ctg cgg aag ggg gac cag atc ctg tcg gtc       192
Ala Asp Leu Ser Gly Glu Leu Arg Lys Gly Asp Gln Ile Leu Ser Val
 50                  55                  60 aac ggt gtg gac ctc cga aat gcc agc cat gag cag gct gcc att gcc       240
Asn Gly Val Asp Leu Arg Asn Ala Ser His Glu Gln Ala Ala Ile Ala
 65                  70                  75                  80 ctg aag aat gcg ggt cag acg gtc acg atc atc gct cag tat aaa cca       288
Leu Lys Asn Ala Gly Gln Thr Val Thr Ile Ile Ala Gln Tyr Lys Pro
                 85                  90                  95 gaa gag tac agc cga ttc gag tga                                       312
Glu Glu Tyr Ser Arg Phe Glu
            100

<210> SEQ ID NO 6
<211> LENGTH: 103
<212> TYPE: PRT
<213> ORGANISM: Homo sapiens

<400> SEQUENCE: 6

Met His His His His His Pro Arg Gly Ser Arg Glu Pro Arg Arg Ile
1               5                   10                  15

Val Ile His Arg Gly Ser Thr Gly Leu Gly Phe Asn Ile Val Gly Gly
                20                  25                  30

Glu Asp Gly Glu Gly Ile Phe Ile Ser Phe Ile Leu Ala Gly Gly Pro
            35                  40                  45

Ala Asp Leu Ser Gly Glu Leu Arg Lys Gly Asp Gln Ile Leu Ser Val
 50                  55                  60

Asn Gly Val Asp Leu Arg Asn Ala Ser His Glu Gln Ala Ala Ile Ala
 65                  70                  75                  80

Leu Lys Asn Ala Gly Gln Thr Val Thr Ile Ile Ala Gln Tyr Lys Pro
                 85                  90                  95

Glu Glu Tyr Ser Arg Phe Glu
            100

<210> SEQ ID NO 7
<211> LENGTH: 605
<212> TYPE: DNA
<213> ORGANISM: Homo sapiens
<220> FEATURE:
<221> NAME/KEY: CDS
<222> LOCATION: (1)..(600)
<223> OTHER INFORMATION: HIS-PDZ1-2 DNA

<400> SEQUENCE: 7 atg cac cac cac cac cac ccg cgc gga tcc atg gaa tac gag gaa atc        48
Met His His His His His Pro Arg Gly Ser Met Glu Tyr Glu Glu Ile
1               5                   10                  15 aca ttg gaa agg ggt aac tca ggt ctg ggc ttc agc atc gca ggt ggc        96
Thr Leu Glu Arg Gly Asn Ser Gly Leu Gly Phe Ser Ile Ala Gly Gly
                20                  25                  30 act gac aac cca cac atc ggt gac gac cca tcc att ttc atc acc aag       144
Thr Asp Asn Pro His Ile Gly Asp Asp Pro Ser Ile Phe Ile Thr Lys
             35                  40                  45 atc att cct ggt ggg gct gcg gcc cag gat ggc cgc ctc agg gtc aac       192
Ile Ile Pro Gly Gly Ala Ala Ala Gln Asp Gly Arg Leu Arg Val Asn
 50                  55                  60
```

```
gac agc atc ctg ttt gta aat gaa gtg gac gtg cgc gag gtg acc cac      240
Asp Ser Ile Leu Phe Val Asn Glu Val Asp Val Arg Glu Val Thr His
65                  70                  75                  80 tca gcg gcg gtg gaa gcc ctc aaa gag gca ggc tcc atc gtt cgc ctc      288
Ser Ala Ala Val Glu Ala Leu Lys Glu Ala Gly Ser Ile Val Arg Leu
                85                  90                  95 tat gtc atg cgc cgg aag ccc ccg gct gag aag gtc atg gag atc aag      336
Tyr Val Met Arg Arg Lys Pro Pro Ala Glu Lys Val Met Glu Ile Lys
            100                 105                 110 ctc atc aag ggg cct aaa ggt ctt ggc ttc agc atc gca ggg ggc gta      384
Leu Ile Lys Gly Pro Lys Gly Leu Gly Phe Ser Ile Ala Gly Gly Val
        115                 120                 125 ggg aac cag cac atc cca gga gat aat agc atc tat gta aca aag atc      432
Gly Asn Gln His Ile Pro Gly Asp Asn Ser Ile Tyr Val Thr Lys Ile
    130                 135                 140 atc gaa ggg ggt gct gcc cac aag gat ggg agg ttg cag att gga gac      480
Ile Glu Gly Gly Ala Ala His Lys Asp Gly Arg Leu Gln Ile Gly Asp
145                 150                 155                 160 aag atc ctg gcg gtc aac agt gtg ggg cta gag gac gtc atg cat gaa      528
Lys Ile Leu Ala Val Asn Ser Val Gly Leu Glu Asp Val Met His Glu
                165                 170                 175 gat gct gtg gca gcc ctg aag aac acg tat gat gtt gtc tac cta aag      576
Asp Ala Val Ala Ala Leu Lys Asn Thr Tyr Asp Val Val Tyr Leu Lys
            180                 185                 190 gtg gcc aag ccc agc aat gcc tga attcg                                605
Val Ala Lys Pro Ser Asn Ala
        195

<210> SEQ ID NO 8
<211> LENGTH: 199
<212> TYPE: PRT
<213> ORGANISM: Homo sapiens

<400> SEQUENCE: 8

Met His His His His His Pro Arg Gly Ser Met Glu Tyr Glu Glu Ile
1               5                   10                  15

Thr Leu Glu Arg Gly Asn Ser Gly Leu Gly Phe Ser Ile Ala Gly Gly
            20                  25                  30

Thr Asp Asn Pro His Ile Gly Asp Asp Pro Ser Ile Phe Ile Thr Lys
        35                  40                  45

Ile Ile Pro Gly Gly Ala Ala Gln Asp Gly Arg Leu Arg Val Asn
    50                  55                  60

Asp Ser Ile Leu Phe Val Asn Glu Val Asp Val Arg Glu Val Thr His
65                  70                  75                  80

Ser Ala Ala Val Glu Ala Leu Lys Glu Ala Gly Ser Ile Val Arg Leu
                85                  90                  95

Tyr Val Met Arg Arg Lys Pro Pro Ala Glu Lys Val Met Glu Ile Lys
            100                 105                 110

Leu Ile Lys Gly Pro Lys Gly Leu Gly Phe Ser Ile Ala Gly Gly Val
        115                 120                 125

Gly Asn Gln His Ile Pro Gly Asp Asn Ser Ile Tyr Val Thr Lys Ile
    130                 135                 140

Ile Glu Gly Gly Ala Ala His Lys Asp Gly Arg Leu Gln Ile Gly Asp
145                 150                 155                 160

Lys Ile Leu Ala Val Asn Ser Val Gly Leu Glu Asp Val Met His Glu
                165                 170                 175

Asp Ala Val Ala Ala Leu Lys Asn Thr Tyr Asp Val Val Tyr Leu Lys
            180                 185                 190
```

Val Ala Lys Pro Ser Asn Ala
        195

<210> SEQ ID NO 9
<211> LENGTH: 822
<212> TYPE: DNA
<213> ORGANISM: Homo sapiens
<220> FEATURE:
<221> NAME/KEY: CDS
<222> LOCATION: (1)..(822)
<223> OTHER INFORMATION: GFP-NR2B DNA

<400> SEQUENCE: 9

```
atg gtg agc aag ggc gag gag ctg ttc acc ggg gtg gtg ccc atc ctg        48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc        96
Val Glu Leu Asp Gly Asp Val Asn Gly His Lys Phe Ser Val Ser Gly
                20                  25                  30 gag ggc gag ggc gat gcc acc tac ggc aag ctg acc ctg aag ttc atc       144
Glu Gly Glu Gly Asp Ala Thr Tyr Gly Lys Leu Thr Leu Lys Phe Ile
            35                  40                  45 tgc acc acc ggc aag ctg ccc gtg ccc tgg ccc acc ctc gtg acc acc       192
Cys Thr Thr Gly Lys Leu Pro Val Pro Trp Pro Thr Leu Val Thr Thr
        50                  55                  60 ctg agc tac ggc gtg cag tgc ttc agc cgc tac ccc gac cac atg aag       240
Leu Ser Tyr Gly Val Gln Cys Phe Ser Arg Tyr Pro Asp His Met Lys
65                  70                  75                  80 cag cac gac ttc ttc aag tcc gcc atg ccc gaa ggc tac gtc cag gag       288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag       336
Arg Thr Ile Phe Phe Lys Asp Asp Gly Asn Tyr Lys Thr Arg Ala Glu
                100                 105                 110 gtg aag ttc gag ggc gac acc ctg gtg aac cgc atc gag ctg aag ggc       384
Val Lys Phe Glu Gly Asp Thr Leu Val Asn Arg Ile Glu Leu Lys Gly
            115                 120                 125 atc gac ttc aag gag gac ggc aac atc ctg ggg cac aag ctg gag tac       432
Ile Asp Phe Lys Glu Asp Gly Asn Ile Leu Gly His Lys Leu Glu Tyr
        130                 135                 140 aac tac aac agc cac aac gtc tat atc atg gcc gac aag cag aag aac       480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc       528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc       576
Val Gln Leu Ala Asp His Tyr Gln Gln Asn Thr Pro Ile Gly Asp Gly
                180                 185                 190 ccc gtg ctg ctg ccc gac aac cac tac ctg agc acc cag tcc gcc ctg       624
Pro Val Leu Leu Pro Asp Asn His Tyr Leu Ser Thr Gln Ser Ala Leu
            195                 200                 205 agc aaa gac ccc aac gag aag cgc gat cac atg gtc ctg ctg gag ttc       672
Ser Lys Asp Pro Asn Glu Lys Arg Asp His Met Val Leu Leu Glu Phe
        210                 215                 220 gtg acc gcc gcc ggg atc act ctc ggc atg gac gag ctg tac aag tcc       720
Val Thr Ala Ala Gly Ile Thr Leu Gly Met Asp Glu Leu Tyr Lys Ser
225                 230                 235                 240 gga ctc aga tct ggc gag ctc tcg aga att ctc acg cgt ctg cag gat       768
Gly Leu Arg Ser Gly Glu Leu Ser Arg Ile Leu Thr Arg Leu Gln Asp
                245                 250                 255
```

-continued

```
atc aag ctt gga cat gtt tat gag aaa ctt tct agt att gag tct gat      816
Ile Lys Leu Gly His Val Tyr Glu Lys Leu Ser Ser Ile Glu Ser Asp
            260                 265                 270 gtc tga                                                              822
Val
```

```
<210> SEQ ID NO 10
<211> LENGTH: 273
<212> TYPE: PRT
<213> ORGANISM: Homo sapiens

<400> SEQUENCE: 10
```

| | | | | | | | | | | | | | | | |
|---|---|---|---|---|---|---|---|---|---|---|---|---|---|---|---|
| Met | Val | Ser | Lys | Gly | Glu | Glu | Leu | Phe | Thr | Gly | Val | Val | Pro | Ile | Leu |
| 1 | | | | 5 | | | | | 10 | | | | | 15 | |
| Val | Glu | Leu | Asp | Gly | Asp | Val | Asn | Gly | His | Lys | Phe | Ser | Val | Ser | Gly |
| | | | 20 | | | | | 25 | | | | | 30 | | |
| Glu | Gly | Glu | Gly | Asp | Ala | Thr | Tyr | Gly | Lys | Leu | Thr | Leu | Lys | Phe | Ile |
| | | | 35 | | | | | 40 | | | | | 45 | | |
| Cys | Thr | Thr | Gly | Lys | Leu | Pro | Val | Pro | Trp | Pro | Thr | Leu | Val | Thr | Thr |
| | 50 | | | | | 55 | | | | | 60 | | | | |
| Leu | Ser | Tyr | Gly | Val | Gln | Cys | Phe | Ser | Arg | Tyr | Pro | Asp | His | Met | Lys |
| 65 | | | | | 70 | | | | | 75 | | | | | 80 |
| Gln | His | Asp | Phe | Phe | Lys | Ser | Ala | Met | Pro | Glu | Gly | Tyr | Val | Gln | Glu |
| | | | | 85 | | | | | 90 | | | | | 95 | |
| Arg | Thr | Ile | Phe | Phe | Lys | Asp | Asp | Gly | Asn | Tyr | Lys | Thr | Arg | Ala | Glu |
| | | | 100 | | | | | 105 | | | | | 110 | | |
| Val | Lys | Phe | Glu | Gly | Asp | Thr | Leu | Val | Asn | Arg | Ile | Glu | Leu | Lys | Gly |
| | | | 115 | | | | | 120 | | | | | 125 | | |
| Ile | Asp | Phe | Lys | Glu | Asp | Gly | Asn | Ile | Leu | Gly | His | Lys | Leu | Glu | Tyr |
| | 130 | | | | | 135 | | | | | 140 | | | | |
| Asn | Tyr | Asn | Ser | His | Asn | Val | Tyr | Ile | Met | Ala | Asp | Lys | Gln | Lys | Asn |
| 145 | | | | | 150 | | | | | 155 | | | | | 160 |
| Gly | Ile | Lys | Val | Asn | Phe | Lys | Ile | Arg | His | Asn | Ile | Glu | Asp | Gly | Ser |
| | | | | 165 | | | | | 170 | | | | | 175 | |
| Val | Gln | Leu | Ala | Asp | His | Tyr | Gln | Gln | Asn | Thr | Pro | Ile | Gly | Asp | Gly |
| | | | 180 | | | | | 185 | | | | | 190 | | |
| Pro | Val | Leu | Leu | Pro | Asp | Asn | His | Tyr | Leu | Ser | Thr | Gln | Ser | Ala | Leu |
| | | | 195 | | | | | 200 | | | | | 205 | | |
| Ser | Lys | Asp | Pro | Asn | Glu | Lys | Arg | Asp | His | Met | Val | Leu | Leu | Glu | Phe |
| | 210 | | | | | 215 | | | | | 220 | | | | |
| Val | Thr | Ala | Ala | Gly | Ile | Thr | Leu | Gly | Met | Asp | Glu | Leu | Tyr | Lys | Ser |
| 225 | | | | | 230 | | | | | 235 | | | | | 240 |
| Gly | Leu | Arg | Ser | Gly | Glu | Leu | Ser | Arg | Ile | Leu | Thr | Arg | Leu | Gln | Asp |
| | | | | 245 | | | | | 250 | | | | | 255 | |
| Ile | Lys | Leu | Gly | His | Val | Tyr | Glu | Lys | Leu | Ser | Ser | Ile | Glu | Ser | Asp |
| | | | 260 | | | | | 265 | | | | | 270 | | |
| Val | | | | | | | | | | | | | | | |

```
<210> SEQ ID NO 11
<211> LENGTH: 822
<212> TYPE: DNA
<213> ORGANISM: Homo sapiens
<220> FEATURE:
<221> NAME/KEY: CDS
<222> LOCATION: (1)..(822)
<223> OTHER INFORMATION: GRF-NR2B AA DNA (mutant)
```

<400> SEQUENCE: 11

| | | | | | | | | | | | | | | | | |
|---|---|---|---|---|---|---|---|---|---|---|---|---|---|---|---|---|
| atg | gtg | agc | aag | ggc | gag | gag | ctg | ttc | acc | ggg | gtg | gtg | ccc | atc | ctg | 48 |
| Met | Val | Ser | Lys | Gly | Glu | Glu | Leu | Phe | Thr | Gly | Val | Val | Pro | Ile | Leu | |
| 1 | | | | 5 | | | | | 10 | | | | | 15 | | |
| gtc | gag | ctg | gac | ggc | gac | gta | aac | ggc | cac | aag | ttc | agc | gtg | tcc | ggc | 96 |
| Val | Glu | Leu | Asp | Gly | Asp | Val | Asn | Gly | His | Lys | Phe | Ser | Val | Ser | Gly | |
| | | | 20 | | | | | 25 | | | | | 30 | | | |
| gag | ggc | gag | ggc | gat | gcc | acc | tac | ggc | aag | ctg | acc | ctg | aag | ttc | atc | 144 |
| Glu | Gly | Glu | Gly | Asp | Ala | Thr | Tyr | Gly | Lys | Leu | Thr | Leu | Lys | Phe | Ile | |
| | | 35 | | | | | 40 | | | | | 45 | | | | |
| tgc | acc | acc | ggc | aag | ctg | ccc | gtg | ccc | tgg | ccc | acc | ctc | gtg | acc | acc | 192 |
| Cys | Thr | Thr | Gly | Lys | Leu | Pro | Val | Pro | Trp | Pro | Thr | Leu | Val | Thr | Thr | |
| 50 | | | | | 55 | | | | | 60 | | | | | | |
| ctg | agc | tac | ggc | gtg | cag | tgc | ttc | agc | cgc | tac | ccc | gac | cac | atg | aag | 240 |
| Leu | Ser | Tyr | Gly | Val | Gln | Cys | Phe | Ser | Arg | Tyr | Pro | Asp | His | Met | Lys | |
| 65 | | | | 70 | | | | | 75 | | | | | 80 | | |
| cag | cac | gac | ttc | ttc | aag | tcc | gcc | atg | ccc | gaa | ggc | tac | gtc | cag | gag | 288 |
| Gln | His | Asp | Phe | Phe | Lys | Ser | Ala | Met | Pro | Glu | Gly | Tyr | Val | Gln | Glu | |
| | | | | 85 | | | | | 90 | | | | | 95 | | |
| cgc | acc | atc | ttc | ttc | aag | gac | gac | ggc | aac | tac | aag | acc | cgc | gcc | gag | 336 |
| Arg | Thr | Ile | Phe | Phe | Lys | Asp | Asp | Gly | Asn | Tyr | Lys | Thr | Arg | Ala | Glu | |
| | | | | 100 | | | | | 105 | | | | | 110 | | |
| gtg | aag | ttc | gag | ggc | gac | acc | ctg | gtg | aac | cgc | atc | gag | ctg | aag | ggc | 384 |
| Val | Lys | Phe | Glu | Gly | Asp | Thr | Leu | Val | Asn | Arg | Ile | Glu | Leu | Lys | Gly | |
| | | | 115 | | | | | 120 | | | | | 125 | | | |
| atc | gac | ttc | aag | gag | gac | ggc | aac | atc | ctg | ggg | cac | aag | ctg | gag | tac | 432 |
| Ile | Asp | Phe | Lys | Glu | Asp | Gly | Asn | Ile | Leu | Gly | His | Lys | Leu | Glu | Tyr | |
| | | 130 | | | | | 135 | | | | | 140 | | | | |
| aac | tac | aac | agc | cac | aac | gtc | tat | atc | atg | gcc | gac | aag | cag | aag | aac | 480 |
| Asn | Tyr | Asn | Ser | His | Asn | Val | Tyr | Ile | Met | Ala | Asp | Lys | Gln | Lys | Asn | |
| 145 | | | | | 150 | | | | | 155 | | | | | 160 | |
| ggc | atc | aag | gtg | aac | ttc | aag | atc | cgc | cac | aac | atc | gag | gac | ggc | agc | 528 |
| Gly | Ile | Lys | Val | Asn | Phe | Lys | Ile | Arg | His | Asn | Ile | Glu | Asp | Gly | Ser | |
| | | | | 165 | | | | | 170 | | | | | 175 | | |
| gtg | cag | ctc | gcc | gac | cac | tac | cag | cag | aac | acc | ccc | atc | ggc | gac | ggc | 576 |
| Val | Gln | Leu | Ala | Asp | His | Tyr | Gln | Gln | Asn | Thr | Pro | Ile | Gly | Asp | Gly | |
| | | | 180 | | | | | 185 | | | | | 190 | | | |
| ccc | gtg | ctg | ctg | ccc | gac | aac | cac | tac | ctg | agc | acc | cag | tcc | gcc | ctg | 624 |
| Pro | Val | Leu | Leu | Pro | Asp | Asn | His | Tyr | Leu | Ser | Thr | Gln | Ser | Ala | Leu | |
| | | 195 | | | | | 200 | | | | | 205 | | | | |
| agc | aaa | gac | ccc | aac | gag | aag | cgc | gat | cac | atg | gtc | ctg | ctg | gag | ttc | 672 |
| Ser | Lys | Asp | Pro | Asn | Glu | Lys | Arg | Asp | His | Met | Val | Leu | Leu | Glu | Phe | |
| 210 | | | | | 215 | | | | | 220 | | | | | | |
| gtg | acc | gcc | gcc | ggg | atc | act | ctc | ggc | atg | gac | gag | ctg | tac | aag | tcc | 720 |
| Val | Thr | Ala | Ala | Gly | Ile | Thr | Leu | Gly | Met | Asp | Glu | Leu | Tyr | Lys | Ser | |
| 225 | | | | | 230 | | | | | 235 | | | | | 240 | |
| gga | ctc | aga | tct | ggc | gag | ctc | tcg | aga | att | ctc | acg | cgt | ctg | cag | gat | 768 |
| Gly | Leu | Arg | Ser | Gly | Glu | Leu | Ser | Arg | Ile | Leu | Thr | Arg | Leu | Gln | Asp | |
| | | | | 245 | | | | | 250 | | | | | 255 | | |
| atc | aag | ctt | gga | cat | gtt | tat | gag | aaa | ctt | tct | agt | att | gag | gct | gat | 816 |
| Ile | Lys | Leu | Gly | His | Val | Tyr | Glu | Lys | Leu | Ser | Ser | Ile | Glu | Ala | Asp | |
| | | | 260 | | | | | 265 | | | | | 270 | | | |
| gcc | tga | | | | | | | | | | | | | | | 822 |
| Ala | | | | | | | | | | | | | | | | |

<210> SEQ ID NO 12
<211> LENGTH: 273
<212> TYPE: PRT
<213> ORGANISM: Homo sapiens

```
<400> SEQUENCE: 12

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65              70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Gly Glu Leu Ser Arg Ile Leu Thr Arg Leu Gln Asp
                245                 250                 255

Ile Lys Leu Gly His Val Tyr Glu Lys Leu Ser Ser Ile Glu Ala Asp
            260                 265                 270

Ala

<210> SEQ ID NO 13
<211> LENGTH: 1074
<212> TYPE: DNA
<213> ORGANISM: Homo sapiens
<220> FEATURE:
<221> NAME/KEY: CDS
<222> LOCATION: (1)..(1074)
<223> OTHER INFORMATION: GFP-PDZ2 DNA

<400> SEQUENCE: 13 atg gtg agc aag ggc gag gag ctg ttc acc ggg gtg gtg ccc atc ctg       48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc       96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc      144
Glu Gly Glu Gly Asp Ala Thr Tyr Gly Lys Leu Thr Leu Lys Phe Ile
        35                  40                  45
```

```
tgc acc acc ggc aag ctg ccc gtg ccc tgg ccc acc ctc gtg acc acc        192
Cys Thr Thr Gly Lys Leu Pro Val Pro Trp Pro Thr Leu Val Thr Thr
 50              55                  60 ctg agc tac ggc gtg cag tgc ttc agc cgc tac ccc gac cac atg aag        240
Leu Ser Tyr Gly Val Gln Cys Phe Ser Arg Tyr Pro Asp His Met Lys
 65              70                  75                  80 cag cac gac ttc ttc aag tcc gcc atg ccc gaa ggc tac gtc cag gag        288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag        336
Arg Thr Ile Phe Phe Lys Asp Asp Gly Asn Tyr Lys Thr Arg Ala Glu
                100                 105                 110 gtg aag ttc gag ggc gac acc ctg gtg aac cgc atc gag ctg aag ggc        384
Val Lys Phe Glu Gly Asp Thr Leu Val Asn Arg Ile Glu Leu Lys Gly
            115                 120                 125 atc gac ttc aag gag gac ggc aac atc ctg ggg cac aag ctg gag tac        432
Ile Asp Phe Lys Glu Asp Gly Asn Ile Leu Gly His Lys Leu Glu Tyr
130                 135                 140 aac tac aac agc cac aac gtc tat atc atg gcc gac aag cag aag aac        480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc        528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc        576
Val Gln Leu Ala Asp His Tyr Gln Gln Asn Thr Pro Ile Gly Asp Gly
                180                 185                 190 ccc gtg ctg ctg ccc gac aac cac tac ctg agc acc cag tcc gcc ctg        624
Pro Val Leu Leu Pro Asp Asn His Tyr Leu Ser Thr Gln Ser Ala Leu
            195                 200                 205 agc aaa gac ccc aac gag aag cgc gat cac atg gtc ctg ctg gag ttc        672
Ser Lys Asp Pro Asn Glu Lys Arg Asp His Met Val Leu Leu Glu Phe
210                 215                 220 gtg acc gcc gcc ggg atc act ctc ggc atg gac gag ctg tac aag tcc        720
Val Thr Ala Ala Gly Ile Thr Leu Gly Met Asp Glu Leu Tyr Lys Ser
225                 230                 235                 240 gga ctc aga tct ggc gag ctc tcg aga att ctc acg cgt ctg cag gat        768
Gly Leu Arg Ser Gly Glu Leu Ser Arg Ile Leu Thr Arg Leu Gln Asp
                245                 250                 255 atc aag ctt atg cgc cgg aag ccc ccg gct gag aag gtc atg gag atc        816
Ile Lys Leu Met Arg Arg Lys Pro Pro Ala Glu Lys Val Met Glu Ile
                260                 265                 270 aag ctc atc aag ggg cct aaa ggt ctt ggc ttc agc atc gca ggg ggc        864
Lys Leu Ile Lys Gly Pro Lys Gly Leu Gly Phe Ser Ile Ala Gly Gly
            275                 280                 285 gta ggg aac cag cac atc cca gga gat aat agc atc tat gta aca aag        912
Val Gly Asn Gln His Ile Pro Gly Asp Asn Ser Ile Tyr Val Thr Lys
            290                 295                 300 atc atc gaa ggg ggt gct gcc cac aag gat ggg agg ttg cag att gga        960
Ile Ile Glu Gly Gly Ala Ala His Lys Asp Gly Arg Leu Gln Ile Gly
305                 310                 315                 320 gac aag atc ctg gcg gtc aac agt gtg ggg cta gag gac gtc atg cat       1008
Asp Lys Ile Leu Ala Val Asn Ser Val Gly Leu Glu Asp Val Met His
                325                 330                 335 gaa gat gct gtg gca gcc ctg aag aac acg tat gat gtt gtc tac cta       1056
Glu Asp Ala Val Ala Ala Leu Lys Asn Thr Tyr Asp Val Val Tyr Leu
                340                 345                 350 aag gtg gcc aag ccc tag                                                1074
Lys Val Ala Lys Pro
            355
```

```
<210> SEQ ID NO 14
<211> LENGTH: 357
<212> TYPE: PRT
<213> ORGANISM: Homo sapiens

<400> SEQUENCE: 14
```

| | | | | | | | | | | | | | | |
|---|---|---|---|---|---|---|---|---|---|---|---|---|---|---|
|Met|Val|Ser|Lys|Gly|Glu|Glu|Leu|Phe|Thr|Gly|Val|Pro|Ile|Leu|
|1| | | |5| | | | |10| | | | |15|
|Val|Glu|Leu|Asp|Gly|Asp|Val|Asn|Gly|His|Lys|Phe|Ser|Val|Ser|Gly|
| | | |20| | | | |25| | | | |30| |
|Glu|Gly|Glu|Gly|Asp|Ala|Thr|Tyr|Gly|Lys|Leu|Thr|Leu|Lys|Phe|Ile|
| | | |35| | | | |40| | | | |45| |
|Cys|Thr|Thr|Gly|Lys|Leu|Pro|Val|Pro|Trp|Pro|Thr|Leu|Val|Thr|Thr|
|50| | | | |55| | | | |60| | | | |
|Leu|Ser|Tyr|Gly|Val|Gln|Cys|Phe|Ser|Arg|Tyr|Pro|Asp|His|Met|Lys|
|65| | | | |70| | | | |75| | | | |80|
|Gln|His|Asp|Phe|Phe|Lys|Ser|Ala|Met|Pro|Glu|Gly|Tyr|Val|Gln|Glu|
| | | | |85| | | | |90| | | | |95| |
|Arg|Thr|Ile|Phe|Phe|Lys|Asp|Asp|Gly|Asn|Tyr|Lys|Thr|Arg|Ala|Glu|
| | | | |100| | | | |105| | | | |110| |
|Val|Lys|Phe|Glu|Gly|Asp|Thr|Leu|Val|Asn|Arg|Ile|Glu|Leu|Lys|Gly|
| | | | |115| | | | |120| | | | |125| |
|Ile|Asp|Phe|Lys|Glu|Asp|Gly|Asn|Ile|Leu|Gly|His|Lys|Leu|Glu|Tyr|
| | |130| | | | |135| | | | |140| | | |
|Asn|Tyr|Asn|Ser|His|Asn|Val|Tyr|Ile|Met|Ala|Asp|Lys|Gln|Lys|Asn|
|145| | | | |150| | | | |155| | | | |160|
|Gly|Ile|Lys|Val|Asn|Phe|Lys|Ile|Arg|His|Asn|Ile|Glu|Asp|Gly|Ser|
| | | | |165| | | | |170| | | | |175| |
|Val|Gln|Leu|Ala|Asp|His|Tyr|Gln|Gln|Asn|Thr|Pro|Ile|Gly|Asp|Gly|
| | | |180| | | | |185| | | | |190| | |
|Pro|Val|Leu|Leu|Pro|Asp|Asn|His|Tyr|Leu|Ser|Thr|Gln|Ser|Ala|Leu|
| | | |195| | | | |200| | | | |205| | |
|Ser|Lys|Asp|Pro|Asn|Glu|Lys|Arg|Asp|His|Met|Val|Leu|Leu|Glu|Phe|
|210| | | | |215| | | | |220| | | | | |
|Val|Thr|Ala|Ala|Gly|Ile|Thr|Leu|Gly|Met|Asp|Glu|Leu|Tyr|Lys|Ser|
|225| | | | |230| | | | |235| | | | |240|
|Gly|Leu|Arg|Ser|Gly|Glu|Leu|Ser|Arg|Ile|Leu|Thr|Arg|Leu|Gln|Asp|
| | | |245| | | | |250| | | | |255| | |
|Ile|Lys|Leu|Met|Arg|Arg|Lys|Pro|Pro|Ala|Glu|Lys|Val|Met|Glu|Ile|
| | |260| | | | |265| | | | |270| | | |
|Lys|Leu|Ile|Lys|Gly|Pro|Lys|Gly|Leu|Gly|Phe|Ser|Ile|Ala|Gly|Gly|
| | |275| | | | |280| | | | |285| | | |
|Val|Gly|Asn|Gln|His|Ile|Pro|Gly|Asp|Asn|Ser|Ile|Tyr|Val|Thr|Lys|
| | |290| | | | |295| | | | |300| | | |
|Ile|Ile|Glu|Gly|Gly|Ala|Ala|His|Lys|Asp|Gly|Arg|Leu|Gln|Ile|Gly|
|305| | | | |310| | | | |315| | | | |320|
|Asp|Lys|Ile|Leu|Ala|Val|Asn|Ser|Val|Gly|Leu|Glu|Asp|Val|Met|His|
| | | |325| | | | |330| | | | |335| | |
|Glu|Asp|Ala|Val|Ala|Ala|Leu|Lys|Asn|Thr|Tyr|Asp|Val|Val|Tyr|Leu|
| | |340| | | | |345| | | | |350| | | |
|Lys|Val|Ala|Lys|Pro|
| | |355| | |

<210> SEQ ID NO 15
<211> LENGTH: 1050
<212> TYPE: DNA
<213> ORGANISM: Homo sapiens
<220> FEATURE:
<221> NAME/KEY: CDS
<222> LOCATION: (1)..(1050)
<223> OTHER INFORMATION: PDZ2-GFP DNA

<400> SEQUENCE: 15

| | | | | | | | | | | | | | | | | |
|---|---|---|---|---|---|---|---|---|---|---|---|---|---|---|---|---|
| atg | cgc | cgg | aag | ccc | ccg | gct | gag | aag | gtc | atg | gag | atc | aag | ctc | atc | 48 |
| Met | Arg | Arg | Lys | Pro | Pro | Ala | Glu | Lys | Val | Met | Glu | Ile | Lys | Leu | Ile | |
| 1 | | | 5 | | | | | 10 | | | | | 15 | | | |
| aag | ggg | cct | aaa | ggt | ctt | ggc | ttc | agc | atc | gca | ggg | ggc | gta | ggg | aac | 96 |
| Lys | Gly | Pro | Lys | Gly | Leu | Gly | Phe | Ser | Ile | Ala | Gly | Gly | Val | Gly | Asn | |
| | | | 20 | | | | 25 | | | | | 30 | | | | |
| cag | cac | atc | cca | gga | gat | aat | agc | atc | tat | gta | aca | aag | atc | atc | gaa | 144 |
| Gln | His | Ile | Pro | Gly | Asp | Asn | Ser | Ile | Tyr | Val | Thr | Lys | Ile | Ile | Glu | |
| | | 35 | | | | 40 | | | | | 45 | | | | | |
| ggg | ggt | gct | gcc | cac | aag | gat | ggg | agg | ttg | cag | att | gga | gac | aag | atc | 192 |
| Gly | Gly | Ala | Ala | His | Lys | Asp | Gly | Arg | Leu | Gln | Ile | Gly | Asp | Lys | Ile | |
| 50 | | | | 55 | | | | | 60 | | | | | | | |
| ctg | gcg | gtc | aac | agt | gtg | ggg | cta | gag | gac | gtc | atg | cat | gaa | gat | gct | 240 |
| Leu | Ala | Val | Asn | Ser | Val | Gly | Leu | Glu | Asp | Val | Met | His | Glu | Asp | Ala | |
| 65 | | | | 70 | | | | | 75 | | | | | 80 | | |
| gtg | gca | gcc | ctg | aag | aac | acg | tat | gat | gtt | gtc | tac | cta | aag | gtg | gcc | 288 |
| Val | Ala | Ala | Leu | Lys | Asn | Thr | Tyr | Asp | Val | Val | Tyr | Leu | Lys | Val | Ala | |
| | | | 85 | | | | 90 | | | | | 95 | | | | |
| aag | ccc | ggt | acc | gcg | ggc | ccg | gga | tcc | cca | ccg | gtc | gcc | acc | atg | gtg | 336 |
| Lys | Pro | Gly | Thr | Ala | Gly | Pro | Gly | Ser | Pro | Pro | Val | Ala | Thr | Met | Val | |
| | | 100 | | | | 105 | | | | | 110 | | | | | |
| agc | aag | ggc | gag | gag | ctg | ttc | acc | ggg | gtg | gtg | ccc | atc | ctg | gtc | gag | 384 |
| Ser | Lys | Gly | Glu | Glu | Leu | Phe | Thr | Gly | Val | Val | Pro | Ile | Leu | Val | Glu | |
| | 115 | | | | | 120 | | | | | 125 | | | | | |
| ctg | gac | ggc | gac | gta | aac | ggc | cac | aag | ttc | agc | gtg | tcc | ggc | gag | ggc | 432 |
| Leu | Asp | Gly | Asp | Val | Asn | Gly | His | Lys | Phe | Ser | Val | Ser | Gly | Glu | Gly | |
| | 130 | | | | | 135 | | | | | 140 | | | | | |
| gag | ggc | gat | gcc | acc | tac | ggc | aag | ctg | acc | ctg | aag | ttc | atc | tgc | acc | 480 |
| Glu | Gly | Asp | Ala | Thr | Tyr | Gly | Lys | Leu | Thr | Leu | Lys | Phe | Ile | Cys | Thr | |
| 145 | | | | | 150 | | | | | 155 | | | | | 160 | |
| acc | ggc | aag | ctg | ccc | gtg | ccc | tgg | ccc | acc | ctc | gtg | acc | acc | ctg | agc | 528 |
| Thr | Gly | Lys | Leu | Pro | Val | Pro | Trp | Pro | Thr | Leu | Val | Thr | Thr | Leu | Ser | |
| | | | | 165 | | | | | 170 | | | | | 175 | | |
| tac | ggc | gtg | cag | tgc | ttc | agc | cgc | tac | ccc | gac | cac | atg | aag | cag | cac | 576 |
| Tyr | Gly | Val | Gln | Cys | Phe | Ser | Arg | Tyr | Pro | Asp | His | Met | Lys | Gln | His | |
| | | | 180 | | | | | 185 | | | | | 190 | | | |
| gac | ttc | ttc | aag | tcc | gcc | atg | ccc | gaa | ggc | tac | gtc | cag | gag | cgc | acc | 624 |
| Asp | Phe | Phe | Lys | Ser | Ala | Met | Pro | Glu | Gly | Tyr | Val | Gln | Glu | Arg | Thr | |
| | | 195 | | | | | 200 | | | | | 205 | | | | |
| atc | ttc | ttc | aag | gac | gac | ggc | aac | tac | aag | acc | cgc | gcc | gag | gtg | aag | 672 |
| Ile | Phe | Phe | Lys | Asp | Asp | Gly | Asn | Tyr | Lys | Thr | Arg | Ala | Glu | Val | Lys | |
| 210 | | | | | 215 | | | | | 220 | | | | | | |
| ttc | gag | ggc | gac | acc | ctg | gtg | aac | cgc | atc | gag | ctg | aag | ggc | atc | gac | 720 |
| Phe | Glu | Gly | Asp | Thr | Leu | Val | Asn | Arg | Ile | Glu | Leu | Lys | Gly | Ile | Asp | |
| 225 | | | | 230 | | | | | 235 | | | | | 240 | | |
| ttc | aag | gag | gac | ggc | aac | atc | ctg | ggg | cac | aag | ctg | gag | tac | aac | tac | 768 |
| Phe | Lys | Glu | Asp | Gly | Asn | Ile | Leu | Gly | His | Lys | Leu | Glu | Tyr | Asn | Tyr | |
| | | | | 245 | | | | | 250 | | | | | 255 | | |
| aac | agc | cac | aac | gtc | tat | atc | atg | gcc | gac | aag | cag | aag | aac | ggc | atc | 816 |
| Asn | Ser | His | Asn | Val | Tyr | Ile | Met | Ala | Asp | Lys | Gln | Lys | Asn | Gly | Ile | |
| | | | 260 | | | | | 265 | | | | | 270 | | | |

```
aag gtg aac ttc aag atc cgc cac aac atc gag gac ggc agc gtg cag       864
Lys Val Asn Phe Lys Ile Arg His Asn Ile Glu Asp Gly Ser Val Gln
        275                 280                 285 ctc gcc gac cac tac cag cag aac acc ccc atc ggc gac ggc ccc gtg       912
Leu Ala Asp His Tyr Gln Gln Asn Thr Pro Ile Gly Asp Gly Pro Val
    290                 295                 300 ctg ctg ccc gac aac cac tac ctg agc acc cag tcc gcc ctg agc aaa       960
Leu Leu Pro Asp Asn His Tyr Leu Ser Thr Gln Ser Ala Leu Ser Lys
305                 310                 315                 320 gac ccc aac gag aag cgc gat cac atg gtg ctg ctg gag ttc gtg acc      1008
Asp Pro Asn Glu Lys Arg Asp His Met Val Leu Leu Glu Phe Val Thr
                325                 330                 335 gcc gcc ggg atc act ctc ggc atg gac gag ctg tac aag taa              1050
Ala Ala Gly Ile Thr Leu Gly Met Asp Glu Leu Tyr Lys
            340                 345

<210> SEQ ID NO 16
<211> LENGTH: 349
<212> TYPE: PRT
<213> ORGANISM: Homo sapiens

<400> SEQUENCE: 16

Met Arg Arg Lys Pro Pro Ala Glu Lys Val Met Glu Ile Lys Leu Ile
1               5                   10                  15

Lys Gly Pro Lys Gly Leu Gly Phe Ser Ile Ala Gly Gly Val Gly Asn
            20                  25                  30

Gln His Ile Pro Gly Asp Asn Ser Ile Tyr Val Thr Lys Ile Ile Glu
        35                  40                  45

Gly Gly Ala Ala His Lys Asp Gly Arg Leu Gln Ile Gly Asp Lys Ile
    50                  55                  60

Leu Ala Val Asn Ser Val Gly Leu Glu Asp Val Met His Glu Asp Ala
65                  70                  75                  80

Val Ala Ala Leu Lys Asn Thr Tyr Asp Val Val Tyr Leu Lys Val Ala
                85                  90                  95

Lys Pro Gly Thr Ala Gly Pro Gly Ser Pro Pro Val Ala Thr Met Val
            100                 105                 110

Ser Lys Gly Glu Glu Leu Phe Thr Gly Val Val Pro Ile Leu Val Glu
        115                 120                 125

Leu Asp Gly Asp Val Asn Gly His Lys Phe Ser Val Ser Gly Glu Gly
    130                 135                 140

Glu Gly Asp Ala Thr Tyr Gly Lys Leu Thr Leu Lys Phe Ile Cys Thr
145                 150                 155                 160

Thr Gly Lys Leu Pro Val Pro Trp Pro Thr Leu Val Thr Thr Leu Ser
                165                 170                 175

Tyr Gly Val Gln Cys Phe Ser Arg Tyr Pro Asp His Met Lys Gln His
            180                 185                 190

Asp Phe Phe Lys Ser Ala Met Pro Glu Gly Tyr Val Gln Glu Arg Thr
        195                 200                 205

Ile Phe Phe Lys Asp Asp Gly Asn Tyr Lys Thr Arg Ala Glu Val Lys
    210                 215                 220

Phe Glu Gly Asp Thr Leu Val Asn Arg Ile Glu Leu Lys Gly Ile Asp
225                 230                 235                 240

Phe Lys Glu Asp Gly Asn Ile Leu Gly His Lys Leu Glu Tyr Asn Tyr
                245                 250                 255

Asn Ser His Asn Val Tyr Ile Met Ala Asp Lys Gln Lys Asn Gly Ile
            260                 265                 270
```

```
Lys Val Asn Phe Lys Ile Arg His Asn Ile Glu Asp Gly Ser Val Gln
            275                 280                 285

Leu Ala Asp His Tyr Gln Gln Asn Thr Pro Ile Gly Asp Gly Pro Val
        290                 295                 300

Leu Leu Pro Asp Asn His Tyr Leu Ser Thr Gln Ser Ala Leu Ser Lys
305                 310                 315                 320

Asp Pro Asn Glu Lys Arg Asp His Met Val Leu Leu Glu Phe Val Thr
                325                 330                 335

Ala Ala Gly Ile Thr Leu Gly Met Asp Glu Leu Tyr Lys
            340                 345

<210> SEQ ID NO 17
<211> LENGTH: 1032
<212> TYPE: DNA
<213> ORGANISM: Homo sapiens
<220> FEATURE:
<221> NAME/KEY: CDS
<222> LOCATION: (1)..(1032)
<223> OTHER INFORMATION: RLuc-NR2B DNA

<400> SEQUENCE: 17
```

| | | | | | | | | | | | | | | | | |
|---|---|---|---|---|---|---|---|---|---|---|---|---|---|---|---|---|
| atg | acc | agc | aag | gtg | tac | gac | ccc | gag | cag | agg | aag | agg | atg | atc | acc | 48 |
| Met | Thr | Ser | Lys | Val | Tyr | Asp | Pro | Glu | Gln | Arg | Lys | Arg | Met | Ile | Thr | |
| 1 | | | | 5 | | | | | 10 | | | | | 15 | | |
| ggc | ccc | cag | tgg | tgg | gcc | agg | tgc | aag | cag | atg | aac | gtg | ctg | gac | agc | 96 |
| Gly | Pro | Gln | Trp | Trp | Ala | Arg | Cys | Lys | Gln | Met | Asn | Val | Leu | Asp | Ser | |
| | | | 20 | | | | | 25 | | | | | 30 | | | |
| ttc | atc | aac | tac | tac | gac | agc | gag | aag | cac | gcc | gag | aac | gcc | gtg | atc | 144 |
| Phe | Ile | Asn | Tyr | Tyr | Asp | Ser | Glu | Lys | His | Ala | Glu | Asn | Ala | Val | Ile | |
| | | 35 | | | | | 40 | | | | | 45 | | | | |
| ttc | ctg | cac | ggc | aac | gcc | gct | agc | agc | tac | ctg | tgg | agg | cac | gtg | gtg | 192 |
| Phe | Leu | His | Gly | Asn | Ala | Ala | Ser | Ser | Tyr | Leu | Trp | Arg | His | Val | Val | |
| | 50 | | | | | 55 | | | | | 60 | | | | | |
| ccc | cac | atc | gag | ccc | gtg | gcc | agg | tgc | atc | atc | ccc | gat | ctg | atc | ggc | 240 |
| Pro | His | Ile | Glu | Pro | Val | Ala | Arg | Cys | Ile | Ile | Pro | Asp | Leu | Ile | Gly | |
| 65 | | | | | 70 | | | | | 75 | | | | | 80 | |
| atg | ggc | aag | agc | ggc | aag | agc | ggc | aac | ggc | agc | tac | agg | ctg | ctg | gac | 288 |
| Met | Gly | Lys | Ser | Gly | Lys | Ser | Gly | Asn | Gly | Ser | Tyr | Arg | Leu | Leu | Asp | |
| | | | | 85 | | | | | 90 | | | | | 95 | | |
| cac | tac | aag | tac | ctg | acc | gcc | tgg | ttc | gag | ctc | ctg | aac | ctg | ccc | aag | 336 |
| His | Tyr | Lys | Tyr | Leu | Thr | Ala | Trp | Phe | Glu | Leu | Leu | Asn | Leu | Pro | Lys | |
| | | | 100 | | | | | 105 | | | | | 110 | | | |
| aag | atc | atc | ttc | gtg | ggc | cac | gac | tgg | ggc | gcc | tgc | ctg | gcc | ttc | cac | 384 |
| Lys | Ile | Ile | Phe | Val | Gly | His | Asp | Trp | Gly | Ala | Cys | Leu | Ala | Phe | His | |
| | | 115 | | | | | 120 | | | | | 125 | | | | |
| tac | agc | tac | gag | cac | cag | gac | aag | atc | aag | gcc | atc | gtg | cac | gcc | gag | 432 |
| Tyr | Ser | Tyr | Glu | His | Gln | Asp | Lys | Ile | Lys | Ala | Ile | Val | His | Ala | Glu | |
| | 130 | | | | | 135 | | | | | 140 | | | | | |
| agc | gtg | gtg | gac | gtg | atc | gag | agc | tgg | gac | gag | tgg | cca | gac | atc | gag | 480 |
| Ser | Val | Val | Asp | Val | Ile | Glu | Ser | Trp | Asp | Glu | Trp | Pro | Asp | Ile | Glu | |
| 145 | | | | | 150 | | | | | 155 | | | | | 160 | |
| gag | gac | atc | gcc | ctg | atc | aag | agc | gag | gag | ggc | gag | aag | atg | gtg | ctg | 528 |
| Glu | Asp | Ile | Ala | Leu | Ile | Lys | Ser | Glu | Glu | Gly | Glu | Lys | Met | Val | Leu | |
| | | | | 165 | | | | | 170 | | | | | 175 | | |
| gag | aac | aac | ttc | ttc | gtg | gag | acc | atg | ctg | ccc | agc | aag | atc | atg | aga | 576 |
| Glu | Asn | Asn | Phe | Phe | Val | Glu | Thr | Met | Leu | Pro | Ser | Lys | Ile | Met | Arg | |
| | | | 180 | | | | | 185 | | | | | 190 | | | |
| aag | ctg | gag | ccc | gag | gag | ttc | gcc | gcc | tac | ctg | gag | ccc | ttc | aag | gag | 624 |
| Lys | Leu | Glu | Pro | Glu | Glu | Phe | Ala | Ala | Tyr | Leu | Glu | Pro | Phe | Lys | Glu | |
| | | 195 | | | | | 200 | | | | | 205 | | | | |

```
aag ggc gag gtg aga aga ccc acc ctg agc tgg ccc aga gag atc ccc    672
Lys Gly Glu Val Arg Arg Pro Thr Leu Ser Trp Pro Arg Glu Ile Pro
    210                 215                 220 ctg gtg aag ggc ggc aag ccc gac gtg gtg cag atc gtg aga aac tac    720
Leu Val Lys Gly Gly Lys Pro Asp Val Val Gln Ile Val Arg Asn Tyr
225                 230                 235                 240 aac gcc tac ctg aga gcc agc gac gac ctg ccc aag atg ttc atc gag    768
Asn Ala Tyr Leu Arg Ala Ser Asp Asp Leu Pro Lys Met Phe Ile Glu
                245                 250                 255 agc gac ccc ggc ttc ttc agc aac gcc atc gtg gag ggc gcc aag aag    816
Ser Asp Pro Gly Phe Phe Ser Asn Ala Ile Val Glu Gly Ala Lys Lys
            260                 265                 270 ttc ccc aac acc gag ttc gtg aag gtg aag ggc ctg cac ttc agc cag    864
Phe Pro Asn Thr Glu Phe Val Lys Val Lys Gly Leu His Phe Ser Gln
        275                 280                 285 gag gac gcc ccc gac gag atg ggc aag tac atc aag agc ttc gtg gag    912
Glu Asp Ala Pro Asp Glu Met Gly Lys Tyr Ile Lys Ser Phe Val Glu
    290                 295                 300 aga gtg ctg aag aac gag cag ggg gat ctc ggc gag ctc tcg aga att    960
Arg Val Leu Lys Asn Glu Gln Gly Asp Leu Gly Glu Leu Ser Arg Ile
305                 310                 315                 320 ctc acg cgt ctg cag gat atc aag ctt gga cat gtt tat gag aaa ctt   1008
Leu Thr Arg Leu Gln Asp Ile Lys Leu Gly His Val Tyr Glu Lys Leu
                325                 330                 335 tct agt att gag tct gat gtc tga                                   1032
Ser Ser Ile Glu Ser Asp Val
            340

<210> SEQ ID NO 18
<211> LENGTH: 343
<212> TYPE: PRT
<213> ORGANISM: Homo sapiens

<400> SEQUENCE: 18

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190
```

```
Lys Leu Glu Pro Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Leu Pro Lys Met Phe Ile Glu
            245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
            275                 280                 285

Glu Asp Ala Pro Asp Glu Met Gly Lys Tyr Ile Lys Ser Phe Val Glu
            290                 295                 300

Arg Val Leu Lys Asn Glu Gln Gly Asp Leu Gly Glu Leu Ser Arg Ile
305                 310                 315                 320

Leu Thr Arg Leu Gln Asp Ile Lys Leu Gly His Val Tyr Glu Lys Leu
                325                 330                 335

Ser Ser Ile Glu Ser Asp Val
            340

<210> SEQ ID NO 19
<211> LENGTH: 1032
<212> TYPE: DNA
<213> ORGANISM: Homo sapiens
<220> FEATURE:
<221> NAME/KEY: CDS
<222> LOCATION: (1)..(1032)
<223> OTHER INFORMATION: RLuc-NR2B AA DNA (mutant)

<400> SEQUENCE: 19
```

| | | | | | | | | | | | | | | | | |
|---|---|---|---|---|---|---|---|---|---|---|---|---|---|---|---|---|
| atg | acc | agc | aag | gtg | tac | gac | ccc | gag | cag | agg | aag | agg | atg | atc | acc | 48 |
| Met | Thr | Ser | Lys | Val | Tyr | Asp | Pro | Glu | Gln | Arg | Lys | Arg | Met | Ile | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggc | ccc | cag | tgg | tgg | gcc | agg | tgc | aag | cag | atg | aac | gtg | ctg | gac | agc | 96 |
| Gly | Pro | Gln | Trp | Trp | Ala | Arg | Cys | Lys | Gln | Met | Asn | Val | Leu | Asp | Ser | |
| | | 20 | | | | | 25 | | | | | 30 | | | | |

| | | | | | | | | | | | | | | | | |
|---|---|---|---|---|---|---|---|---|---|---|---|---|---|---|---|---|
| ttc | atc | aac | tac | tac | gac | agc | gag | aag | cac | gcc | gag | aac | gcc | gtg | atc | 144 |
| Phe | Ile | Asn | Tyr | Tyr | Asp | Ser | Glu | Lys | His | Ala | Glu | Asn | Ala | Val | Ile | |
| | | | 35 | | | | | 40 | | | | | 45 | | | |

| | | | | | | | | | | | | | | | | |
|---|---|---|---|---|---|---|---|---|---|---|---|---|---|---|---|---|
| ttc | ctg | cac | ggc | aac | gcc | gct | agc | agc | tac | ctg | tgg | agg | cac | gtg | gtg | 192 |
| Phe | Leu | His | Gly | Asn | Ala | Ala | Ser | Ser | Tyr | Leu | Trp | Arg | His | Val | Val | |
| 50 | | | | | 55 | | | | | 60 | | | | | | |

| | | | | | | | | | | | | | | | | |
|---|---|---|---|---|---|---|---|---|---|---|---|---|---|---|---|---|
| ccc | cac | atc | gag | ccc | gtg | gcc | agg | tgc | atc | atc | ccc | gat | ctg | atc | ggc | 240 |
| Pro | His | Ile | Glu | Pro | Val | Ala | Arg | Cys | Ile | Ile | Pro | Asp | Leu | Ile | Gly | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| atg | ggc | aag | agc | ggc | aag | agc | ggc | aac | ggc | agc | tac | agg | ctg | ctg | gac | 288 |
| Met | Gly | Lys | Ser | Gly | Lys | Ser | Gly | Asn | Gly | Ser | Tyr | Arg | Leu | Leu | Asp | |
| | | | | 85 | | | | | 90 | | | | | 95 | | |

| | | | | | | | | | | | | | | | | |
|---|---|---|---|---|---|---|---|---|---|---|---|---|---|---|---|---|
| cac | tac | aag | tac | ctg | acc | gcc | tgg | ttc | gag | ctc | ctg | aac | ctg | ccc | aag | 336 |
| His | Tyr | Lys | Tyr | Leu | Thr | Ala | Trp | Phe | Glu | Leu | Leu | Asn | Leu | Pro | Lys | |
| | | | | 100 | | | | | 105 | | | | | 110 | | |

| | | | | | | | | | | | | | | | | |
|---|---|---|---|---|---|---|---|---|---|---|---|---|---|---|---|---|
| aag | atc | atc | ttc | gtg | ggc | cac | gac | tgg | ggc | gcc | tgc | ctg | gcc | ttc | cac | 384 |
| Lys | Ile | Ile | Phe | Val | Gly | His | Asp | Trp | Gly | Ala | Cys | Leu | Ala | Phe | His | |
| | | | 115 | | | | | 120 | | | | | 125 | | | |

| | | | | | | | | | | | | | | | | |
|---|---|---|---|---|---|---|---|---|---|---|---|---|---|---|---|---|
| tac | agc | tac | gag | cac | cag | gac | aag | atc | aag | gcc | atc | gtg | cac | gcc | gag | 432 |
| Tyr | Ser | Tyr | Glu | His | Gln | Asp | Lys | Ile | Lys | Ala | Ile | Val | His | Ala | Glu | |
| | | 130 | | | | | 135 | | | | | 140 | | | | |

-continued

```
agc gtg gtg gac gtg atc gag agc tgg gac gag tgg cca gac atc gag      480
Ser Val Val Asp Val Ile Glu Ser Trp Asp Glu Trp Pro Asp Ile Glu
145                 150                 155                 160 gag gac atc gcc ctg atc aag agc gag gag ggc gag aag atg gtg ctg      528
Glu Asp Ile Ala Leu Ile Lys Ser Glu Glu Gly Glu Lys Met Val Leu
            165                 170                 175 gag aac aac ttc ttc gtg gag acc atg ctg ccc agc aag atc atg aga      576
Glu Asn Asn Phe Phe Val Glu Thr Met Leu Pro Ser Lys Ile Met Arg
        180                 185                 190 aag ctg gag ccc gag gag ttc gcc gcc tac ctg gag ccc ttc aag gag      624
Lys Leu Glu Pro Glu Glu Phe Ala Ala Tyr Leu Glu Pro Phe Lys Glu
    195                 200                 205 aag ggc gag gtg aga aga ccc acc ctg agc tgg ccc aga gag atc ccc      672
Lys Gly Glu Val Arg Arg Pro Thr Leu Ser Trp Pro Arg Glu Ile Pro
210                 215                 220 ctg gtg aag ggc ggc aag ccc gac gtg gtg cag atc gtg aga aac tac      720
Leu Val Lys Gly Gly Lys Pro Asp Val Val Gln Ile Val Arg Asn Tyr
225                 230                 235                 240 aac gcc tac ctg aga gcc agc gac gac ctg ccc aag atg ttc atc gag      768
Asn Ala Tyr Leu Arg Ala Ser Asp Asp Leu Pro Lys Met Phe Ile Glu
            245                 250                 255 agc gac ccc ggc ttc ttc agc aac gcc atc gtg gag ggc gcc aag aag      816
Ser Asp Pro Gly Phe Phe Ser Asn Ala Ile Val Glu Gly Ala Lys Lys
        260                 265                 270 ttc ccc aac acc gag ttc gtg aag gtg aag ggc ctg cac ttc agc cag      864
Phe Pro Asn Thr Glu Phe Val Lys Val Lys Gly Leu His Phe Ser Gln
    275                 280                 285 gag gac gcc ccc gac gag atg ggc aag tac atc aag agc ttc gtg gag      912
Glu Asp Ala Pro Asp Glu Met Gly Lys Tyr Ile Lys Ser Phe Val Glu
290                 295                 300 aga gtg ctg aag aac gag cag ggg gat ctc ggc gag ctc tcg aga att      960
Arg Val Leu Lys Asn Glu Gln Gly Asp Leu Gly Glu Leu Ser Arg Ile
305                 310                 315                 320 ctc acg cgt ctg cag gat atc aag ctt gga cat gtt tat gag aaa ctt     1008
Leu Thr Arg Leu Gln Asp Ile Lys Leu Gly His Val Tyr Glu Lys Leu
            325                 330                 335 tct agt att gag gct gat gcc tga                                     1032
Ser Ser Ile Glu Ala Asp Ala
        340

<210> SEQ ID NO 20
<211> LENGTH: 343
<212> TYPE: PRT
<213> ORGANISM: Homo sapiens

<400> SEQUENCE: 20

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
```

```
            100                 105                 110
Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Gln Pro Phe Lys Glu
        195                 200                 205

Lys Gly Glu Val Arg Arg Pro Thr Leu Ser Trp Pro Arg Glu Ile Pro
210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
290                 295                 300

Arg Val Leu Lys Asn Glu Gln Gly Asp Leu Gly Glu Leu Ser Arg Ile
305                 310                 315                 320

Leu Thr Arg Leu Gln Asp Ile Lys Leu Gly His Val Tyr Glu Lys Leu
                325                 330                 335

Ser Ser Ile Glu Ala Asp Ala
            340

<210> SEQ ID NO 21
<211> LENGTH: 1284
<212> TYPE: DNA
<213> ORGANISM: Homo sapiens
<220> FEATURE:
<221> NAME/KEY: CDS
<222> LOCATION: (1)..(1284)
<223> OTHER INFORMATION: RLuc-PDR2 DNA

<400> SEQUENCE: 21 atg acc agc aag gtg tac gac ccc gag cag agg aag agg atg atc acc      48
Met Thr Ser Lys Val Tyr Asp Pro Glu Gln Arg Lys Arg Met Ile Thr
1               5                   10                  15 ggc ccc cag tgg tgg gcc agg tgc aag cag atg aac gtg ctg gac agc      96
Gly Pro Gln Trp Trp Ala Arg Cys Lys Gln Met Asn Val Leu Asp Ser
            20                  25                  30 ttc atc aac tac tac gac agc gag aag cac gcc gag aac gcc gtg atc     144
Phe Ile Asn Tyr Tyr Asp Ser Glu Lys His Ala Glu Asn Ala Val Ile
        35                  40                  45 ttc ctg cac ggc aac gcc gct agc agc tac ctg tgg agg cac gtg gtg     192
Phe Leu His Gly Asn Ala Ala Ser Ser Tyr Leu Trp Arg His Val Val
    50                  55                  60 ccc cac atc gag ccc gtg gcc agg tgc atc atc ccc gat ctg atc ggc     240
Pro His Ile Glu Pro Val Ala Arg Cys Ile Ile Pro Asp Leu Ile Gly
65                  70                  75                  80
```

| | |
|---|---|
| atg ggc aag agc ggc aag agc ggc aac ggc agc tac agg ctg ctg gac<br>Met Gly Lys Ser Gly Lys Ser Gly Asn Gly Ser Tyr Arg Leu Leu Asp<br>85                            90                        95 | 288 |
| cac tac aag tac ctg acc gcc tgg ttc gag ctc ctg aac ctg ccc aag<br>His Tyr Lys Tyr Leu Thr Ala Trp Phe Glu Leu Leu Asn Leu Pro Lys<br>100                        105                     110 | 336 |
| aag atc atc ttc gtg ggc cac gac tgg ggc gcc tgc ctg gcc ttc cac<br>Lys Ile Ile Phe Val Gly His Asp Trp Gly Ala Cys Leu Ala Phe His<br>115                        120                     125 | 384 |
| tac agc tac gag cac cag gac aag atc aag gcc atc gtg cac gcc gag<br>Tyr Ser Tyr Glu His Gln Asp Lys Ile Lys Ala Ile Val His Ala Glu<br>130                       135                   140 | 432 |
| agc gtg gtg gac gtg atc gag agc tgg gac gag tgg cca gac atc gag<br>Ser Val Val Asp Val Ile Glu Ser Trp Asp Glu Trp Pro Asp Ile Glu<br>145                   150                  155                   160 | 480 |
| gag gac atc gcc ctg atc aag agc gag gag ggc gag aag atg gtg ctg<br>Glu Asp Ile Ala Leu Ile Lys Ser Glu Glu Gly Glu Lys Met Val Leu<br>                  165                     170                   175 | 528 |
| gag aac aac ttc ttc gtg gag acc atg ctg ccc agc aag atc atg aga<br>Glu Asn Asn Phe Phe Val Glu Thr Met Leu Pro Ser Lys Ile Met Arg<br>              180                     185                   190 | 576 |
| aag ctg gag ccc gag gag ttc gcc gcc tac ctg gag ccc ttc aag gag<br>Lys Leu Glu Pro Glu Glu Phe Ala Ala Tyr Leu Glu Pro Phe Lys Glu<br>195                       200                   205 | 624 |
| aag ggc gag gtg aga aga ccc acc ctg agc tgg ccc aga gag atc ccc<br>Lys Gly Glu Val Arg Arg Pro Thr Leu Ser Trp Pro Arg Glu Ile Pro<br>210                       215                   220 | 672 |
| ctg gtg aag ggc ggc aag ccc gac gtg gtg cag atc gtg aga aac tac<br>Leu Val Lys Gly Gly Lys Pro Asp Val Val Gln Ile Val Arg Asn Tyr<br>225                        230                   235               240 | 720 |
| aac gcc tac ctg aga gcc agc gac gac ctg ccc aag atg ttc atc gag<br>Asn Ala Tyr Leu Arg Ala Ser Asp Asp Leu Pro Lys Met Phe Ile Glu<br>                  245                     250                   255 | 768 |
| agc gac ccc ggc ttc ttc agc aac gcc atc gtg gag ggc gcc aag aag<br>Ser Asp Pro Gly Phe Phe Ser Asn Ala Ile Val Glu Gly Ala Lys Lys<br>260                       265                   270 | 816 |
| ttc ccc aac acc gag ttc gtg aag gtg aag ggc ctg cac ttc agc cag<br>Phe Pro Asn Thr Glu Phe Val Lys Val Lys Gly Leu His Phe Ser Gln<br>275                       280                   285 | 864 |
| gag gac gcc ccc gac gag atg ggc aag tac atc aag agc ttc gtg gag<br>Glu Asp Ala Pro Asp Glu Met Gly Lys Tyr Ile Lys Ser Phe Val Glu<br>290                       295                   300 | 912 |
| aga gtg ctg aag aac gag cag ggg gat ctc ggc gag ctc tcg aga att<br>Arg Val Leu Lys Asn Glu Gln Gly Asp Leu Gly Glu Leu Ser Arg Ile<br>305                        310                   315               320 | 960 |
| ctc acg cgt ctg cag gat atc aag ctt atg cgc cgg aag ccc ccg gct<br>Leu Thr Arg Leu Gln Asp Ile Lys Leu Met Arg Arg Lys Pro Pro Ala<br>                  325                     330                   335 | 1008 |
| gag aag gtc atg gag atc aag ctc atc aag ggg cct aaa ggt ctt ggc<br>Glu Lys Val Met Glu Ile Lys Leu Ile Lys Gly Pro Lys Gly Leu Gly<br>340                       345                   350 | 1056 |
| ttc agc atc gca ggg ggc gta ggg aac cag cac atc cca gga gat aat<br>Phe Ser Ile Ala Gly Gly Val Gly Asn Gln His Ile Pro Gly Asp Asn<br>355                       360                   365 | 1104 |
| agc atc tat gta aca aag atc atc gaa ggg ggt gct gcc cac aag gat<br>Ser Ile Tyr Val Thr Lys Ile Ile Glu Gly Gly Ala Ala His Lys Asp<br>370                       375                   380 | 1152 |
| ggg agg ttg cag att gga gac aag atc ctg gcg gtc aac agt gtg ggg<br>Gly Arg Leu Gln Ile Gly Asp Lys Ile Leu Ala Val Asn Ser Val Gly<br>385                        390                   395               400 | 1200 |

```
cta gag gac gtc atg cat gaa gat gct gtg gca gcc ctg aag aac acg    1248
Leu Glu Asp Val Met His Glu Asp Ala Val Ala Ala Leu Lys Asn Thr
                405                 410                 415 tat gat gtt gtc tac cta aag gtg gcc aag ccc tag                    1284
Tyr Asp Val Val Tyr Leu Lys Val Ala Lys Pro
            420                 425

<210> SEQ ID NO 22
<211> LENGTH: 427
<212> TYPE: PRT
<213> ORGANISM: Homo sapiens

<400> SEQUENCE: 22

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln Gly Asp Leu Gly Glu Leu Ser Arg Ile
305                 310                 315                 320

Leu Thr Arg Leu Gln Asp Ile Lys Leu Met Arg Arg Lys Pro Pro Ala
                325                 330                 335
```

```
Glu Lys Val Met Glu Ile Lys Leu Ile Lys Gly Pro Lys Gly Leu Gly
            340                 345                 350

Phe Ser Ile Ala Gly Gly Val Gly Asn Gln His Ile Pro Gly Asp Asn
            355                 360                 365

Ser Ile Tyr Val Thr Lys Ile Ile Glu Gly Gly Ala Ala His Lys Asp
        370                 375                 380

Gly Arg Leu Gln Ile Gly Asp Lys Ile Leu Ala Val Asn Ser Val Gly
385                 390                 395                 400

Leu Glu Asp Val Met His Glu Asp Ala Val Ala Leu Lys Asn Thr
                405                 410                 415

Tyr Asp Val Val Tyr Leu Lys Val Ala Lys Pro
            420                 425

<210> SEQ ID NO 23
<211> LENGTH: 1269
<212> TYPE: DNA
<213> ORGANISM: Homo sapiens
<220> FEATURE:
<221> NAME/KEY: CDS
<222> LOCATION: (1)..(1269)
<223> OTHER INFORMATION: PDF2-RLuc DNA

<400> SEQUENCE: 23 atg cgc cgg aag ccc ccg gct gag aag gtc atg gag atc aag ctc atc       48
Met Arg Arg Lys Pro Pro Ala Glu Lys Val Met Glu Ile Lys Leu Ile
1               5                   10                  15 aag ggg cct aaa ggt ctt ggc ttc agc atc gca ggg ggc gta ggg aac       96
Lys Gly Pro Lys Gly Leu Gly Phe Ser Ile Ala Gly Gly Val Gly Asn
            20                  25                  30 cag cac atc cca gga gat aat agc atc tat gta aca aag atc atc gaa      144
Gln His Ile Pro Gly Asp Asn Ser Ile Tyr Val Thr Lys Ile Ile Glu
        35                  40                  45 ggg ggt gct gcc cac aag gat ggg agg ttg cag att gga gac aag atc      192
Gly Gly Ala Ala His Lys Asp Gly Arg Leu Gln Ile Gly Asp Lys Ile
    50                  55                  60 ctg gcg gtc aac agt gtg ggg cta gag gac gtc atg cat gaa gat gct      240
Leu Ala Val Asn Ser Val Gly Leu Glu Asp Val Met His Glu Asp Ala
65                  70                  75                  80 gtg gca gcc ctg aag aac acg tat gat gtt gtc tac cta aag gtg gcc      288
Val Ala Ala Leu Lys Asn Thr Tyr Asp Val Val Tyr Leu Lys Val Ala
                85                  90                  95 aag ccc ggt acc gcg ggc ccg gga tcc cca ccg gct aga gcc acc atg      336
Lys Pro Gly Thr Ala Gly Pro Gly Ser Pro Pro Ala Arg Ala Thr Met
            100                 105                 110 acc agc aag gtg tac gac ccc gag cag agg aag agg atg atc acc ggc      384
Thr Ser Lys Val Tyr Asp Pro Glu Gln Arg Lys Arg Met Ile Thr Gly
        115                 120                 125 ccc cag tgg tgg gcc agg tgc aag cag atg aac gtg ctg gac agc ttc      432
Pro Gln Trp Trp Ala Arg Cys Lys Gln Met Asn Val Leu Asp Ser Phe
    130                 135                 140 atc aac tac tac gac agc gag aag cac gcc gag aac gcc gtg atc ttc      480
Ile Asn Tyr Tyr Asp Ser Glu Lys His Ala Glu Asn Ala Val Ile Phe
145                 150                 155                 160 ctg cac ggc aac gcc gct agc agc tac ctg tgg agg cac gtg gtg ccc      528
Leu His Gly Asn Ala Ala Ser Ser Tyr Leu Trp Arg His Val Val Pro
                165                 170                 175 cac atc gag ccc gtg gcc agg tgc atc atc ccc gat ctg atc ggc atg      576
His Ile Glu Pro Val Ala Arg Cys Ile Ile Pro Asp Leu Ile Gly Met
            180                 185                 190
```

| | | | | | | | | | | | | | | |
|---|---|---|---|---|---|---|---|---|---|---|---|---|---|---|
| ggc | aag | agc | ggc | aag | agc | ggc | aac | ggc | agc | tac | agg | ctg | ctg | gac | cac | 624 |
| Gly | Lys | Ser | Gly | Lys | Ser | Gly | Asn | Gly | Ser | Tyr | Arg | Leu | Leu | Asp | His | |
| | | 195 | | | | 200 | | | | 205 | | | | | | |

```
ggc aag agc ggc aag agc ggc aac ggc agc tac agg ctg ctg gac cac    624
Gly Lys Ser Gly Lys Ser Gly Asn Gly Ser Tyr Arg Leu Leu Asp His
        195             200             205 tac aag tac ctg acc gcc tgg ttc gag ctc ctg aac ctg ccc aag aag    672
Tyr Lys Tyr Leu Thr Ala Trp Phe Glu Leu Leu Asn Leu Pro Lys Lys
210             215             220 atc atc ttc gtg ggc cac gac tgg ggc gcc tgc ctg gcc ttc cac tac    720
Ile Ile Phe Val Gly His Asp Trp Gly Ala Cys Leu Ala Phe His Tyr
225             230             235             240 agc tac gag cac cag gac aag atc aag gcc atc gtg cac gcc gag agc    768
Ser Tyr Glu His Gln Asp Lys Ile Lys Ala Ile Val His Ala Glu Ser
        245             250             255 gtg gtg gac gtg atc gag agc tgg gac gag tgg cca gac atc gag gag    816
Val Val Asp Val Ile Glu Ser Trp Asp Glu Trp Pro Asp Ile Glu Glu
        260             265             270 gac atc gcc ctg atc aag agc gag gag ggc gag aag atg gtg ctg gag    864
Asp Ile Ala Leu Ile Lys Ser Glu Glu Gly Glu Lys Met Val Leu Glu
        275             280             285 aac aac ttc ttc gtg gag acc atg ctg ccc agc aag atc atg aga aag    912
Asn Asn Phe Phe Val Glu Thr Met Leu Pro Ser Lys Ile Met Arg Lys
290             295             300 ctg gag ccc gag gag ttc gcc gcc tac ctg gag ccc ttc aag gag aag    960
Leu Glu Pro Glu Glu Phe Ala Ala Tyr Leu Glu Pro Phe Lys Glu Lys
305             310             315             320 ggc gag gtg aga aga ccc acc ctg agc tgg ccc aga gag atc ccc ctg   1008
Gly Glu Val Arg Arg Pro Thr Leu Ser Trp Pro Arg Glu Ile Pro Leu
        325             330             335 gtg aag ggc ggc aag ccc gac gtg gtg cag atc gtg aga aac tac aac   1056
Val Lys Gly Gly Lys Pro Asp Val Val Gln Ile Val Arg Asn Tyr Asn
        340             345             350 gcc tac ctg aga gcc agc gac gac ctg ccc aag atg ttc atc gag agc   1104
Ala Tyr Leu Arg Ala Ser Asp Asp Leu Pro Lys Met Phe Ile Glu Ser
        355             360             365 gac ccc ggc ttc ttc agc aac gcc atc gtg gag ggc gcc aag aag ttc   1152
Asp Pro Gly Phe Phe Ser Asn Ala Ile Val Glu Gly Ala Lys Lys Phe
370             375             380 ccc aac acc gag ttc gtg aag gtg aag ggc ctg cac ttc agc cag gag   1200
Pro Asn Thr Glu Phe Val Lys Val Lys Gly Leu His Phe Ser Gln Glu
385             390             395             400 gac gcc ccc gac gag atg ggc aag tac atc aag agc ttc gtg gag aga   1248
Asp Ala Pro Asp Glu Met Gly Lys Tyr Ile Lys Ser Phe Val Glu Arg
                405             410             415 gtg ctg aag aac gag cag taa                                       1269
Val Leu Lys Asn Glu Gln
            420

<210> SEQ ID NO 24
<211> LENGTH: 422
<212> TYPE: PRT
<213> ORGANISM: Homo sapiens

<400> SEQUENCE: 24

Met Arg Arg Lys Pro Ala Glu Lys Val Met Glu Ile Lys Leu Ile
1               5                   10                  15

Lys Gly Pro Lys Gly Leu Gly Phe Ser Ile Ala Gly Gly Val Gly Asn
                20                  25                  30

Gln His Ile Pro Gly Asp Asn Ser Ile Tyr Val Thr Lys Ile Ile Glu
            35                  40                  45

Gly Gly Ala Ala His Lys Asp Gly Arg Leu Gln Ile Gly Asp Lys Ile
        50                  55                  60
```

```
Leu Ala Val Asn Ser Val Gly Leu Glu Asp Val Met His Glu Asp Ala
 65                  70                  75                  80

Val Ala Ala Leu Lys Asn Thr Tyr Asp Val Val Tyr Leu Lys Val Ala
                 85                  90                  95

Lys Pro Gly Thr Ala Gly Pro Gly Ser Pro Pro Ala Arg Ala Thr Met
            100                 105                 110

Thr Ser Lys Val Tyr Asp Pro Glu Gln Arg Lys Arg Met Ile Thr Gly
        115                 120                 125

Pro Gln Trp Trp Ala Arg Cys Lys Gln Met Asn Val Leu Asp Ser Phe
    130                 135                 140

Ile Asn Tyr Tyr Asp Ser Glu Lys His Ala Glu Asn Ala Val Ile Phe
145                 150                 155                 160

Leu His Gly Asn Ala Ala Ser Ser Tyr Leu Trp Arg His Val Val Pro
                165                 170                 175

His Ile Glu Pro Val Ala Arg Cys Ile Ile Pro Asp Leu Ile Gly Met
            180                 185                 190

Gly Lys Ser Gly Lys Ser Gly Asn Gly Ser Tyr Arg Leu Leu Asp His
        195                 200                 205

Tyr Lys Tyr Leu Thr Ala Trp Phe Glu Leu Leu Asn Leu Pro Lys Lys
    210                 215                 220

Ile Ile Phe Val Gly His Asp Trp Gly Ala Cys Leu Ala Phe His Tyr
225                 230                 235                 240

Ser Tyr Glu His Gln Asp Lys Ile Lys Ala Ile Val His Ala Glu Ser
                245                 250                 255

Val Val Asp Val Ile Glu Ser Trp Asp Glu Trp Pro Asp Ile Glu Glu
            260                 265                 270

Asp Ile Ala Leu Ile Lys Ser Glu Glu Gly Lys Met Val Leu Glu
        275                 280                 285

Asn Asn Phe Phe Val Glu Thr Met Leu Pro Ser Lys Ile Met Arg Lys
    290                 295                 300

Leu Glu Pro Glu Glu Phe Ala Ala Tyr Leu Glu Pro Phe Lys Glu Lys
305                 310                 315                 320

Gly Glu Val Arg Arg Pro Thr Leu Ser Trp Pro Arg Glu Ile Pro Leu
                325                 330                 335

Val Lys Gly Gly Lys Pro Asp Val Val Gln Ile Val Arg Asn Tyr Asn
            340                 345                 350

Ala Tyr Leu Arg Ala Ser Asp Asp Leu Pro Lys Met Phe Ile Glu Ser
        355                 360                 365

Asp Pro Gly Phe Phe Ser Asn Ala Ile Val Glu Gly Ala Lys Lys Phe
    370                 375                 380

Pro Asn Thr Glu Phe Val Lys Val Lys Gly Leu His Phe Ser Gln Glu
385                 390                 395                 400

Asp Ala Pro Asp Glu Met Gly Lys Tyr Ile Lys Ser Phe Val Glu Arg
                405                 410                 415
```

Val Leu Lys Asn Glu Gln
          420

```
<210> SEQ ID NO 25
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is selected from E, Q, and A, or an
      analogue thereof
<220> FEATURE:
<221> NAME/KEY: MISC_FEATURE
<222> LOCATION: (3)..(3)
<223> OTHER INFORMATION: Xaa is selected from A, Q, D, N, N-Me-A,
      N-Me-Q, N-Me-D, and N-Me-N, or an analogue thereof

<400> SEQUENCE: 25

Xaa Thr Xaa Val
1

<210> SEQ ID NO 26
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is selected from E, Q, and A, or an
      analogue thereof
<220> FEATURE:
<221> NAME/KEY: MISC_FEATURE
<222> LOCATION: (3)..(3)
<223> OTHER INFORMATION: Xaa is selected from A, Q, D, N, N-Me-A,
      N-Me-Q, N-Me-D, and N-Me-N, or an analogue thereof

<400> SEQUENCE: 26

Xaa Ser Xaa Val
1
```

US 9,902,754 B2

MODIFIED PEPTIDES AS POTENT INHIBITORS OF THE PSD-95/NMDA RECEPTOR INTERACTION

CROSS REFERENCE TO RELATED APPLICATIONS

This application is a continuation of U.S. patent application Ser. No. 13/002,638 which is a U.S. National Phase of PCT/EP2009/058752 filed Jul. 9, 2009 depending from and claiming priority to Provisional Application No. 61/107,933 filed Oct. 23, 2008 and 61/079,290 filed Jul. 9, 2008, the entire contents of each of which are incorporated herein by reference.

FIELD OF THE INVENTION

The protein-protein interaction between the NMDA receptor and its intracellular scaffolding protein, PSD-95, is a potential target for treatment of ischemic or traumatic injury of the central nervous system (CNS). The present invention is directed to the provision of small molecule inhibitors of the PSD-95/NMDA receptor interaction, employing an undecapeptide corresponding to the C-terminal of the NMDA as a template for finding lead candidates.

BACKGROUND OF THE INVENTION

Protein-protein interactions (PPIs) are essential to vital cellular processes, and are involved in numerous patho-physiological states where they serve as potential targets for therapeutic intervention. PPIs have generally been perceived as difficult to target with small organic molecules, since they are often characterized by large, flat, and hydrophobic interfaces.

A class of PPIs is one involving PDZ domains [PDZ is an abbreviation for postsynaptic density protein-95 (PSD-95), *Drosophila* homologue discs large tumor suppressor (DlgA) and zonula occludens-1 protein (ZO-1)]. PDZ domains often function as modules in scaffolding proteins that are involved in assembling large protein complexes in the cell, and are highly abundant in eukaryotic organisms. PDZ domains comprise about 90 amino acids and generally interact with only a few amino acids of the C-terminal part of the interacting protein. PDZ domains are typically divided into three classes according to the sequence of their ligands. PSD-95, contains three PDZ domains, PDZ1-3, which bind peptide ligands with the consensus sequence Glu/Gln-Ser/Thr-X-Val-COOH (SEQ ID NO: 27), thus being designated class I PDZ domains.

The structural basis for the interaction of PDZ domains with C-terminal peptides was first elucidated by an X-ray crystallographic structure of PDZ3 of PSD-95 complexed with a native peptide ligand, CRIPT. PDZ3 contains six antiparallel β-strands (βA-βF) and two α-helices (αA and αB), and the C-terminal peptide ligand binds as an additional anti-parallel β-strand into a groove between the βB strand and αB helix. Two residues in the peptide ligand are considered particularly important for affinity and specificity, the first ($P^0$) and the third ($P^{-2}$) amino acids (counting from the C-terminal). The side chain of the amino acid in $P^0$ position projects into a hydrophobic pocket and an amino acid with an aliphatic side chains (Val, Ile and Leu) is required. In the PDZ3-CRIPT structure, the hydroxyl oxygen of Thr ($P^{-2}$) forms a hydrogen bond with the nitrogen of an imidazole side chain of His372, which is a highly conserved residue in class I PDZ domains. A conserved Gly-Leu-Gly-Phe (SEQ ID NO: 28) (position 322-325 in PDZ3) motif and a positively charged residue (Arg318 in PDZ3) of PDZ domains mediate binding to the C-terminal carboxylate group.

The PDZ1 and PDZ2 domains of PSD-95 interact with a number of proteins including a group of ionotropic glutamate receptors, the N-methyl-D-aspartate (NMDA) receptor. This receptor is a hetero tetrameric ion channel generally formed by the two subunits, NR1 and NR2, and gated by glutamate and glycine. The NMDA receptor (NMDAR) plays a key role in several diseases in the CNS brain, but development of drugs that directly interact with the NMDA receptor has been difficult. Therefore, there is a need for alternative approaches to modulate the NMDA receptor activity; one such approach is perturbation of the PSD-95/NMDA receptor interaction. PSD-95 simultaneously binds the NMDA receptor, primarily NR2A and NR2B subunits, and the enzyme neuronal nitric oxide synthase (nNOS) through PDZ1 or PDZ2 (FIG. 1). Activation of the NMDA receptor causes an influx of $Ca^{2+}$, which activates nNOS thereby leading to nitric oxide (NO) generation. Thus, PSD-95 mediates a specific association between NMDA receptor activation and NO production, which can be detrimental for the cells if sustained for a longer period (FIG. 1).

Inhibition of the PSD-95/NMDA receptor interaction is known to prevent ischemic brain damage in mice, presumably by impairing the functional link between $Ca^{2+}$ entry and NO production, while the physiological function of the NMDA receptor remains intact.[1] Uncoupling of PSD-95 from the NR2B subunit was achieved by a nonapeptide, corresponding to the C-terminal of NR2B, fused to HIV-1 Tat peptide, known for its ability to facilitate membrane permeability. This 20-mer peptide (Tat-NR2B, 3, Table 1) is currently in clinical trials as a potential drug for the treatment of cerebrovascular ischemia, as seen in stroke.[2-4] However, peptides are generally not attractive drug candidates due to their poor bioavailability, instability in vivo and low patient tolerance due to development of "immunogenicity" to the administered peptide.

The binding pocket of PDZ domains, which embeds a small, linear peptide motif, has a relatively small surface area and a non-favourable geometry, which makes PDZ domains difficult to target with small molecules. These difficulties are reflected by the very low number of small molecule inhibitors of PDZ domain interactions.

SUMMARY OF THE INVENTION

According to a first embodiment, the invention provides a compound comprising a (modified) peptide or (modified) peptide analogue, the peptide or peptide analogue comprising at least four amide-bonded residues having the sequence YTXV (SEQ ID NO: 29) or YSXV (SEQ ID NO: 30), wherein Y is selected from E, Q, and A, or an analogue of the selected residue; and X is selected from among A, Q, D, N, N-Me-A, N-Me-Q, N-Me-D, and N-Me-N, or an analogue of the selected residue, and wherein a residue of the peptide or peptide analogue is N-alkylated and wherein the N-alkylated residue is at position $P^{-3}$ corresponding to residue Y.

According to a second embodiment, the invention provides a compound comprising a first peptide or peptide analogue linked to a second peptide or peptide analogue by a linker, wherein the first and the second peptide or peptide analogue comprise at least four amide-bonded residues having the sequence YTXV (SEQ ID NO: 29) or YSXV (SEQ ID NO: 30), wherein Y is selected from among E, Q, and A, or an analogue of the selected residue, and X is selected from among A, Q, D, N, N-Me-A, N-Me-Q, N-Me-D, and N-Me-N or an analogue of the selected residue. The linker of the compound may comprise PEG, having a length of from 1 to 28 moieties (n=1-28) of ethylene glycol, preferably from 1 to 12 moieties (n=1-12), more preferably from 4 to 6 moieties (n=4-6).

A compound according to the second embodiment is further provided, wherein an amino acid residue of the first and/or the second peptide or peptide analogue may, or may not additionally be, N-alkylated, at position $P^{-3}$.

A compound according to the first or second embodiment is preferably one that is capable of inhibiting protein-protein interaction between NMDAR and PSD-95 (i.e. NMDAR/PSD-95 inhibitor).

A compound according to the first or second embodiment is provided, wherein the peptide or peptide analogue is 10, 9, 8, 7 or 6 amide-bonded residues in length, more preferably 5 or 4 amide-bonded residues in length.

A compound according to the first or second embodiment is provided, wherein the peptide or peptide analogue comprises at least 4 L-amino acid residues. Preferably the residue X in the compound is selected from among A, Q, and D.

A compound according to the first embodiment is provided, wherein the peptide or peptide analogue is N-alkylated (at position $P^{-3}$) with a cycloalkyl substituent, and further comprises a spacer group between the substituent and the terminal amino group of the peptide or peptide analogue, wherein the spacer is an alkyl group. The alkyl group is preferably selected from among methylene, ethylene, propylene and butylene. The cycloalkyl substituent in the compound may be cyclohexane.

A compound according to the first embodiment is provided, wherein the peptide or peptide analogue is N-alkylated (at position $P^{-3}$) with an aromatic substituent, and further comprises a spacer group between the substituent and a terminal amino group of the peptide, wherein the spacer is an alkyl group. The alkyl group is preferably selected from among methylene, ethylene, propylene and butylene. The aromatic substituent in the compound may be a naphthalen-2-yl moiety. Where the aromatic substituent in the compound is an aromatic ring, the aromatic ring may be substituted with one or two halogen atoms (for example chlorine or fluorine) and/or alkyl group.

A compound according to the first or second embodiment is provided, wherein the amino acid residue V in the peptide is substituted by tert-leucine.

A compound according to the first or second embodiment is provided, wherein the peptide or peptide analogue is covalently bonded to a polyamine or a diamine.

The invention further provides a complex comprising a PDZ domain and a compound according to the first or second embodiment. Preferably, the PDZ domain in the complex is a PDZ1 and/or a PDZ2 domain comprised in a PSD-95 protein.

The invention is further directed to the use of N-alkylation of an amino-terminal residue of a peptide or peptide analogue to enhance its affinity for a PDZ domain. Accordingly N-alkylation may be used to enhance the affinity of a compound according to the first or second embodiment for a PDZ domain of PSD-95. Preferably, the interaction is between NMDAR and PSD-95 and the NMDAR is comprised in a cell.

The invention is further directed to the use of a linker to dimerize a PDZ binding ligand or peptide in order to enhance its affinity and selectivity towards proteins containing tandem PDZ domains. Preferably the linker is a PEG linker comprising 1 to 28 PEG moieties, more preferably 1 to 12 PEG moieties, and the interaction is between NMDAR and PSD-95 and the NMDAR is comprised in a cell.

The invention further provides a pharmaceutical composition comprising a compound according to the first or second embodiment, for use as a medicament. The pharmaceutical composition may be used in the prophylaxis and/or treatment of an excitotoxic-related disease, preferably ischemic or traumatic injury of the CNS.

The invention further provides a kit comprising the pharmaceutical composition of the invention, further comprising means for delivering the composition to a subject.

DETAILED DESCRIPTION OF THE INVENTION

I. Definition of Abbreviations and Terms

Figure 1:
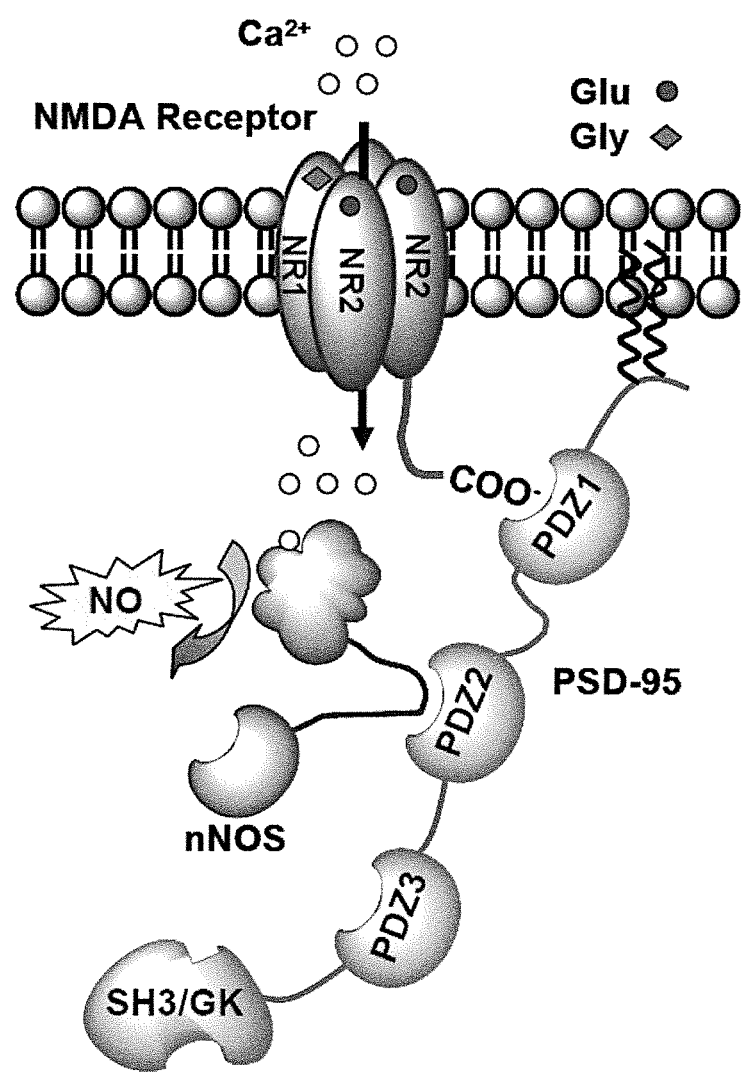
FIG. 1. Scheme showing NMDA receptor activation during ischemia. During ischemia an excessive amount of glutamate is released. This release activates the membrane bound NMDA receptors leading to $Ca^{2+}$ ions entering the cells. Due to the co-localization of NMDA receptors and nNOS mediated by PSD-95, this $Ca^{2+}$ influx is coupled to the potential harmful production of NO.

"A" or "a" as used herein, can mean one or more, depending on the context in which it is used.

Abu, 2-aminobutanoic acid;

Aib, α-aminoisobutyric acid;

Amide bond is formed by a reaction between a carboxylic acid and an amine. Where the reaction is between two amino acid residues, the bond formed as a result of the reaction is known as a peptide linkage (peptide bond);

Amino acid, that is naturally occurring, is named herein using either its 1-letter or 3-letter code according to the recommendations from IUPAC, see for example http://www.chem.qmw.ac.uk/iupac. If nothing else is specified an amino acid may be of D or L-form. In the description (but not in the sequence listing) a 3-letter code starting with a capital letter indicates an amino acid of L-form, whereas a 3-letter code in small letters indicates an amino acid of D-form;

cGMP, guanosine 3',5'-monophosphate;

"comprising" should be understood in an inclusive manner. Hence, by way of example, a composition comprising compound X, may comprise compound X and optionally additional compounds;

CNS, central nervous system;

CPP, cell penetrating peptide;

DAPI, 4', 6-diamidino-2-phenylindole;

DIPEA, diisopropylethylamine;

DMF, N,N-Dimethylformamide;

FP, fluorescence polarization;

GFP, green fluorescent protein

HATU, O-(7-azabenzotriazol-1-yl)-N,N,N',N'-tetramethyluronium hexafluorophosphate;

HBTU, O-(benzotriazol-1-yl)-N,N,N',N'-tetramethyluronium hexafluorophosphate;

ITC, Isothermal Titration Calorimetry;

"mammalian cell" is intended to indicate any cell of mammalian origin. The cell may be an established cell line, many of which are available from The American Type Culture Collection (ATCC, Virginia, USA) or a primary cell with a limited life span derived from a mammalian tissue, including tissues derived from a transgenic animal, or a newly established immortal cell line derived from a mammalian tissue including transgenic tissues, or a hybrid cell or cell line derived by fusing different cell types of mammalian origin e.g. hybridoma cell lines. The cells may optionally express one or more non-native gene products, e.g. receptors;

MCAO, middle cerebral artery occlusion;

nNOS, neuronal nitric oxide synthase;

NO, nitric oxide;

NMDA, N-methyl-D-aspartate;

NMDAR, NMDA receptor;

NMDAR/PSD-95 inhibitor, is a compound comprising a peptide or peptide analogue capable of binding to, or interacting with, PDZ domains and thereby inhibiting the PSD-95/NMDAR interaction, where the peptide or peptide analogue may be modified by N-alkylation (modified peptide inhibitor/modified peptide analogue inhibitor) at position $P^{-3}$. Alternatively, the inhibitor is a compound comprising two peptide or peptide analogues that are covalently linked by means of a linker;

$P^0$, Defined as the first amino acid residue or analogue corresponding to the C-terminal amino acid of the peptide/peptide analogue;

$P^{-1}$, Defined as the second amino acid residue or analogue thereof counting from the C-terminal amino acid of the peptide/peptide analogue;

$P^{-2}$, Defined as the third amino acid residue or analogue thereof counting from the C-terminal amino acid of the peptide/peptide analogue;

$P^{-3}$, Defined as the fourth amino acid residue or analogue thereof counting from the C-terminal amino acid of the peptide/peptide analogue.

PDZ, Postsynaptic density protein-95 (PSD-95), *Drosophila* homologue discs large tumor suppressor (DlgA), Zonula occludens-1 protein (zo-1);

PEG, polyethylene glycol; PEG is a polymer of ethylene glycol, where for example 12 PEG moieties, or PEG12, corresponds to a polymer of 12 moieties (n=12) of ethylene glycol.

PPIs, protein-protein interactions;

PSD-95, postsynaptic density protein-95;

rLUC, cytosolic *Renilla* Luciferase;

SEM, standard error of mean;

TIPS, 5% triisopropylsilane;

TMF, trifluoracetic acid;

WT, wild-type.

II. Chemical Structure and Properties of a Modified Peptide Inhibitor (NMDAR/PSD-95 Inhibitor) of the Invention According to a First Embodiment The NR2B undecapeptide 1 (YEKLSSIESDV (SEQ ID NO: 34)) has been used as a template for development of smaller non-peptide inhibitor molecules with the potential of uncoupling the PPI between PSD-95 and the NMDA receptor. By a number of modifications used for converting peptides into simplified non-peptide structures, a series of small peptide derivatives have been identified that demonstrate several fold improved affinities towards the PDZ domains of PSD-95, thereby providing drug-like inhibitors of the PSD-95/NMDA receptor interaction.

Specifically, a peptidomimetic approach was followed, starting with truncation of 1 from its N-terminus to a pentapeptide, IESDV (SEQ ID NO: 33) (7), without loss of affinity towards PDZ1 and PDZ2 of PSD-95, whereas further deletion reduced affinity. The decrease in affinity could be compensated by substituting Glu and Ser of the tetrapeptide ESDV (SEQ ID NO: 32) with N-Me-Glu and Thr, respectively, thereby resulting in N-methylated tetrapeptide, EMeTDV (SEQ ID NO: 35) (36), with improved affinity to PDZ1 and essentially WT affinity at PDZ2. The Asp residue could be replaced with the non-charged Gln or the hydrophobic Ala without affecting affinity significantly, providing $E_{Me}TAV$ (SEQ ID NO: 31) (40) as a promising lead. Interestingly, a tripeptide TAV (49) is still a reasonably potent inhibitor of PDZ1 and PDZ2 with $K_i$ values of 42 and 37 μM, respectively, thus only ca. 2- and 9-fold less potent than the NRB2B peptide (1), while still showing selectivity within the PDZ domains of PSD-95.

Figure 10:
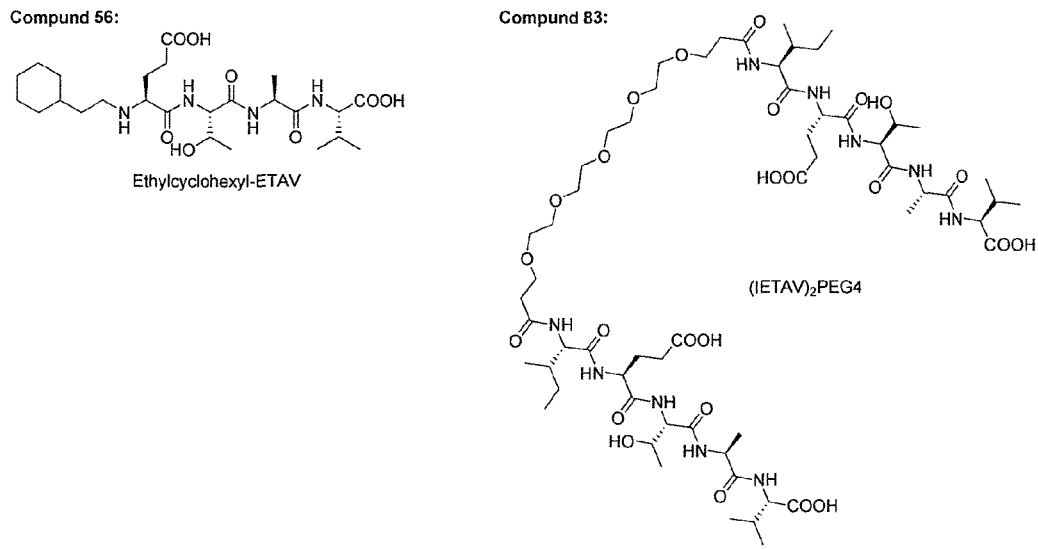
FIG. 10. Structure of compounds 56 and 83.

Guided by molecular modeling and docking of peptides and modified peptides into a homology model of PDZ1, modification of the N-terminal methyl group of $E_{Me}TAV$ (SEQ ID NO: 31) was pursued. Applying the Fukuyama protocol of the Mitsunobu reaction allowed the preparation of 11 N-alkylated tetrapeptides, which all had superior affinity at PDZ1 and PDZ2 compared to the lead peptide $E_{Me}$TAV (SEQ ID NO: 31). In particular, replacing the methyl group with either cyclohexylmethyl (55) or cyclohexylethyl (56) provided potent inhibitors of the PSD-95/NMDA receptor interaction, the most potent being (56) with $K_i$ values of 1 and 0.5 µM at PDZ1 and PDZ2, respectively (structures in FIG. 10). In addition, introduction of aromatic substituents provided almost equipotent compounds, as exemplified by compound 62 and 63. Although, PDZ3 binding was also increased by the N-terminal alkylations a considerable selectivity towards PDZ1 and 2 was still observed.

The present invention teaches that N-alkylation in position $P^{-3}$ can be used to increase the affinity of a peptide or peptide analogue for one or more target PDZ domain, thereby enhancing its ability to prevent PPI interactions occurring with said target. Where the PPI interaction is between NMDAR/PSD-95 inhibitor, the peptide or peptide analogue preferably comprises at least 4 amide linked residues and the sequence YTXV (SEQ ID NO: 29) or YSXV (SEQ ID NO: 30), wherein Y is selected from among E, Q, and A, or an analogue thereof, and X is selected from among A, Q, D, N, N-Me-A, N-Me-Q, N-Me-D, and N-Me-N or an analogue thereof. Suitable analogues of residue Y or X, or analogues of any of the 4 amide-linked residues (YTXV (SEQ ID NO: 29) or YSXV (SEQ ID NO: 30)), include: inverso-amides and/or thioamides (Chemistry & Biochemistry of amino acids, peptides, and proteins", vol 7, 1983, Boris Weinstein, Ch. 5 by Arno F. Spatola); the aza-@-unit (5-dihydro-2(3H)-pyrazone moiety), particularly position $P^{-1}$ or $P^{-3}$ corresponding to residue X or Y (Hammond et al, Chemistry and Biology, 2006, p. 1247); where the choice of analogue may be assisted by use of the tools and assays for a peptidomimetic approach as described herein.

III Optimizing Modified Peptide Inhibitors (NMDAR/PSD-95 Inhibitor) According to a First and Second Embodiment with Regard to Membrane Permeability, Selectivity and Pharmacokinetic Properties The probability that the modified peptide inhibitors penetrate cellular membranes would be increased by decreasing their polarity and charge. Surprisingly, modifications in the peptide sequence of N-alkylated YTXV (SEQ ID NO: 29) (Y=Glu, Ala or Gln and X=Asp and Ala) to decrease polarity and/or charge do not significantly impair their affinity to PDZ1 and PDZ2 of PSD-95. The tetrapeptides were N-alkylated with cyclohexylethyl and compared with their non-alkylated versions with regards to affinity and selectivity for PSD-95's PDZ domains. Non-charged and even small and hydrophobic amino acids could be positioned in these variable regions, individually or in combination, without significant loss in affinity (compounds 70-73). It was also noticed that the effect of N-alkylation was as significant as observed previously, thereby underlining the reproducibility and generality of N-alkylation as a modification that increases the affinity of the peptide inhibitors to PDZ1 and PDZ2 of PSD-95. The present invention thus provides N-alkylated peptide ligands whose size may be reduced to a tetrapeptide, and whose affinity for PDZ1 and PDZ2 is far greater than that of either the WT peptide sequence or Tat-NR2B (3). The N-alkylated peptide ligands of the invention, when compared to known peptide ligands, also have a reduced risk of immunogenicity and lower production cost, due to their smaller size. Furthermore, N-terminal alkylation of a peptide ligand of the invention (e.g. at $P^{-3}$), in contrast to other peptide derivatization techniques (such as the "natural occurring" acetylation, glycosylation or phosphorylation) serves to enhance its hydrophobicity and thereby increase its membrane permeability. Thereby the compounds are able to inhibit the PSD-95/NMDA receptor interaction intracellularly, thus reducing NMDA-mediated excitotoxicity in cultured cortical rat neurons.

According to the second embodiment, the invention further provides modified peptide inhibitors comprising two peptide (or peptide analogue) inhibitors linked together to form a dimeric ligand (as exemplified by 74 and 75). The two peptides or peptide analogues may have the same structure and composition or may have a different structure and composition. The peptide or peptide analogues in the dimeric ligand, in a further embodiment, may be additionally N-alkylated at $P^{-3}$ in the same chemical forms as described for a peptide of peptide analogue of the first embodiment. By binding to PDZ1 and PDZ2 of PDZ1-2 simultaneously, the affinity of the dimeric ligand to the tandem PSD-95 PDZ1-2 construct is dramatically increased, while remaining constant with respect to the single PDZ domains PDZ1, 2 and 3. The peptide inhibitors are linked together by means of a linker. Suitable linkers include a linker composed of polyethylene glycol (PEG) diacid; polyamine (Hervé F et al, 2008, AAPS J, E-publ. August 26); peptide nucleic acid (PNA) (Egholm et al., 2005 Nature 365:566-568); locked nucleic acid (LNA) (Singh et al., 1998, Chem Comm, p. 455). When the linker is a PEG linker it may also comprise an active functional group, such as an electrophilic or nucleophilic functional group (WO/2007/140282), which can be used to attach the PEG linker to each peptide (or peptide analogue) inhibitor. Suitable functional groups for attachment include amino-reactive electrophilic groups, selected from among N-hydroxysuccinimide (NHS) ester, p-nitrophenyl ester, succinimidyl carbonate, p-nitrophenyl carbonate, succinimidyl urethane, isocyanate, isothiocyanate, acyl azide, sulfonyl chloride, aldehyde, carbonate, imidioester or anhydride; and thio-reactive groups selected from among maleimide, haloacetyl, alkyl halide derivatives, aziridine, acryloyl derivatives arylating agents or thio-disulfide exchange reagents. Suitable nucleophilic functional groups include amine, hydrazide, carbazate, acyl hydrazide, semicarbamate or hydrazine, which can undergo reactions with aldehyde or carboxyl groups on the peptide or peptide analogue inhibitor.

The optimal length of linker in the dimeric ligand will depend on the selected linker. When the linker is PEG, the number of ethylene glycol moieties (n) of PEG may lie between n=1-28 or n=4-28, or the linker may have a length of n=1, 2, 3, 4, 5, 6, 7, 8, 9, 10, 11, or 12. According to the present invention, PEG-diacids are used to link ligands (peptides or peptide analogues), where the e.g. PEG12-linker is modified so that two carboxylic acid groups are present at each end of the linker. Thus, a PEG12-linker prior to the dimerization process is named 4,7,10,13,16,19,22,25, 28,31,34,37,40-tridecaoxatritetracontane-1,43-dioic acid. During dimerization of the two peptide ligands with the linker, the two carboxylic acid groups react with the N-terminal amino groups of the ligands to create amide bonds. The PEG0,1,2,4,6,8 linkers are in accordance with this description. A PEG linker having 12 moieties (n=12) will, when stretched out, have a length of about 50 Å, which will easily allow the ligands at each end of the linker to be in sufficiently close proximity with the tandem PDZ domain and thereby act together as a potent inhibitor. The distance between PDZ1 and PDZ2 in PSD-95 has been modeled and estimated to be around 20 Å, (measured from the two conserved histidines on αB) (Long et al, JMB, 2003, p. 203-214). Accordingly, the PEG linker in the dimeric ligand preferably comprises 1-12 moieties (n=1-12), more preferably 2-12 (n=2-4) and even more preferably 4-6 (n=4-6) moieties. The dimeric ligands of the invention possess several advantages: Their affinity to the tandem PDZ1-2 construct is increased significantly—up to 1000-fold compared to WT or Tat-NR2B (3). The affinity of these ligands to the tandem PDZ1-2 protein, which shares the greatest structural similarity to the native PSD-95 protein target for these modified peptide inhibitors, is of key importance with respect to their efficacy during therapeutic use. Also, the PDZ1-2 tandem corresponds to a much more distinctive protein target as compared to single PDZ domains, which are rather promiscuous in nature. Therefore, by providing dimerized ligand peptide inhibitors that specifically target the PDZ1-2, an improvement in selectivity is obtained compared to monomeric ligands, which is potentially important for the therapeutic use of these inhibitors. In addition PEG modification of peptides offers several pharmacokinetic advantages such as decreasing immunogenicity, delaying clearance from the blood and reducing sensitivity towards proteases. Furthermore, PEG is non-toxic, highly soluble and known to facilitate cellular uptake, and the dimeric ligands are also shown to inhibit the PSD-95/NMDA receptor interaction intracellularly, hence reducing NMDA-mediated excitotoxicity in cultured cortical rat neurons. Thus besides functioning as a linker, PEG enhances the therapeutic properties of these modified peptide inhibitors.

The membrane permeability and blood-brain barrier permeability of the peptide or peptide analogues of the present invention may be further enhanced by cationization with a natural or synthetic polyamine or diamine (e.g. hexamethylenediamine; putresine; spermidine; spermine), which may be covalently linked to the peptide or peptide analogue (Hervé F et al, 2008, AAPS J, p. 455-472). Preferably the peptide or peptide analogues includes the cationization at its N-terminus.

Linking PEG12-diacid (4,7,10,13,16,19,22,25,28,31,34,37,40-tridecaoxatritetracontane-1,43-dioic acid), PEG8-diacid (4,7,10,13,16,19,22,25,28-nonaoxahentriacontane-1,31-dioic acid), PEG6-diacid (4,7,10,13,16,19,22-heptaoxapentacosane-1,25-dioic acid), and PEG4-diacid (4,7,10,13,16-pentaoxanonadecane-1,19-dioic acid) to two pentapeptide molecules with the sequence IESDV (SEQ ID NO: 33), result in the dimeric ligands 74, 76, 77, and 78 respectively, which demonstrate one or more of the properties of high affinity binding to the PDZ12 protein target, complete resistance to proteolytic enzymes in blood plasma, membrane permeability and activity in a cell-based excitotoxicity ex vivo assay. Affinity is increased even further by dimerization of the pentapeptide having the sequence IETAV (SEQ ID NO: 36), to get compound 83, while plasma stability is still pronounced—especially compared to the monomeric peptide ligand.

IV Tools for Monitoring and Evaluating the Inhibitor Properties of the NMDAR/PSD-95 Inhibitor of the Invention A. Fluorescence Polarization (FP) Assay:
as described below in Example 1 and in the Methodology section, provides a convenient and reliable way to monitor and evaluate the inhibitor properties of an NMDAR/PSD-95 inhibitor of the invention. The FP assay allows a wide range of peptide analogues to be tested and compared with respect to their interaction with PDZ domains, and their specificity with respect to the three PDZ domains, PDZ1-3, of PSD-95. PDZ domains may be expressed individually, or as tandem domain constructs, using standard recombinant DNA technology known to those skilled in the art. Purification of the expressed PDZ domains may be facilitated by the inclusion of an affinity tag (e.g. poly-histidine-tag, Glutathione-S-transferase-tag, or antibody-tag such as FLAG-tag) in the expressed protein comprising the PDZ domain (e.g. fusion protein), and the use of an affinity resin to selective purify tagged PDZ domain proteins.

More specifically, the assay is based on a heterologous competition binding assay, where the affinity measured as $IC_{50}$ of a given (non-fluorescent) peptide analogue for a PDZ domain is measured in the presence of a fixed concentration of a fluorescent labelled undecapeptide peptide corresponding to the wild-type (WT) C-terminal of the NR2B subunit (YEKLSSIESDV (SEQ ID NO: 34)) and CRIPT (LDTKNYKQTSV (SEQ ID NO: 37)). Determined $IC_{50}$ values may be converted to $K_i$ values.[5] Suitable fluorophores include either 5-FAM or Cy5, which may be coupled to a tripeptide (KSG or CSG) linker attached to the N-terminus of the undecapeptide, to give 5-FAM-NR2B, Cy5-NR2B, 5-FAM-CRIPT and Cy5-CRIPT. The 5-FAM fluorophore may be attached to the undecapeptides by coupling with HATU. The Cy5 fluorophore may be conjugated to the undecapeptides by coupling Cy5-maleimide to the cysteine side chain of the tripeptide sequence CSG attached to the N-terminus of the peptide, as detailed in the Methodology section.

B. Pull-Down Assay:
The polyhistidine pull-down is an in vitro technique that consists of a polyhistidine-tagged bait NRB2 or CRIPT protein C-terminal domain (e.g NR2B WT peptide with the sequence HHHHHHYEKLSSIESDV (SEQ ID NO: 38)) that can be used to identify competitors of a PDZ domain-binding partner (PDZ domain of PSD-95) (the prey). The bait protein is immobilized on cobalt chelated affinity gel. The bait serves as the secondary affinity support for the protein partner to the bait and for identifying competitors that can displace the prey from the bait. The competitors are peptide analogues, specifically an NMDAR/PSD-95 inhibitor of the present invention. PPIs, between the prey and bait are analyzed by chemically dissociating/eluting the bound prey (PDZ domain or peptide analogue) and visualizing the prey by SDS-PAGE and associated detection methods depending on the sensitivity requirements of the interacting proteins. These methods include Coomassie® Dye, silver, and zinc staining; western blotting; and [35S] radioisotopic detection. Alternatively, the displaced prey detected on the gel, can be isolated from a polyacrylamide gel, and further analyzed. Suitable pull-down assay protocols are well known in the art (Sambrook, J. and Russell, D. W. (2001). Molecular Cloning: A Laboratory Manual. Cold Spring Harbor Laboratory Press: Cold Spring Harbor, N.Y. 3rd edition), while ProFound™ Pull-Down PolyHis Protein: Protein Interaction Kit from Pierce Biotechnology, 3747 N. Meridian Road, P.O. Box 117 Rockford, Ill. 61105 contains a complete, validated set of reagents specifically developed for performing pull-down assays.

C. Isothermal Titration Calorimetry (ITC):
This technique (Pierce, M. et al., 1999., Methods, p. 213-221) provides an exact determination of the affinity of a ligand for its target protein, as well as measuring the thermodynamic properties of the interaction, including enthalpy ($\Delta H$), entropy ($\Delta S$) and free energy ($\Delta G$) together with the stoichiometric relationship of ligand binding. In this method, un-labeled ligand is titrated into a solution of un-labeled PDZ protein located in the calorimeter. Heat generated upon protein recognition is measured ($\Delta H$) during the titration of the ligand and the PDZ protein until saturation is achieved, and the heat-exchange upon further ligand addition is negligible. Based on the amount of ligand needed to achieve saturation an affinity constant ($K_d$) is calculated and in addition $\Delta H$, $\Delta S$, $\Delta G$ and stoichiometry are determined.

D. Blood Plasma Stability Assay.

In this assay, the half-life ($T_{1/2}$) of a compound in blood plasma is measured in vitro, whereby its susceptibility to degradation by proteases, peptidases and general plasma contents is quantified.

E. Neuronal NMDA Toxicity Assay.

When cultured cortical neurons are exposed to high concentrations of NMDA, an excitotoxic cascade is initiated, which leads to cellular damage and ultimately neuronal cell death. Consequently, the cell membranes are destroyed, and cytoplasmic enzymes are released into the cell surroundings. The extent of this neuronal cell death can be quantified by measuring the release of cytoplasmic lactate dehydrogenase (LDH) enzyme into the cell medium. The compounds of interest and control compound (3) are investigated with respect to their abilities to attenuate NMDA-mediated toxicity. Compounds that are active in this assay are both membrane permeable, and can prevent ex vivo excitotoxicity, which are important properties for therapeutics towards excitotoxicity mediated diseases.

F. Bioluminescence Resonance Energy Transfer2 (BRET):

This assay can be used to assess the cell permeability of an NMDAR/PSD-95 inhibitor, which is important for its bioavailability required for the effective therapeutic treatment of a mammalian subject. A mammalian cell line can be transfected with pairs of DNA constructs encoding two fusion proteins, comprising a GFP-fusion protein (e.g. GFP-NR2B) and a rLUC-fusion protein (e.g. rLUC-PDZ2). Interaction between the two fusion proteins, when expressed in a transfected cell, can be monitored by virtue of the BRET between the two fusion proteins on binding to each other. The ability of an NMDAR/PSD-95 inhibitor, when added to extracellularly, to cross the cell membrane and inhibit the interaction between the two fusion proteins can be monitored with the BRET assay, providing a valuable measure of the therapeutic potential of the NMDAR/PSD-95 inhibitor of the invention.

V Methods for Synthesising the NMDAR/PSD-95 Inhibitor of the Invention and for Verifying its Composition and Structure A. Synthesis of peptide analogues: Fmoc-based solid-phase peptide synthesis (SPPS) provides a suitable procedure for the synthesis of the peptide analogues, whereby an NMDAR/PSD-95 inhibitor of the invention may be prepared. Peptides with a natural C-terminal amino acid residue, such as Val or Ala, may be synthesized starting with pre-loaded Wang resins. In the case of peptides having an unnatural C-terminal amino acid residue, then a 2-chlorotrityl resin may be used, where the residue may be loaded on the resin using diisopropylethylamine (DIPEA) (resin/amino acid/DIPEA in 1:4:8) in DCM for 30 min., then capped with methanol, prior to Fmoc deprotection and coupling of the consecutive amino acid residue. N-methylated amino acids and the amino acid following the N-methylated amino acid may be coupled to the growing peptide using HATU. A detailed description of a suitable Fmoc-based SPPS protocol is given below in the Methodology section.

Figure 6:
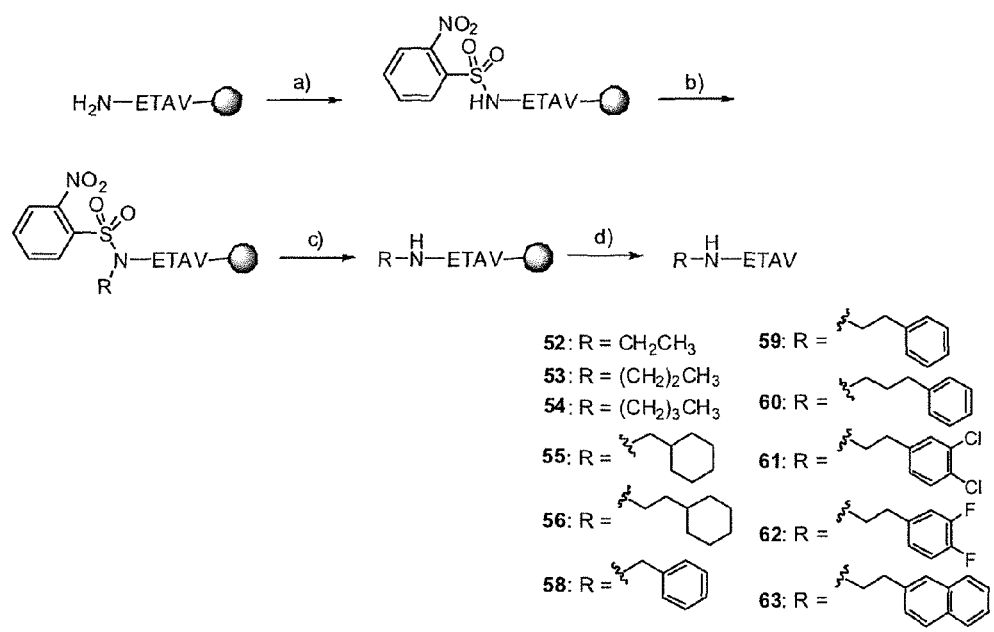
FIG. 6. N-terminal alkylation of peptide analogues according to Scheme 1$^a$. Reagents and conditions: (a) o-Nitrobenzenesulfonyl chloride, DIPEA. (b) $Ph_3P$, ROH, DIAD (c) NaSPh, DMF (d) TFA, TIPS, $H_2O$ (90:5:5).
Figure 7:
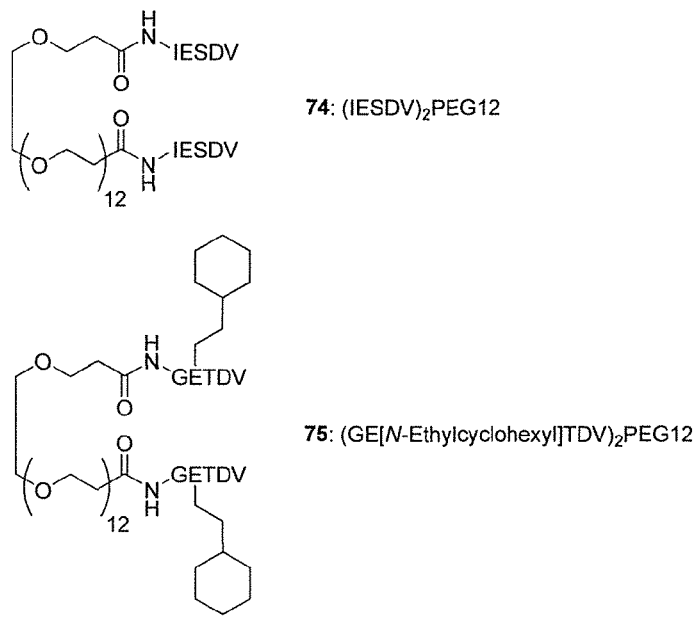
FIG. 7. Chemical structure of the dimeric compounds 74 and 75. For compound 75 the cyclohexylethyl group is positioned on the nitrogen of Glu (E) in $P^{-3}$.

B. N-Terminal Alkylation of Peptide Analogues:

The Mitsunobu reaction using the Fukuyama protocol[6] provides a suitable procedure for the preparation of N-alkylated peptides.[7] The terminal amino group of the peptide is activated as a nitrobenzyl sulfonamide, and subsequently reacted with a range of alcohols mediated by diisopropyl azadicarboxylate (DIAD) and $Ph_3P$ to give the protected, resin-bound products (FIG. 6/Scheme 1). The final N-alfkylated products, obtained by deprotection of the sulfonamide and cleavage from the resin, have the required purity and yield.

C. Synthesis of Dimeric Ligands:

PEG-diacids are activated as pentafluorophenyl (Pfp)-esters and reacted with the N-terminal amino group of the resin-bound peptide ligand by using 1-hydroxybenzotriazole (HOBt) as a catalyst. Thereby, a dimeric ligand composed of two peptide ligands linked together by the PEG-linker through amide bonds is generated.[8] Alternatively, the dimeric ligands can be produced by activating the PEG-diacids in situ with coupling reagents such as HBTU and HATU, followed by incubation with the N-terminal amino group of the resin-bound peptide ligand. Using this procedure, the dimerization procedure is limited to a one-step reaction and can be performed in one day instead of six.

D. Chemical Analysis of Peptide Analogues:

The peptide may be analyzed by ESI-LC/MS, and further characterised by proton ($^1H$) NMR spectra and high resolution mass spectrometry, employing techniques well-known to the skilled man, and exemplified in the Methodology section.

VI. NMDAR/PSD-95 Inhibitors According to the First or Second Embodiment of the Invention for Therapeutic Treatment of Excitotoxic-Related Disorders Ischemic or Traumatic Injury of the Central Nervous System In neuronal synapses, the C-termini of NMDA receptor subunits interact with PDZ domains of PSD-95 linking them to downstream neurotoxic signaling molecules (e.g nNOS) leading to NO production and excitotoxicity. The present invention provides NMDAR/PSD-95 inhibitors that can inhibit the interaction between NMDA receptors and nNOS in a cell, without impairing the NMDAR ionic currents and calcium signalling functions of the NMDAR. Thus an NMDAR/PSD-95 inhibitor of the invention acts as a neuroprotectant of one or more cells or tissues providing a specific strategy for treating excitotoxic disorders, including spinal cord injury, stroke, traumatic brain injury, ischemic or traumatic injury of the central nervous system (CNS), epilepsy, and neurodegenerative diseases of the CNS.

Therapeutic treatment of subjects at risk or presently suffering from the above disorders and diseases may be given either prophylactic treatment to reduce the risk of the disorder or disease onset or therapeutic treatment following the disorder or disease onset. The subject may be a mammalian or human patient.

VII. Manufacture of a Pharmaceutical Composition Comprising NMDAR/PSD-95 Inhibitor According to the First or Second Embodiment of the Invention Formulations of an NMDAR/PSD-95 inhibitor according to the first or second embodiment of the present invention into pharmaceutical compositions is well known in the art, and is further described in Gennaro (ed.), 2000, Remington: The Science and Practice of Pharmacy, 20th ed., Lippincott, Williams & Wilkins (2000); and Ansel et al., 1999, Pharmaceutical Dosage Forms and Drug Delivery Systems, 7th ed., Lippincott Williams & Wilkins Publishers.

Such a composition typically contains from about 0.1 to 90% by weight (such as about 1 to 20% or about 1 to 10%) of an NMDAR/PSD-95 inhibitor of the invention in a pharmaceutically accepted carrier.

Various liquid and powder formulations can be prepared by conventional methods for inhalation into the lungs of the mammal to be treated.

Compositions suitable for oral administration can be formulated by combining an NMDAR/PSD-95 inhibitor of the invention with a suitable carrier as a tablet, pill, dragee, capsule, liquid, gel, syrup, slurry, suspension for oral ingestions by the subject to be treated. For solid oral/rectal formulations, suitable excipients include fillers such as sugars (e.g. lactose, sucrose, mannitol and sorbitol); cellulose preparations (e.g. maize starch, wheat starch, rice starch, potato starch, gelatin, gum tragacanth, methyl cellulose, hydroxypropylmethyl-cellulose, sodium carboxymethylcellulose, and/or polyvinylpyrrolidine; granulating agents; and binding agents. Optionally, disintegrating agents may be included, such as cross-linked polyvinylpyrrolidine, agar, or alginic acid or a salt of sodium alginate. The solid formulation may further include an enteric-coating.

For liquid oral formulations, suitable excipients or diluents include water, glycols, oils and alcohols.

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water-soluble versions of the compounds can be administered by the drip method, whereby a pharmaceutical formulation containing the active agent (NMDAR/PSD-95 inhibitor) and a physiologically acceptable excipient is infused. Physiologically acceptable excipients can include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as Water-for-Injection, 0.9% saline, or 5% glucose solution. A suitable insoluble form of the compound can be prepared and administered as a suspension in an aqueous base or a pharmaceutically acceptable oil base, such as an ester of a long chain fatty acid (e.g., ethyl oleate).

An NMDAR/PSD-95 inhibitor of the invention may also be formulated as a long acting depot preparation. For example, the inhibitor may be formulated with suitable polymeric or hydrophobic materials (e.g. an emulsion of an acceptable oil) or ion exchange resin, or as a sparingly soluble derivative, such as a sparingly soluble salt.

Liposomes and emulsions may also be used to deliver the NMDAR/PSD-95 inhibitor. Additionally, the NMDAR/PSD-95 inhibitor may be delivered via a sustained release system, such as semi-permeable matrices of solid polymers comprising the inhibitor.

The optimal percentage of the therapeutic agent in each pharmaceutical formulation varies according to the formulation itself and the therapeutic effect desired in the specific pathologies and correlated therapeutic regimens.

VIII. Mode of Administration of a Pharmaceutical Composition Comprising an NMDAR/PSD-95 Inhibitor According to the First or Second Embodiment of the Invention Conventional methods, known to those of ordinary skill in the art of medicine, can be used to administer compositions to the subject or patient, and may be supplied for use in the form of a kit. These include but are not limited to subcutaneous, intrapulmonary, transmucosal, intraperitoneal, intrauterine, sublingual, intrathecal, or intramuscular routes, by using standard methods/means for delivery [including by injection, catheter, where the kit may include an injection devise, a devise for delivering an injectable depot, or a catheter]. In addition, the pharmaceutical formulations can be administered to the patient via injectable depot routes of administration such as by using 1-, 3-, or 6-month depot injectable or biodegradable materials and methods.

Regardless of the route of administration, an NMDAR/PSD-95 inhibitor of the present invention is typically administered at a daily dosage of about 0.01 mg to about 30 mg/kg of body weight of the patient (e.g., 1 mg/kg to 5 mg/kg). The pharmaceutical formulation can be administered in multiple doses per day, if desired, to achieve the total desired daily dose.

Conventional methods, known to those of ordinary skill in the art of medicine, can be used to administer the pharmaceutical formulation(s) of the present invention to the patient. The pharmaceutical compositions of the present invention can be administered alone, or in combination with other therapeutic agents or interventions. Specifically, the compositions of the present invention may further comprise a plurality of agents of the present invention.

Examples

Methodology
Chemical Analysis:

Proton ($^1$H) NMR spectra were recorded on Bruker spectrometers: Avance 300 NMR (300 MHz). Chemical shifts (δ) are reported in parts per million (ppm) with reference to tetramethylsilane (TMS) as internal standard. NMR experiments were carried out in $CD_3OD$. The following abbreviations are used for the proton spectra multiplicities: s, singlet; d, doublet; dd, double doublet, triplet; q, quartet; m, multiplet. Coupling constants (J) are reported in Hertz (Hz). Mass spectra were obtained with an Agilent 6410 Triple Quadrupole Mass Spectrometer instrument using electron spray (ESI-MS) coupled to an Agilent 1200 HPLC system with autosampler and diode-array detector using a linear gradient of the binary solvent system of water/acetonitrile/TFA (A: 95/5/0.1 and B: 5/95/0.086) with a flow rate of 1 mL/min. During ESI-MS analysis evaporative light scattering (ELS) traces were obtained with a Sedere Sedex 85 Light Scattering Detector, which were used for estimation of the purity of the final products. High resolution mass spectra (HRMS) were obtained using a Q-TofT 2 instrument and were all within ±5 ppm of theoretical values. Preparative HPLC was performed on a Agilent 1100 system using a C18 reverse phase column (Zorbax 300 SB-C18, 21.2×250 mm) with a linear gradient of the binary solvent system of water/acetonitrile/TFA (A: 95/5/0.1 and B: 5/95/0.086) with a flow rate of 20 mL/min and UV detection at 230 nm.

Expression and Purification of PDZ1, PDZ2, PDZ3 and PDZ1-2 of PSD-95:

The cDNA coding for PSD-95 PDZ1 (residues 61-151), PDZ2 (residues 155-249), PDZ3 (residues 309-401) and PDZ1-2 (residues 61-249) tandem were amplified by inverted PCR and cloned in modified His-tagged pRSET vector (Invitrogen, Carlsbad, Calif., USA) (numbers in parenthesis refer to the residue numbers in the human full-length PSD95α without exon 4b). All PDZ constructs contained an extra sequence, MHHHHHPRGS (SEQ ID NO: 39), which was used as a tag for purification (His-tag), and the DNA coding sequences and encoded proteins are designated as follows:

HIS-PDZ1 DNA [SEQ ID NO: 1] encoding HIS-PDZ1 protein [SEQ ID NO: 2]

HIS-PDZ2 DNA [SEQ ID NO: 3] encoding HIS-PDZ2 protein [SEQ ID NO: 4]

HIS-PDZ3 DNA [SEQ ID NO: 5] encoding HIS-PDZ3 protein [SEQ ID NO: 6]

HIS-PDZ1-2 DNA [SEQ ID NO: 7] encoding HIS-PDZ1-2 protein [SEQ ID NO: 8]

Competent *E. coli* bacteria (BL21-DE3, pLysS) were transformed with PDZ expressing constructs and grown overnight on agar plates containing ampicillin (100 µg/mL) and chloramphenicol (35 µg/mL) at 37° C. Colonies were picked and used to inoculate bacterial cultures (LB medium with 50 µg/mL ampicillin). These were stirred while being incubated at 37° C. until $A_{600}$ reached 0.95 for PDZ1, PDZ2, and PDZ3 or 0.45 for PDZ1-2, at which point 1 mM isopropyl β-D-1-thiogalactopyranoside was added. Induced cultures were incubated for 4 hours at 37° C. (PDZ1, 2, 3) or over night at 30° C. (PDZ1-2). Cells were harvested by spinning at 10 000 g for 10 min at 4° C. and re-suspension in lysis buffer (50 mM Tris/HCL pH 7.5, 1 mM PMSF, 25 µg/ml DNAse, 40 mM $Mg_2SO_4$). The cells were destroyed using a cell disruptor apparatus at 26 KPsi. The cell lysate was spun down at 35 000 g for 1 hour and the supernatant filtered with a 0.45 am and a 0.22 am filter. Purification was performed by first a nickel (II)-charged column (HisTrap™ HP, GE Healthcare, UK) equilibrated with Tris-buffer (Tris/HCl buffer 50 mM, pH 7.5) followed by anion-exchange chromatography for PDZ1 and 3 and gel-filtration for PDZ2 and 1-2. For anion-exchange chromatography, a MonoQ HR 5/5 column (GE Healthcare, UK) equilibrated with 50 mM Tris/HCL, pH 8.5 was used and elution was done with a gradient of 0-500 mM NaCl. For gel-filtration the PDZ sample was loaded on a Superdex™ 75 HR 10/30 column (GE Healthcare, UK) equilibrated with Tris buffer (20 mM Tris/HCL, pH 7.5) with a constant flow rate at 0.5 mL/min. The relevant fractions were analyzed on a SDS-PAGE gel stained by a standard silver staining protocol. The final purification was analyzed by electrospray ionization liquid chromatography-mass spectrometry (ESI-LC/MS) to get the exact molecular weight and thereby verify the identity of the PDZ domain. Molar extinction coefficients were found by amino acids analysis (Alphalyse, Odense, Denmark) and thereafter used for measuring protein concentrations. For Pull-down experiments, PDZ2 without His-tag was produced, to act a "prey". For this a slightly different construct was used that allowed the His-tag to be enzymatically cleaved off by bovine Thrombin (1 unit per 100 µg protein; Incubation over night at room temperature while rotating), followed by purification using "reverse purification" on the HisTrap™ HP column under the same condition as previously described.

Peptide Synthesis:

Peptides were manually synthesized by Fmoc-based solid-phase peptide synthesis (SPPS) using a MiniBlock™ (Mettler-Toledo, Columbus, Ohio, USA). Peptides with C-terminal Val or Ala were synthesized from pre-loaded Wang resins (Novabiochem, Darmstadt, Germany). For peptides with an unnatural amino acid in the C-terminal a 2-chloro-trityl resin was used and the first amino acid was loaded on the resin using diisopropylethylamine (DIPEA) (resin/amino acid/DIPEA in 1:4:8) in DCM for 30 min., followed by capping with methanol (DCM/MeOH/DIPEA 17:2:1). Fmoc deprotection was performed with 20% piperidine in DMF (2×10 min) and coupling of the consecutive amino acid was carried out with O-(benzotriazol-1-yl)-N,N,N',N'-tetramethyluronium hexafluorophosphate (HBTU) and DIPEA (resin/amino acid/HBTU/DIPEA 1:4:4:4) and monitored by the ninhydrin test. The final peptide was cleaved from the resin by treatment with 5% water and 5% triisopropylsilane (TIPS) in trifluoracetic acid (TFA) for 2 h. The crude peptide was purified by preparative HPLC to >98% purity. The peptide was analyzed by ESI-LC/MS and lyophilized. Quantification of the synthesized peptides was performed by weighing the peptide product. Key peptides (NR2B WT [1], 5-FAM-NR2B and Tat-NR2B [3]) were analyzed by amino acid analysis (Alphalyse, Odense, Denmark) and the molar extinction coefficients were thereby determined. The 5-FAM (Anaspec, San Jose, Calif., USA) was attached to the peptides by coupling with O-(7-azabenzotriazol-1-yl)-N,N,N',N'-tetramethyluronium hexafluorophosphate (HATU). Similarly, N-methylated amino acids and the amino acid following the N-methylated amino acid were coupled to the growing peptide using HATU. Cy5 conjugated NR2B (Cy5-NR2B) was synthesized by coupling Cy5-maleimide (GE Healthcare, UK) to the cysteine side chain of the peptide sequence CSG-YEKLSSIESDV (SEQ ID NO: 34) in solution followed by HPLC purification and ESI-LC/MS analysis. The reaction was performed in a 1:1 ratio between peptide and Cy5-maleimide in 1×TBS buffer for 2 hours at room temperature. Quantification of Cy5-peptides was achieved by measuring absorbance using the molar extinction coefficient of Cy5. Two fluorescent PDZ3 binding peptides, based on the CRIPT sequence (KSG/CSG-LDTKNYKQTSV (SEQ ID NO: 37)),[9] were synthesized with 5-FAM and Cy5, respectively, as described above for NR2B. N-terminal acetylated peptides were synthesized by treating the deprotected peptide with acetic anhydride in DIPEA and DMF (1:2:3) for 1 hour followed by TFA cleavage, purification, and characterization as described above.

N-Terminal Alkylation of Peptides—General Procedure:

Peptide (0.25 mmol, 1 equiv) was synthesized on a 2-chloro-trityl resin as described above followed by Fmoc-deprotection, washing and drying of the resin. The resin was swelled in DIPEA (6 equiv) in THF (2.5 mL) and 2-nitrobenzenesulfonyl chloride (4 equiv) in $CH_2Cl_2$ (1 mL) was added slowly while agitating the solution. After shaking at room temperature for 3 h the resin was drained and washed with THF, MeOH, DCM, and THF (flow washes for 2 min.). Subsequently, the resin was treated with triphenylphosphine ($Ph_3P$, 2 M in THF, 5 equiv) and the alcohol (ROH, 10 equiv) in dry THF (1.0 mL) under nitrogen. DIAD (1 M in THF, 5 equiv) was introduced slowly followed by agitation for 1 h at room temperature. The resin was then drained and washed with THF and DCM (flow washes). The resin-bound alkylated sulfonamide was swelled in 2 mL DMF and treated with NaSPh/DMF solution (1 M, 2 mL) for 1 h. This was repeated four times to ascertain full deprotection, after which the resin was washed and the modified peptide cleaved from the resin, purified, and characterized as described previously.

N-Methyl-ETAV (SEQ ID NO: 40) (40).

Yield: 80%. ESI-LC/MS: >99% (ELSD), 98% (UV). 1H NMR ($CD_3OD$) δ (ppm): 4.47 (q, J=7.2, 1H), 4.44 (d, J=4.8, 1H), 4.30 (d, J=5.6, 1H), 4.18-4.14 (m, 1H), 3.97 (dd, J=7.2, 5.6 Hz, 1H), 2.68 (s, 3H), 2.53 (t, J=7.4, 2H), 2.19-2.14 (m, 3H), 1.39 (d, J=7.2, 3H), 1.23 (d, J=6.4, 3H), 0.97 (d, J=6.6, 6H). HRMS (ES+) calcd for $C_{18}H_{33}N_4O_8$ $[M+H]^+$, 433.2298. found, m/z 433.2315.

N-Ethyl-ETAV (SEQ ID NO: 40) (52).

Yield: 71%. ESI-LC/MS: >99% (ELSD), >99% (UV). $^1$H NMR (CD$_3$OD) δ (ppm): 4.47 (q, J=6.8, 1H), 4.44 (d, J=5.2, 1H), 4.30 (d, J=6.0, 1H), 4.17-4.13 (m, 1H), 4.03 (dd, J=7.6, 5.2 Hz, 1H), 3.06-3.03 (m, 2H), 2.53 (t, J=7.4, 2H), 2.19-2.13 (m, 3H), 1.38 (d, J=7.2, 3H), 1.32 (t, J=7.4, 3H), 1.22 (d, J=6.4, 3H), 0.97 (d, J=6.8, 6H). HRMS (ESI+) calcd for $C_{19}H_{35}N_4O_8$ $[M+Na]^+$, 469.2274. found, m/z 469.2280.

N-Propyl-ETAV (SEQ ID NO: 40) (53).

Yield: 95%. ESI-LC/MS: >99% (ELSD), >99% (UV). $^1$H NMR (CD$_3$OD) δ (ppm): 4.47 (q, J=6.8, 1H), 4.44 (d, J=5.2, 1H), 4.30 (d, J=5.2, 1H), 4.17-4.14 (m, 1H), 4.02 (dd, J=7.6, 5.2 Hz, 1H), 2.98-2.88 (m, 2H), 2.54 (t, J=7.4, 2H), 2.21-2.12 (m, 3H), 1.76-1.70 (m, 2H), 1.38 (d, J=7.2, 3H), 1.22 (d, J=6.4, 3H), 1.0 (t, J=7.4, 3H), 0.97 (d, J=6.8, 6H). HRMS (ESI+) calcd for $C_{20}H_{37}N_4O_8$ $[M+H]^+$, 461.2611. found, m/z 461.2624.

N-Butyl-ETAV (SEQ ID NO: 40) (54).

Yield: 94%. ESI-LC/MS: >99% (ELSD), >99% (UV). $^1$H NMR (CD$_3$OD) δ (ppm): 4.47 (q, J=7.2, 1H), 4.44 (d, J=5.2, 1H), 4.30 (d, J=5.6, 1H), 4.17-4.14 (m, 1H), 4.02 (dd, J=7.2, 5.2 Hz, 1H), 3.00-2.93 (m, 2H), 2.54 (t, J=7.4, 2H), 2.21-2.12 (m, 3H), 1.70-1.65 (m, 2H), 1.45-1.40 (m, 2H), 1.38 (d, J=7.2, 3H), 1.22 (d, J=6.4, 3H), 1.0 (t, J=7.4, 3H), 0.97 (d, J=6.8, 6H). HRMS (ESI+) calcd for $C_{21}H_{39}N_4O_8$ $[M+H]^+$, 475.2768. found, m/z 475.2770.

N-Cyclohexylmethyl-ETAV (SEQ ID NO: 40) (55).

Yield: 8%. ESI-LC/MS: >99% (ELSD), >99% (UV). $^1$H NMR (CD$_3$OD) δ (ppm): 4.45 (q, J=7.2, 1H), 4.41 (d, J=4.8, 1H), 4.28 (d, J=5.4, 1H), 4.17-4.12 (m, 1H), 3.94 (dd, J=7.2, 5.6 Hz, 1H), 2.82 (d, J=6.6, 1H), 2.76 (d, J=7.2, 1H), 2.56 (t, J=7.4, 2H), 2.18-2.12 (m, 3H), 1.86-1.68 (m, 6H), 1.38 (d, J=7.2, 3H), 1.32-1.25 and 1.08-1.01 (m, 5H), 1.22 (d, J=6.0, 3H), 0.96 (d, J=6.6, 6H). HRMS (ESI+) calcd for $C_{24}H_{43}N_4O_8[M+H]^+$, 515.3081. found, m/z 515.3091.

N-Cyclohexylethyl-ETAV (SEQ ID NO: 40) (56).

Yield: 56%. ESI-LC/MS: >99% (ELSD), >99% (UV). $^1$H NMR (CD$_3$OD) δ (ppm): 4.45 (q, J=7.2, 1H), 4.42 (d, J=4.8, 1H), 4.29 (d, J=5.4, 1H), 4.16-4.12 (m, 1H), 3.99 (dd, J=7.2, 5.4 Hz, 1H), 3.03-2.91 (m, 2H), 2.53 (t, J=7.4, 2H), 2.22-2.06 (m, 3H), 1.76-1.66 and 1.32-1.25 (m, 10H), 1.58 (q, J=7.2, 1H), 1.38 (d, J=7.2, 3H), 1.22 (d, J=6.3, 3H), 0.97 (d, J=6.9, 6H). HRMS (ESI+) calcd for $C_{25}H_{45}N_4O_8$ $[M+H]^+$, 529.3237. found, m/z 529.3214.

N-Benzyl-ETAV (SEQ ID NO: 40) (58).

Yield: 66%. ESI-LC/MS: >99% (ELSD), 97% (UV). $^1$H NMR (CD$_3$OD) δ (ppm): 7.49-7.41 (m, 5H), 4.48 (q, J=7.2, 1H), 4.44 (d, J=4.8, 1H), 4.28 (d, J=5.4, 1H), 4.16 (s, 2H), 4.12-4.01 (m, 2H), 2.54 (t, J=6.9, 2H), 2.22-2.11 (m, 3H), 1.38 (d, J=7.2, 3H), 1.24 (d, J=6.3, 3H), 0.97 (d, J=6.6, 6H). HRMS (ESI+) calcd for $C_{24}H_{37}N_4O_8$ $[M+H]^+$, 509.2611. found, m/z 509.2595.

N-Phenylethyl-ETAV (SEQ ID NO: 40) (59).

Yield: 11%. ESI-LC/MS: 98% (ELSD), 98% (UV). $^1$H NMR (CD$_3$OD) δ (ppm): 7.35-7.23 (m, 5H), 4.45 (q, J=6.9, 1H), 4.42 (d, J=4.8, 1H), 4.28 (d, J=5.4, 1H), 4.13-4.09 (m, 1H), 4.05 (dd, J=7.2, 5.1 Hz, 1H), 3.23-3.15 (m, 2H), 3.00 (t, J=7.8, 2H), 2.54 (t, J=7.2, 2H), 2.22-2.12 (m, 3H), 1.38 (d, J=7.2, 3H), 1.20 (d, J=6.3, 3H), 0.96 (d, J=6.9, 6H). HRMS (ESI+) calcd for $C_{25}H_{39}N_4O_8$ $[M+H]^+$, 523.2768. found, m/z 523.2787.

N-Phenylpropyl-ETAV (SEQ ID NO: 40) (60).

Yield: 30%. ESI-LC/MS: 98% (ELSD), 97% (UV). 1H NMR (CD$_3$OD) δ (ppm): 7.48 (d, J=8.1, 1H), 7.46 (d, J=1.2, 1H), 7.20 (dd, J=8.4, 2.1, 1H), 4.45 (q, J=6.9, 1H), 4.41 (d, J=5.1, 1H), 4.28 (d, J=5.4, 1H), 4.15-4.09 (m, 1H), 4.05 (dd, J=7.2, 5.4 Hz, 1H), 3.27-3.13 (m, 2H), 2.99 (t, J=7.8, 2H), 2.54 (t, J=7.2, 2H), 2.22-2.09 (m, 3H), 1.38 (d, J=7.5, 3H), 1.21 (d, J=6.6, 3H), 0.96 (d, J=6.6, 6H). HRMS (ESI+) calcd for $C_{26}H_{41}N_4O_8[M+H]^+$, 537.2924. found, m/z 537.2928.

N-(3,4-Dichlorophenyl)propyl-ETAV (SEQ ID NO: 40) (61).

Yield: 20%. ESI-LC/MS: 98% (ELSD), 97% (UV). $^1$H NMR (CD$_3$OD) δ (ppm): 7.26-7.17 (m, 2H), 7.09-7.04 (m, 1H), 4.45 (q, J=6.9, 1H), 4.41 (d, J=5.1, 1H), 4.28 (d, J=5.4, 1H), 4.15-4.09 (m, 1H), 4.05 (dd, J=7.2, 5.4 Hz, 1H), 3.27-3.13 (m, 2H), 2.99 (t, J=7.8, 2H), 2.54 (t, J=7.2, 2H), 2.22-2.09 (m, 3H), 1.38 (d, J=7.5, 3H), 1.21 (d, J=6.6, 3H), 0.96 (d, J=6.6, 6H). HRMS (ESI+) calcd for $C_{25}H_{37}Cl_2N_4O_8$ $[M+H]^+$, 591.1988. found, m/z 591.1967.

N-(3,4-Difluorophenyl)propyl-ETAV (SEQ ID NO: 40) (62).

Yield: 12%. ESI-LC/MS: 98% (ELSD), 98% (UV). $^1$H NMR (CD$_3$OD) δ (ppm): 7.85-7.79 (m, 3H), 7.74-7.72 (m, 1H), 7.47-7.44 (m, 3H), 7.37 (dd, J=8.7, 1.8, 1H), 4.45 (q, J=6.9, 1H), 4.42 (d, J=4.8, 1H), 4.28 (d, J=5.4, 1H), 4.13-4.06 (m, 2H), 3.34-3.14 (m, 4H), 2.545 (t, J=7.5, 2H), 2.21-2.15 (m, 3H), 1.38 (d, J=7.2, 3H), 1.19 (d, J=6.3, 3H), 0.96 (d, J=6.9, 6H). HRMS (ESI+) calcd for $C_{25}H_{37}F_2N_4O_8$ $[M+H]^+$, 559.2579. found, m/z 559.2591.

N-(Naphtalene-2-yl)ethyl-ETAV (SEQ ID NO: 40) (63).

Yield: 49%. ESI-LC/MS: >99% (ELSD), >99% (UV). $^1$H NMR (CD$_3$OD) δ (ppm): 7.29-7.15 (m, 5H), 4.45 (q, J=6.9, 1H), 4.40 (d, J=4.8, 1H), 4.28 (d, J=5.4, 1H), 4.14-4.10 (m, 1H), 3.99 (dd, J=7.2, 5.1 Hz, 1H), 2.96-2.91 (m, 2H), 2.70 (t, J=7.2, 2H), 2.52 (t, J=7.2, 2H), 2.19-2.08 (m, 3H), 2.06-1.98 (m, 2H), 1.38 (d, J=7.2, 3H), 1.17 (d, J=6.6, 3H), 0.96 (d, J=6.9, 6H). HRMS (ESI+) calcd for $C_{29}H_{41}N_4O_8$ $[M+H]^+$, 573.2898. found, m/z 573.2897.

Synthesis of Dimeric Ligands. General Procedure 1 ("Pfp-Method"):

HOOC-PEG(12)-COOH (PEG12 diacid, Iris Biotechnology, Germany) (0.691 g, 1 mmol) was dissolved in ethyl acetate (100 mL) at 0° C. by vigorously stirring for 25 min. Pentafluorophenol (pfp) (0.368 g, 2 mmol) and N,N-dicyclohexylcarbodiimide (DCC) (0.413 g, 2 mmol) was added and the reaction mixture was stirred for 2 h at 0° C. The mixture was filtered and the filtrate evaporated in vacuo. The resulting Pfp$_2$-PEG-diester was used without further purification. Peptides were synthesized as previously described The Pfp$_2$-PEG-diester (0.125 mmol) and HOBt (0.625 mmol) was added to the resin-bound peptide (0.25 mmol) in 5 portions each dissolved in dry DMF (4 mL) over five days The resin was drained and washed with DMF prior to coupling the next portion. The dimeric peptide was cleaved off the resin with TFA/H$_2$O/TIPS (90/5/5) at rt for 2 h. After removal of solvents in vacuo the dimeric peptide was purified by preparative HPLC and characterized by LC/MS.

Synthesis of Dimeric Ligands. General Procedure 2 ("HBTU-Method"):

PEG-diacid (0.1 eq.) is pre-activated with HBTU (0.2 eq) and DIPEA (0.4 eq) and added to the peptide-resin (1 eq, 0.25 mmol) in DMF (2 mL), and incubated for 45 min. This step is repeated five times, and the resin is washed in between with DMF. The dimeric peptide is cleaved off the resin by treatment with TFA/H$_2$O/TIPS (90/5/5) at room temperature for 2 h. After removal of solvents in vacuo, the dimeric peptide is purified by preparative HPLC and characterized by LC/MS.

(IESDV)₂PEG12 (SEQ ID NO: 33) (74).

Pentapeptide, IESDV (SEQ ID NO: 33), was synthesized as described above and 74 was generated by using the general protocol for dimerizations (using the "Pfp-method"). Yield: 40%. ESI-LC/MS: >99% (ELSD), 98% (UV). MS (ESI+) calcd for $C_{76}H_{133}N_{10}O_{37}$ [M+H]$^+$, 1778.9. found, m/z 1779.

(GE[N-Cyclohexylethyl]TDV)₂PEG12 (SEQ ID NO: 42) (75).

Tetrapeptide ETDV (SEQ ID NO: 41) was synthesized and N-alkylated with cyclohexylethyl as described in the general procedure of N-terminal alkylation of peptides. Gly was then added to the sequence and dimerization was conducted by using the general protocol (using the "Pfp-method"). Yield: 18%. ESI-LC/MS: 99% (ELSD), 94% (UV). MS (ESI+) calcd for $C_{86}H_{149}N_{10}O_{37}$ [M+H]$^+$, 1915.2. found, m/z 1915.

(IESDV)₂PEG8 (SEQ ID NO: 33) (76).

Pentapeptide, IESDV (SEQ ID NO: 33), was synthesized as described above and 76 was generated by using the general protocol for dimerizations (using the "HBTU-method"). Yield: 23%. ESI-LC/MS: >99% (ELSD), 98% (UV). MS (ESI+) calcd for $C_{68}H_{117}N_{10}O_{33}$ [M+H]$^+$, 1601.7. found, m/z 1602.

(IESDV)₂PEG6 (SEQ ID NO: 33) (77).

Pentapeptide, IESDV (SEQ ID NO: 33), was synthesized as described above and 77 was generated by using the general protocol for dimerizations (using the "HBTU-method"). Yield: 23%. ESI-LC/MS: >99% (ELSD), 99% (UV). MS (ESI+) calcd for $C_{64}H_{109}N_{10}O_{31}$ [M+H]$^+$, 1513.7. found, m/z 1514.

(IESDV)₂PEG4 (SEQ ID NO: 33) (78).

Pentapeptide, IESDV (SEQ ID NO: 33), was synthesized as described above and 78 was generated by using the general protocol for dimerizations (using the "HBTU-method"). Yield: 24%. ESI-LC/MS: 98% (ELSD), 98% (UV). MS (ESI+) calcd for $C_{60}H_{101}N_{10}O_{29}$ [M+H]$^+$, 1425.7. found, m/z 1426.

(IETAV)₂PEG4 (SEQ ID NO: 36) (83).

Pentapeptide, IESDV (SEQ ID NO: 33), was synthesized as described above and 83 was generated by using the general protocol for dimerizations (using the "HBTU-method"). Yield: 35%. ESI-LC/MS: >99% (ELSD), 99% (UV). MS (ESI+) calcd for $C_{60}H_{104}N_{10}O_{25}$ [M+H]$^+$, 1365.6. found, m/z 1366.

Fluorescence Polarization (FP) Assay:

PDZ saturation binding assays were used to measure the binding affinity between the fluorescent peptides (Cy5-NR2B, 5-FAM-NR2B, Cy5-CRIPT or 5-FAM-CRIPT). To a fixed concentration of Cy5-NR2B, 5-FAM-NR2B, Cy5-CRIPT or 5-FAM-CRIPT (50 nM) increasing concentrations of PDZ was added to get a saturation binding curve. The assay was performed in a 1×TBS buffer (150 mM NaCl, 10 mM Tris, pH 7.4) including 1% BSA in black flat bottom 384-well plates (Corning Life Sciences, NY, USA). After incubation for 20-30 mins at rt, the FP of the samples was measured on a Safire² plate-reader (Tecan, Männedorf, Switzerland), but before reading the samples the g-factor was adjusted such that 50 nM probe without any PDZ present would give a FP value of 20 mP. Cy5-NR2B and Cy5-CRIP, as well as 5-FAM-NR2B and 5-FAM-CRIPT were measured at excitation/emission values of 635/670 nm and 470/525 nm, respectively. The FP values were fitted to the equation $Y=B_{max}*X/(K_d+X)$, where $B_{max}$ is the maximal FP value, X is the PDZ concentration, and Y is variable FP values. As long as the concentration of labeled peptide is well below the true $K_d$ during the assay, the $K_d$ can be directly derived from this saturation curve as being equal to the PDZ concentration where the curve is half saturated (at these conditions $EC_{50}$=[total PDZ]$_{half\ saturation}$=[free PDZ]$_{half\ saturation}$≡$K_d$).[5]

To measure the affinities between non-fluorescent peptides and PDZ domains, heterologous competition bindings assay were performed. This was done by adding increasing concentrations of peptide to a fixed concentration of Cy5-NR2B, 5-FAM-NR2B, Cy5-CRIPT or 5-FAM-CRIPT (50 nM) and PDZ (20 μM for PDZ1, 3 μM for PDZ2 and 1-2 and 5 μM for PDZ3) in the same TBS buffer and conditions as described above. FP values were then fitted to the general equation: $Y=Bottom+(Top-Bottom)/[1+(10^{X-log\ IC50})]$, where X is the logarithmic value of peptide concentration. Hereby the $IC_{50}$ value was obtained, which is used to calculate the theoretical competitive inhibition constant, $K_i$.[5]

Stopped-Flow Fluorimetry:

The HIS-PDZ2 and HIS-PDZ1-2 expression constructs of PSD-95 were genetically manipulated to encode a tryptophan, (in position 51 of SEQ ID NO: 4 and position 145 in SEQ ID NO: 8, respectively) instead of isoleucine. Binding between PDZ2 and PDZ1-2 and peptide ligand 74 was then monitored and quantified, by measuring the fluorescence increase from this tryptophan upon ligand recognition. (excitation λ at 280 nm, emission λ>320 nm). Stopped-flow measurements were performed at 10° C. or 25° C. on an SX-20MV stopped-flow spectrometer (Applied Photophysics, Leatherhead, UK). The peptide, in varying amounts, was rapidly mixed with a constant amount of PDZ and the change in fluorescence was measured over time. The fluorescence versus time plots was fitted to a single or double exponential equation, from which one or two observed rate constants were obtained. Observed rate constants were then plotted against the concentration of the varied species and microscopic rate constants determined by fitting the data to the equation for a bimolecular association (Eq. 1)

$$k_{obs}=((k_{on}^2(n-[A]_0)^2+k_{off}^2+2k_{on}k_{off}(n+[A]_0))^{0.5} \quad \text{(Eq. 1)}$$

$k_{on}$ is the association rate constant, $k_{off}$ is the dissociation rate constant, and $[A]_0$ and n are the initial concentrations of the varied and constants species, respectively.

To determine $k_{off}$ rates, a chase experiment was conducted. In this experiment, PDZ1-2I195W in complex with 74 was mixed with non-mutated PDZ1-2, whereby 74 was competed out. At high concentrations of non-mutated PDZ1-2, the observed rate constant approaches the net off-rate constant for the binding reaction ($k_{off}^{app}$) between 74 and PDZ1-2. Observed rate constants were fitted to Eq. 2 to estimate the apparent, or net, off-rate constant for the peptide, $k_{off}^{app}$.

$$k_{obs}=k_{off}^{app}+k_{on}'\times K_D/(K_D+[\text{unlabeled peptide}]) \quad \text{(Eq. 2)}$$

The equilibrium dissociation constant $K_d$ of the PDZ-peptide complex was calculated by the experimental determined $k_{on}$ and $k_{off}$.

Pull-Down Assay:

The assay was performed with a ProFound™ Pull-down PolyHis Protein-protein Interaction Kit purchased from Pierce and performed according to the manufacturer's instructions.

Molecular Modeling:

PDZ1 and PDZ2 were aligned with PDZ3 using Prime (Schrödinger, Portland, Oreg., USA). From these sequences homology models were created using the PDZ3 X-ray crystal structure (PDB structure 1BE9)[10] as template in Prime with standard parameters. The peptide ligand from 1BE9, KQTSV (SEQ ID NO: 43), was rebuilt to IESDV (SEQ ID NO: 33) in the homology models. The side chains of the PDZ domain and the peptide were then minimized in Macromodel (Schrödinger, Portland, Oreg., USA) using the force field OPLS2005 and by constraining the backbone. A grid around the peptide was generated in Glide (Schrödinger, Portland, Oreg., USA) and used for docking. Relevant peptides were docked flexibly in Glide using default parameters, and the best scoring poses were energy minimized. The conserved water molecule seen in the binding pocket was kept constant during docking and minimization. Pymol, version 0.97, was used for creating figures.[11]

Isothermal Titration Calorimetry (ITC):

Calorimetry experiments were performed on a microcalorimeter (Microcal, MA, USA). The ligands were titrated directly into the PDZ solution. All ligands and PDZ proteins were solubilized in PBS buffer (137 mM NaCl, 2.7 mM KCl, 10 mM $Na_2HPO_4$, 2 mM $KH_2PO_4$, pH 7.4) and when necessary pH was adjusted to 7.4 within 0.02 pH units after solubilization. The concentration of peptide and PDZ in solution was quantified by amino acid analysis. The calorimetry experiments were conducted at 25° C., where the PDZ1-2 concentration was generally adjusted to about 20 µM (200 µL in calorimeter) and the ligand concentration to between 200-2500 µM (injected to the protein as 20×2 µL). Experiments were designed so that c-value (c-value=$K_a$* [Protein]*n; where $K_a$ is the affinity association constant, [Protein] means protein concentration, and n is the stoichiometry of the reaction) was within 1-1000. The analysed solution was stirred at 1000 rpm, with a reference power of 6 µcal/s. Heats of dilution were initially determined by titrating the ligand into buffer and subtracting these baseline values from the observed "heat values". The data from each titration experiment were collected by ORIGIN 7.0 (Microcal, MA, USA), which was also used to determine the thermodynamic properties of ligand binding using non-linear least-squares fitting assuming a single-site model.

Human Blood Plasma Stability Assay.

Compounds of interest were dissolved in human blood plasma (270 µl; 3H Biomedical, Sweden, cat no 1300-1-P50) to a concentration of 0.25 mM (30 µL of 2.5 mM) and incubated at 37° C. Aliquots (30 µl) were removed at various time intervals (0, 5, 10, 20, 40, 80, 160, 320, 960, 1280, 2550, 4560 and 7240 min) and quenched with 60 µL trichloroacetic acid (aq., 5%). The aliquots were vortexed, and incubated for at least 15 min, at 4° C. prior to centrifugation at 18,000 g for 2 min and the supernatant was analyzed by RP-HPLC to quantify the remaining compound (absorbance at 218 nm). The RP-HPLC analysis was conducted on an Agilent 1100 system using a Zorbax 300 SB-C18 column (5 m, 4.6×150 mm, Agilent Technologies, USA), flow rate of 1 mL/min, and a gradient starting from 100% buffer A (95% water, 5% acetonitrile, 1% TFA) to 40% buffer B (95% acetonitrile, 5% water, 1% TFA) and 60% buffer A over 40 min.

Neuronal Excitotoxicity Assay.

Cortical neurons were surgically removed from rats (e.g. E21) and then cultured for 7-9 days in vitro in Neurobasal A medium with B-27 supplement (each supplied by Invitrogen), further supplemented with 1 mM glutamine, 50 units/ml penicillin, and 50 g/ml streptomycin. The following steps were then performed:

1. Samples of the cultured cortical neurons were removed from the Neurobasal-A based culture medium, at various time points prior to exposure to compound, and placed into "transfection medium" (TH; as defined by Bading et al (1993) Science 260, 181-186) comprising: 10% modified Minimum Essential Medium (supplied by Invitrogen; product no: 21090022; containing Earles salt, but no L-glutamine), 90% Salt-Glucose-Glycine (SGG) medium: (114 mM NaCl, 0.219% $NaHCO_3$, 5.292 mM KCL, 1 mM $MgCl_2$, 2 mM $CaCl_2$, 10 mM HEPES, 1 mM Glycine, 30 mM glucose, 0.5 mM sodium pyruvate, 0.1% Phenol Red), insulin-transferrin-selenite supplement (supplied by Sigma: 7.5 µg insulin/ml, 7.5 µg transferring/ml and 7.5 ng sodium selenite/ml); with a final osmolarity of 325 mosm/l. All subsequent steps were performed in this TM medium.

2. Samples of neurons are exposed to an NMDAR/PSD-95 inhibitor of the invention (compounds 40, 52-90) at a final concentration of between 0.05-50 µM for a period of between 0.5 to 1.5 hours. In control assays, the samples were exposed to NR2B (1), or Tat-NR2B (3) or TM medium alone.

3. Each sample of neurons was washed at least one time in TM medium to remove the NMDAR/PSD-95 inhibitor, and placed in TM medium.

4. After various periods of time, the samples of neurons were exposed to NMDA at a concentration of between 10-100 µM for a period of 0.5 to 1.5 hours, preferably 1 hour, after which the samples were again placed in TM medium for 24 hours.

5. LDH in the cell medium was quantified using commercial available kits (e.g. Promega Biotech AB, cat no G1780).

Example 1. A Fluorescence Polarization Assay for Detecting Interactions Between Peptide Analogues and PDZ Domains A convenient and reliable way to examine interactions between peptide analogues and PDZ domains is by using a fluorescence polarization (FP) assay. The three PDZ domains, PDZ1-3, of PSD-95 were expressed individually as set out above, while PDZ1-2 was also expressed as a tandem construct. As set out above, fluorescent peptides were synthesized by labelling the undecapeptide peptides corresponding to the wild-type (WT) C-terminal of the NR2B subunit (YEKLSSIESDV (SEQ ID NO: 34)) and CRIPT (LDTKNYKQTSV (SEQ ID NO: 37)) with either 5-FAM or Cy5, through a tripeptide (KSG or CSG) linker, at the N-terminus (designated 5-FAM-NR2B, Cy5-NR2B, 5-FAM-CRIPT and Cy5-CRIPT).[12] $K_d$ values were then determined. A competition binding assay was also implemented, to measure the affinity as $IC_{50}$ values between PDZ domains and non-fluorescent NR2B (1, KSG-YEKLSS-IESDV (SEQ ID NO: 34)) and CRIPT (2, KSG-LDT-KNYKQTSV (SEQ ID NO: 37)) peptides. $IC_{50}$ values were then converted to $K_i$ values.[5]

Since $K_d$ and $K_i$ values should be similar when measuring the same PDZ-peptide interaction, these values were compared for the NR2B derived peptides (PDZ1, PDZ2, and PDZ1-2) and CRIPT derived peptides (PDZ3). The $K_d$ and $K_i$ values were found to be very similar when measured against PDZ1, PDZ2 and PDZ3, although the $K_i$ for the tandem construct PDZ1-2 is somewhat higher than $K_d$ (Table 1).

TABLE 1

Validation of FP assay: $K_d$ and $K_i$ values of WT probes and peptides.[a]

| Compound | PDZ1 | PDZ2 | PDZ3 | PDZ1-2 |
|---|---|---|---|---|
| 5-FAM/Cy5-NR2B[b] | 20 ± 1.6 | 3.0 ± 0.16 | NA[d] | 1.7 ± 0.11 |

TABLE 1-continued

Validation of FP assay: $K_d$ and $K_i$ values of WT probes and peptides.[a]

| Compound | PDZ1 | PDZ2 | PDZ3 | PDZ1-2 |
|---|---|---|---|---|
| 5-FAM/Cy5-CRIPT[b] | ND[d] | ND[d] | 3.5 ± 0.18 | ND[d] |
| NR2B (1)[c] | 18 ± 0.92 | 4.1 ± 0.17 | NA[d] | 7.0 ± 0.19 |
| CRIPT (2)[c] | 97 ± 18 | 25 ± 1.6 | 2.1 ± 0.15 | 45 ± 4.1 |
| Tat-NR2B (3)[c] | 14 ± 1.9 | 4.4 ± 0.32 | NA[d] | 9.8 ± 0.35 |

[a]$K_d$ and $K_i$ values are shown as mean ± SEM (standard error of mean) in μM based on at least four individual measurements.
[b]$K_d$ values.
[c]$K_i$ values.
[d]ND: Not determined, NA: No activity.

Furthermore, the $K_d$ values are independent of whether 5-FAM or Cy5 is used as a fluorophore (data not shown). The $K_d$ for 5-Fam-NR2B peptide was also determined for PDZ2 with and without His-tag and, as expected, no difference was observed (data not shown).[13, 14] Thus, the results obtained in the assay represent accurate measurements, consistent with the literature values for similar measurements.[15-17] The NR2B peptide (1) shows no binding to PDZ3 (Table 1), which is expected,[9, 12] hence activity at PDZ3 was used as a measure of selectivity in the examples. All compounds were tested for PDZ3 binding and unless otherwise stated, compounds had no affinity towards this domain.

The 20-mer Tat-NR2B peptide (3, YGRKKRRQRRR-KLSSIESDV (SEQ ID NO: 44)) is reported to have >100-fold increased affinity to PDZ2 compared to the NR2B peptide alone, as shown by a solid-phase ELISA based assay.[3] However, the FP assay reveals, $K_i$ values for PSD-95 PDZ domains are similar for NR2B (1) and Tat-NR2B (3) (Table 1). Thus, the notable in vivo effects demonstrated for this Tat-NR2B peptide[1] are more likely due to the ability of the Tat-moiety to improve membrane permeability of peptides, rather than increasing the affinity between peptide ligand and the PDZ domains of PSD-95.

Figure 2A:
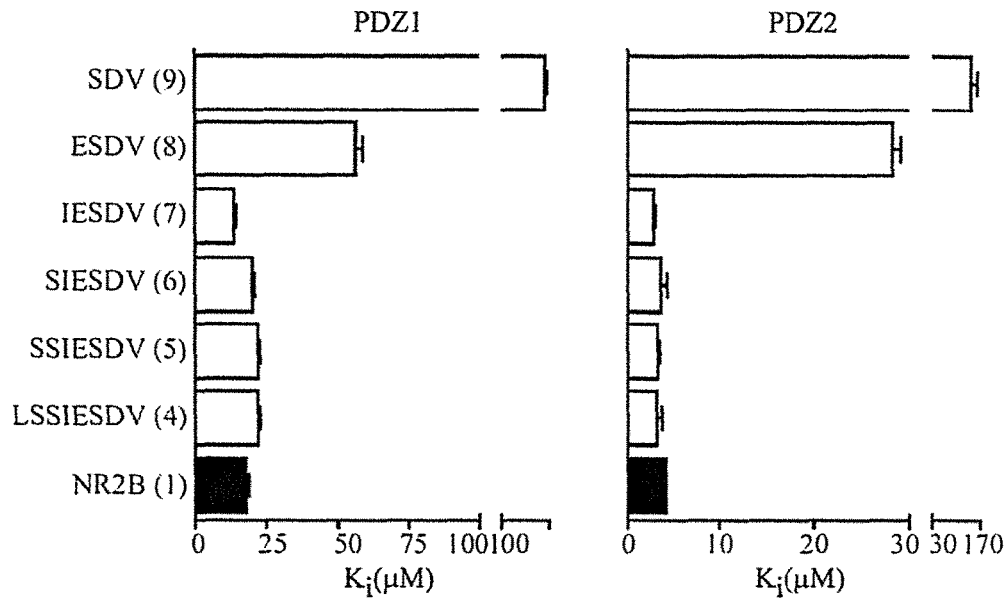
FIG. 2A. $K_i$ values of truncated peptides for the interaction with PDZ1 and PDZ2 where error bars indicate SEM based on at least four individual measurements.

Example 2. Identification of the Essential Features of a NR2B Peptide Required for Binding to PDZ Domains to Obtain an NMDAR/PSD-95 Inhibitor of the Invention The minimal sequence of the NR2B peptide (1) required for binding to PDZ1 and PDZ2 was identified using the FP assay. The NR2B peptide was truncated sequentially from the N-terminus and notably it was possible to reduce it to a pentapeptide, IESDV (SEQ ID NO: 33) (7), without losing affinity (FIG. 2A). Truncation to the tetrapeptide ESDV (SEQ ID NO: 32) (8) showed 3.1 and 6.8 fold increase in $K_i$ values for PDZ1 and PDZ2, respectively, and the tripeptide, SDV, demonstrated >20 and >30 fold increase in $K_i$ compared to peptide 1. In order to examine the generality of this approach to PDZ domain proteins, the activity of the CRIPT peptide (2) at PDZ3 was compared with a truncated CRIPT pentapeptide (KQTSV (SEQ ID NO: 43)); in contrast to the NR2B peptide (1) and PDZ1 and PDZ2, a 14-fold reduction in $K_i$ was observed for this pentapeptide (data not shown).

Figure 2B:
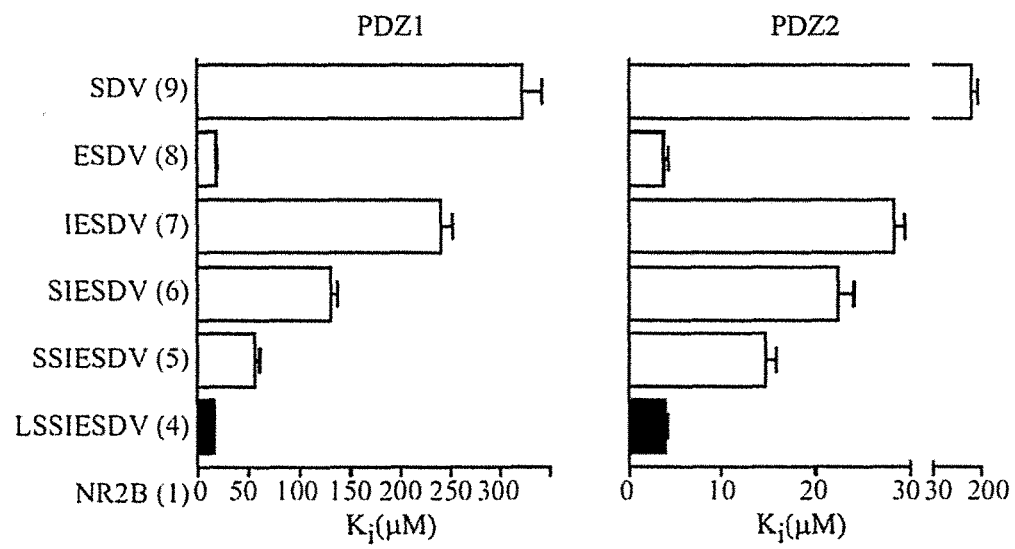
FIG. 2B. $K_i$ values of Ala-scan performed with pentapeptide (7) towards PDZ1 and PDZ2 where error bars indicate SEM based on at least four individual measurements.
Figure 3:
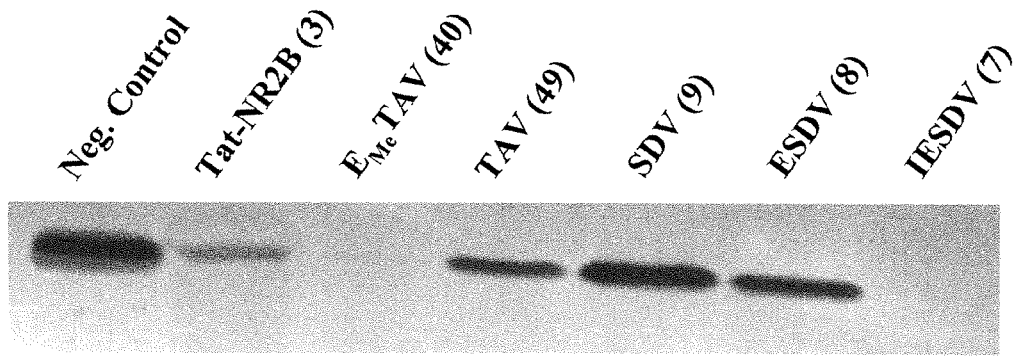
FIG. 3. Silver-stained SDS PAGE gel showing PDZ2 domain peptide bound to an immobilised polyhistidine NR2B WT peptide bait following incubation in the presence or absence of the following peptide analogue inhibitors: Tat-NR2B (3), $E_{Me}TAV$ (SEQ ID NO: 31) (40), TAV (49), SDV (9), ESDV (SEQ ID NO: 32) (8), IESDV (SEQ ID NO: 33) (7) and then recovered from the pull-down assay.

To investigate the individual importance of the five amino acids in the pentapeptide (7) an alanine scan was performed on this peptide (FIG. 2B). For both PDZ1 and PDZ2, almost complete loss of affinity was observed when substituting Val in the $P^0$ position (14), thereby underlining the crucial importance of the isopropyl side chain. A similar effect was observed for PDZ1, when exchanging Ser ($P^{-2}$) (12), while a 7-fold increase in the $K_i$ value was seen for PDZ2. Thus positions $P^0$ and $P^{-2}$ are particularly critical for affinity in the pentapeptide, corresponding to a truncated NR2B peptide (1). Two other positions, Glu ($P^{-3}$) and Ile ($P^{-4}$) displayed less sensitivity to Ala substitutions (10 and 11, respectively), but $K_i$ values were still somewhat higher than 1 towards PDZ1 and PDZ2. On the other hand, replacing Asp ($P^{-1}$) (13) did not affect affinity to PDZ1 or PDZ2, however some activity at PDZ3 appeared. Although the affinity of 13 towards PDZ3 is low ($K_i$>30 fold higher than CRIPT), this suggest that Asp ($P^{-1}$) plays a role in determining selectivity between the PDZ domains of PSD-95.

Example 3. Enhancing the Affinity of Peptide Ligands for PDZ1 and 2 Domains by Single Modifications to Obtain an NMDAR/PSD-95 Inhibitor of the Invention Substitutions in the truncated NR2B peptide ligand were tested to improve the affinity of the ligand, and at the same time reduce its polarity. The tetrapeptide, ESDV (SEQ ID NO: 32) (8) was used as a template, rather than the pentapeptide, because it is a better starting point for development of small molecules, and it is still relatively potent at both PDZ1 and PDZ2. Introduction of D- and N-methyl amino acids can often induce resistance to enzymatic cleavage. Moreover, D-amino acids provide information on the importance of stereochemical arrangement of the side chains of the amino acids, while N-methyl amino acids are known to stabilize certain amide bond conformations.[18]

Introduction of D-Ser, D-Asp and D-Val instead of their respective L-amino acids one at a time into ESDV (SEQ ID NO: 32) (8) abolished affinity to both PDZ1 and PDZ2, whereas D-Glu impaired the affinity >25 times for PDZ1 and PDZ2 relative to peptide 1 (data not shown). Thus, L-amino acids are essential for affinity. Substitution with N-methyl amino acids was better tolerated (Table 2). N-methylation of Asp in $P^{-1}$ (16) showed some loss in affinity compared to the NR2B peptide (1) for both PDZ1 and PDZ2 (Table 2), whereas, N-methylation of Val ($P^0$) (15) and Ser ($P^{-2}$) (17) resulted in inactive peptides. However, substituting the terminal amino acid Glu ($P^{-3}$) with N-methylated Glu (18) improved the affinity relative to the reference tetrapeptide (8) and compared to peptide 1, peptide 18 showed only 1.3 and 3.7-fold higher $K_i$ values for PDZ1 and PDZ2, respectively (Table 2).

TABLE 2

$K_i$ values of N-methylated ESDV (SEQ ID NO: 32) analogues[a]

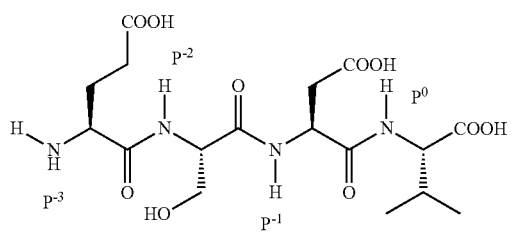

| Compound | Position of modification | Structure of modification | PDZ1 | PDZ2 |
|---|---|---|---|---|
| NR2B (1) | — | — | 18 ± 0.92 | 4.1 ± 0.17 |
| ESDV (SEQ ID NO: 32) (8) | — | — | 56 ± 2.4 | 28 ± 0.92 |
| 15 | $P^0$ | $CH_3$ | NA[b] | NA[b] |

TABLE 2-continued $K_i$ values of N-methylated ESDV (SEQ ID NO: 32) analogues[a]

[Chemical structure of tetrapeptide showing positions P⁻³, P⁻², P⁻¹, P⁰ with COOH, NH, HO groups]

| Compound | Position of modification | Structure of modification | PDZ1 | PDZ2 |
|---|---|---|---|---|
| 16 | $P^{-1}$ | $CH_3$ | 87 ± 3.1 | 78 ± 4.5 |
| 17 | $P^{-2}$ | $CH_3$ | NA[b] | NA[b] |
| 18 | $P^{-3}$ | $CH_3$ | 24 ± 1.8 | 15 ± 1.2 |

[a]$K_i$ values are shown as mean ± SEM in μM based on at least four individual measurements.
[b]NA: No activity.

The effects of modifying side-chains in ESDV (SEQ ID NO: 32) (8) were investigated by substituting with proteinogenic and non-proteinogenic amino acids (Table 3) with focus on changes in size and/or polarity in an attempt to optimize PDZ binding and drug-likeness. Initially, Val bait, in the absence of a peptide analogue inhibitor. The NMDAR/PSD-95 inhibitor $E_{Me}$TAV (SEQ ID NO: 31) (40) is shown to be a very effective inhibitor of NMDAR/PSD-95 interactions.

Figure 4:
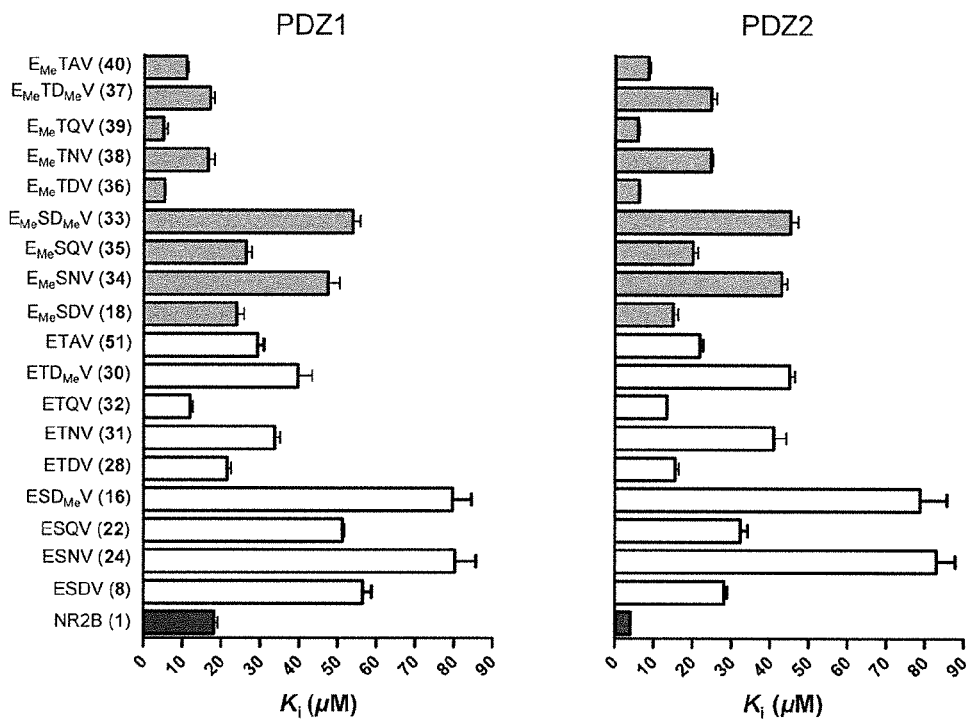
FIG. 4. $K_i$ values of N-methylated tetrapeptides and their corresponding non-methylated tetrapeptides towards PDZ1 and PDZ2, where individually favourable substitutions have been combined and error bars indicate SEM based on at least four individual measurements.

Example 4. Enhancing the Affinity of Peptide Ligands for PDZ1 and 2 Domains by a Combination of Substitutions to Obtain an NMDAR/PSD-95 Inhibitor of the Invention The above tests to improve peptide ligand affinity showed that Thr (28) and N-methyl Glu ($E_{Me}$) (18) in positions $P^{-2}$ and $P^{-3}$, respectively of the tetrapeptide ESDV (SEQ ID NO: 32) (8) are favorable. Modifications in position $P^0$ are generally not allowed, whereas a greater degree of freedom for modification is permitted in position $P^{-1}$. Based on these observations three series of compounds were designed and synthesized: Two series of compounds, ETXV (SEQ ID NO: 45) and $E_{Me}$SXV (SEQ ID NO: 46), with X being Gln, Asn, or N-Me-Asp, and a series of compounds, $E_{Me}$TXV (SEQ ID NO: 47), where X is Gln, Asn, N-Me-Asp, Ala, or Asp. A combination of the two favorable modifications, $E_{Me}$ at $P^{-3}$ and Thr at $P^{-2}$, led to compounds with $K_i$ values significantly lower than the NR2B peptide (1) at PDZ1 and only slightly higher at PDZ2 (FIG. 4). In particular, the modified tetrapeptides, $E_{Me}$TDV (SEQ ID NO: 35) (36) and $E_{Me}$TQV (SEQ ID NO: 48) (39) are ca. 3-fold more potent than the WT peptide 1 at PDZ1 and only slightly less potent at PDZ2.

Introducing the small, non-polar amino acid Ala in $P^1$ giving $E_{Me}$TAV (SEQ ID NO: 31) (40) provided an inhibitor that was more potent than 1 at PDZ1 and only 2-fold less potent for PDZ2. Although, 40 demonstrated some activity at PDZ3, the $K_i$ value at PDZ3 was still considerably higher (~79 μM) relative to that of PDZ1 and PDZ2, thus 40 is considered selective towards PDZ1 and PDZ2 relative to PDZ3. Substituting in the $P^{-1}$ position with N-Me-Asp (37) or Asn (38) reduced affinity compared to $E_{Me}$TDV (SEQ ID NO: 35) (36), but these peptides were still equally potent towards PDZ1 compared to peptide 1 (FIG. 4). In conclusion, N-terminal methylation of tetrapeptides increases their binding affinity for PDZ1 and PDZ2 domains, as seen for all N-methylated ligands in FIG. 4, as compared to their corresponding non-N-methylated ligands. Furthermore, the increase in affinity due to methylating the N-terminal amine of the tetrapeptides is sufficiently great that it can compensate for the introduction of amino acid analogues e.g. position $P^{-1}$ that increase the in vivo stability of the ligand, such as N-Me-Asp, even when this reduces ligand affinity.

Figure 5A:
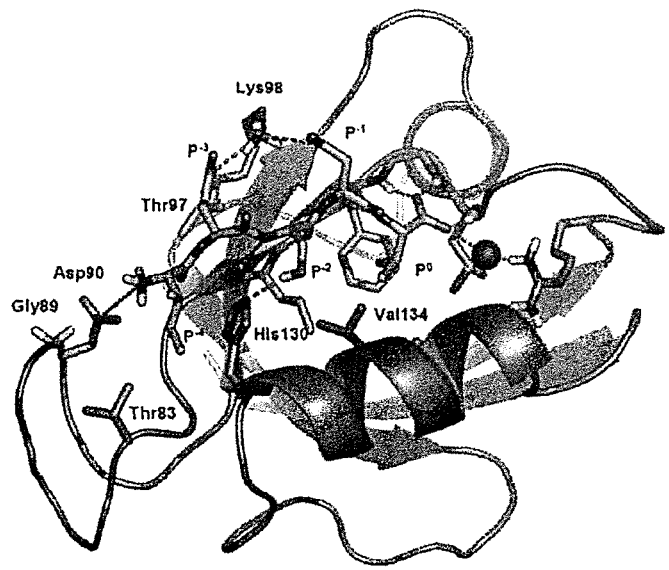
FIG. 5A. IESDV (SEQ ID NO: 33) (7) peptide docked into the PDZ1 homology model.

Example 5: Molecular Modeling and Docking of a Peptide Ligand in the Binding Pocket of the PDZ Domain Homology models of PDZ1 and PDZ2 were generated using Prime based on the X-ray crystallographic structure of PDZ3 in complex with CRIPT peptide,[10] and flexible docking of key peptides was performed using Glide. Initially, the pentapeptide IESDV (SEQ ID NO: 33) (7) was docked into PDZ1, resulting in a binding mode where the backbone of 7 superimposes with the backbone of the CRIPT peptide in PDZ3. However, an electrostatic interaction not found in the PD3-CRIPT structure, emerges between the N-terminal amino group of 7 and Asp90 in the large βB-βC loop of PDZ1 (FIG. 5A). A hydrophobic pocket is formed by Thr 83, Gly89 and His130 in PDZ1 (PDZ2: His225, Val178 and Pro184), which is partially filled by the side chain of Ile in position $P^{-4}$. The Glu residue in $P^{-3}$ interacts with Thr97 and Lys98 from the βC strand of PDZ1 (PDZ2: Thr192 and Lys193) through hydrogen bonding and electrostatic forces, explaining the importance of this residue for affinity (FIG. 5A). The hydroxyl group of Ser in $P^{-2}$ forms a hydrogen bond with His130, similar to that observed in the PDZ3-CRIPT structure. Replacing Ser ($P^{-2}$) with Thr, allows the additional methyl group to interact with a hydrophobic area created by Val134 in PDZ1 (PDZ2: Val229); which may explain the increased affinity of the Ser-to-Thr substitution. Substitutions with larger unnatural amino acids in $P^{-2}$ are probably not allowed due to steric clashes with the PDZ residues.

Figure 5B:
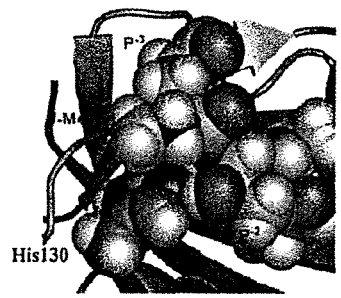
FIG. 5B. $E_{Me}TAV$ (SEQ ID NO: 31) (40) peptide docked into the PDZ1 homology model.
Figure 5C:
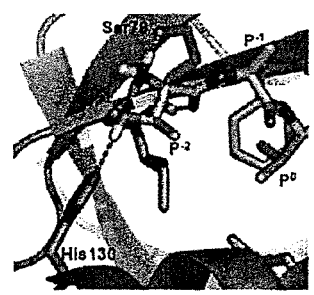
FIG. 5C. TAV (49) peptide docked into the PDZ1 homology model.

In the PDZ3-CRIPT structure the side chain of $P^{-1}$ does not interact with a residue in PDZ3.[10] In our model, we see an electrostatic interaction between Asp ($P^{-1}$) and Lys98 (FIG. 5A). We observed that Asp could be replaced with Gln or Ala indicating that neither charge nor hydrogen bonding is crucial for affinity. On the other hand, introduction of Asn in the $P^{-1}$ position reduced the affinity more extensively, demonstrating that not all side chain substitutions are equally allowed. Methylation of the N-terminal amino group enhanced the affinities for the tetrapeptides. Docking of $E_{Me}$TAV (SEQ ID NO: 31) (40) into PDZ1 reveals that the N-terminal amino group is in close proximity to His130, thereby creating a favorable cation-π interaction (FIG. 5B). The interaction is further stabilized by the N-methyl group, which is situated in the π-system of the imidazole ring of His130 (FIG. 5B), which explains the increased affinity upon N-methylation. Side chain groups of position $P^0$, $P^{-2}$, and $P^{-3}$ and ligand backbone are bound to PDZ in the same configuration as for the pentapeptide 7. Docking of TAV (49) into the PDZ1 homology model show that the N-terminal amino group mediates charge-assisted hydrogen bonding to the hydroxyl oxygen of Ser78 (PDZ2: Ser173) and a backbone carbonyl group (FIG. 5C).

Example 6. Enhancing the Affinity of the Peptide Ligand ETAV (SEQ ID NO: 40) for PDZ1 and 2 Domains by N-Terminal Modification to Obtain an NMDAR/PSD-95 Inhibitor of the Invention The molecular modeling studies suggest that the methyl group in $E_{Me}$TAV (SEQ ID NO: 31) (40) only partially overlaps with the His130 aromatic side-chain in PDZ1 (FIG. 5B), indicating that replacing the methyl group with larger groups could improve affinity through increased hydrophobic interactions and/or aromatic stacking interactions. A series ETAV (SEQ ID NO: 40) (51) analogues were therefore designed and synthesized where the N-methyl group was replaced with larger aliphatic and aromatic substituents (Table 4). N-alkylation of ETAV (SEQ ID NO: 40) was facilitated by a Mitsunobu reaction using the Fukuyama protocol,[6] as previously applied for preparation of N-alkylated peptides.[7] The terminal amino group of ETAV (SEQ ID NO: 40) was activated as a nitrobenzyl sulfonamide, and subsequently reacted with a range of alcohols mediated by diisopropyl azadicarboxylate (DIAD) and Ph$_3$P to give the protected, resin-bound products (Scheme 1 in FIG. 6). The final products were obtained by deprotection of the sulfonamide and cleavage from the resin providing the desired products, compounds 52-56 and 58-63, in excellent purity and generally high yield (Table 4).

Initially, the methyl group of $E_{Me}$TAV (SEQ ID NO: 31) (40) was replaced with ethyl (52), propyl (53) and butyl (54); molecular docking studies specifically suggested that ethylated ETAV (SEQ ID NO: 40) (52) would have similar affinity to $E_{Me}$TAV (SEQ ID NO: 31) (40), whereas propylated and butylated ETAV (SEQ ID NO: 40) (53 and 54) should have increased affinity. Biological evaluation of the compounds confirmed this prediction, TABLE 4-continued $K_i$ values of N-terminally modified ETAV (SEQ ID NO: 40) peptides.[a]

| Compound | R | PDZ1 | PDZ2 | PDZ3 |
|---|---|---|---|---|
| 61 | 3,4-dichlorophenethyl | 2.4 ± 0.25 | 1.1 ± 0.11 | 6.7 ± 0.20 |
| 62 | 3,4-difluorophenethyl | 0.98 ± 0.06 | 1.0 ± 0.043 | 7.8 ± 0.34 |
| 63 | naphthalen-2-ylethyl | 1.0 ± 0.33 | 0.95 ± 0.05 | 10 ± 0.22 |

[a] $K_i$ values are shown as mean ± SEM in μM based on at least four individual measurements.
[b] NA: No activity.

Generally, the increased affinity was more pronounced for PDZ2 than PDZ1, and compounds 53 and 54 were equipotent to the NR2B peptide (1) at PDZ2, and ca. 2-fold more potent at PDZ1. In addition affinity towards PDZ3 was also increased, although a significant selectivity for PDZ1 and PDZ2 remain (Table 4). Increasing the bulk and hydrophobicity of the N-alkyl substituents even further, modifying ETAV (SEQ ID NO: 40) with methylene- and ethylene-cyclohexane (55 and 56) led to dramatic increases in affinity. Compared to the starting point, the NR2B peptide (1), compounds 55 and 56 shows a ca. 19-fold increase in affinity towards PDZ1 and 56 shows a 9-fold increase in affinity towards PDZ2. Thus, peptide derivative 56 is a very potent inhibitor of the PSD-95/NMDA receptor interaction and significantly more potent compound that those reported to date.

In view of this improvement of affinity, attention was focussed on substitutions with an aromatic group, which the modeling studies suggested would also improve affinities compared to 40 and 51-54. Initially, the pentapeptide, FETAV (SEQ ID NO: 49) (57) was prepared, with an aromatic side-chain in the P$^{-4}$ position. The pentapeptide 57 had a 3- and 2-fold increase in affinity at PDZ1 and PDZ2, respectively compared to the NR2B peptide (1), thus confirming that an aromatic substituent in P$^{-4}$ is favorable. This prompted the synthesis of peptide derivatives, where the N-terminus of ETAV (SEQ ID NO: 40) was alkylated with aromatic substituents as in compounds 58-63 (Table 4). All of the six peptide derivatives (58-63) had improved affinity compared to both the NR2B peptide (1) and $E_{Me}$TAV (SEQ ID NO: 31) (40). The length of the spacer between the aromatic group and the terminal amino group is important, and a gradual increase in affinity for PDZ1 is seen when extending from methylene (58), ethylene (59) to propylene spacer (60), whereas the ethylene spacer (59) is the most potent at PDZ2 (Table 4). Next, the effect of substituting the aromatic ring was investigated; substitution with two chloride atoms (61) increased affinity compared to 59 at both PDZ1 and PDZ2. Replacing chloride with fluorine (62) increased affinity even further, and 62 showed $K_i$ values around 1 μM at both PDZ1 and PDZ2, thus being almost equipotent to the ethylenecyclohexane derivative 56. Thus changing the electronic properties of the aromatic ring affect affinity, which is suggested by modeling studies, to be due to the interaction of the aromatic group with His130 of PDZ1. Docking compounds 59 and 61-62 into the homology model of PDZ1 suggest a perpendicular stacking between the aromatic group from the peptides and His130. Increasing the bulk of the aromatic group further to a naphthalene-2-yl moiety (63) resulted in a compound equipotent to 62. For all compounds a considerable increase in affinity towards PDZ3 was observed. However, a significant selectivity is preserved and for the most potent inhibitor, compound (56), a 10- and 20-fold selectivity towards PDZ1 and PDZ2 relatively to PDZ3 is seen (Table 3). In summary, by rational design guided by molecular docking techniques, it was possible to optimize the alkyl group used to N-alkylate the tetrapeptides, whereby surprisingly potent ligands towards the PDZ1 and PDZ2 domains of PSD-95 were generated.

Example 7. Substitution of Amino Acids in the P$^{-1}$ and P$^{-3}$ Position in Alkylated Tetrapeptide Ligands to Obtain an NMDAR/PSD-95 Inhibitor of the Invention Tetrapeptides and alkylated tetrapeptides in which the amino acid in P$^{-3}$ was either E, Q, A and the amino acid at P-1 was either D or A, were investigated to determine whether amino acids with a lesser charge and/or hydrophilicity could be combined in the alkylated tetrapeptide YTXV (SEQ ID NO: 29), and whether alkylation would compensate for any reduction in affinity due to these amino acid substitutions (Table 5). As seen in Table 5, it is possible to substitute the negatively charged Glu in P$^{-3}$ and Asp in P$^{-1}$ in the N-alkylated tetrapeptide with neutral or even hydrophobic amino acids, such as Gln and Ala, even in combination, and maintain an affinity to the PDZ1 and 2 domain close to that of the control peptide (1). This is an important finding since the cell membrane is more permeable to tetrapeptides with a reduced charge and hydrophilicity, which will enhance their uptake by a cell.

Example 8. Enhancing the Affinity Against PDZ1-2 by Linking Modified Peptide Ligands with a PEG-Linker, Thereby Increasing the Affinity Towards this PDZ Motif but not the Single PDZ Domains Dimerization of the modified peptide ligands of the invention with a PEG-linker provides a NMDAR/PSD-95 inhibitor with several pharmacokinetic advantages. PEG (polyethylene glycol) is selected as the linker because it is a non-toxic chemical and when linked to the modified peptide ligands will serve to lower their renal clearance, provide protection against enzyme cleavage, reduce immunogenicity, and enhance their solubility and cell membrane permeability. Furthermore, these dimeric ligands, linked by PEG, are shown to have greatly increased affinity towards PDZ1-2 of PSD-95. Initially, this is demonstrated by the use of PEG molecules to chemically link two identical peptide ligands (IESDV (SEQ ID NO: 33)) as in compound 74 or the alkylated GE(R)TDV (R=cyclohexylethyl; N-alkylated in P$^{-3}$) pentapeptide as in compound 75 (see structures in FIG.

TABLE 5

K$_i$ values of modified peptides with the general structure.$^a$

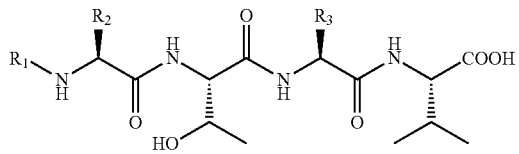

| Compound | R$_1$ | R$_2$ | R$_3$ | PDZ1 | PDZ2 | PDZ3 |
|---|---|---|---|---|---|---|
| NR2B (1) | — | — | — | 18 ± 0.92 | 4.1 ± 0.17 | NA$^b$ |
| CRIPT (2) | — | — | — | 97 ± 18 | 25 ± 1.6 | 2.1 ± 0.2 |
| ETDV (SEQ ID NO: 41) (64) | H | (CH$_2$)$_2$COOH | CH$_2$COOH | 22 ± 0.95 | 16 ± 0.88 | NA$^b$ |
| QTDV (SEQ ID NO: 50) (65) | H | (CH$_2$)$_2$CONH$_2$ | CH$_2$COOH | 58 ± 3.5 | 60 ± 1.9 | NA$^b$ |
| ATDV (SEQ ID NO: 51) (66) | H | CH$_3$ | CH$_2$COOH | 30 ± 0.72 | 38 ± 4.2 | NA$^b$ |
| ETAV (SEQ ID NO: 40) (51) | H | (CH2)$_2$COOH | CH$_3$ | 29 ± 1.6 | 22 ± 0.92 | 260 ± 20 |
| QTAV (SEQ ID NO: 52) (67) | H | (CH$_2$)$_2$CONH$_2$ | CH$_3$ | 112 ± 4.4 | 108 ± 6.3 | >400 |
| ATAV (SEQ ID NO: 53) (68) | H | CH$_3$ | CH$_3$ | 64 ± 1.7 | 73 ± 3.8 | 400 |
| ETDV (SEQ ID NO: 41) (69) | Cyclohexylethyl | (CH2)$_2$COOH | CH$_2$COOH | 1.8 ± 0.23 | 0.75 ± 0.1 | NA$^b$ |
| QTDV (SEQ ID NO: 50) (70) | Cyclohexylethyl | (CH$_2$)$_2$CONH$_2$ | CH$_2$COOH | 6.2 ± 0.93 | 4.4 ± 0.59 | NA$^b$ |
| ATDV (SEQ ID NO: 51) (71) | Cyclohexylethyl | CH$_3$ | CH$_2$COOH | 5.8 ± 0.33 | 3.6 ± 0.30 | >400 |
| ETAV (SEQ ID NO: 40) (56) | Cyclohexylethyl | (CH2)$_2$COOH | CH$_3$ | 0.94 ± 0.1 | 0.45 ± 0.1 | 11 ± 0.43 |
| QTAV (SEQ ID NO: 52) (72) | Cyclohexylethyl | (CH$_2$)$_2$CONH$_2$ | CH$_3$ | 21 ± 1.1 | 12 ± 0.36 | 141 ± 14 |
| ATAV (SEQ ID NO: 53) (73) | Cyclohexylethyl | CH$_3$ | CH$_3$ | 8.9 ± 1.0 | 8.1 ± 0.12 | 89 ± 3.3 |

$^a$K$_i$ values are shown as mean ± SEM in μM based on at least three individual measurements.
$^b$NA: No affinity.

Figure 8:
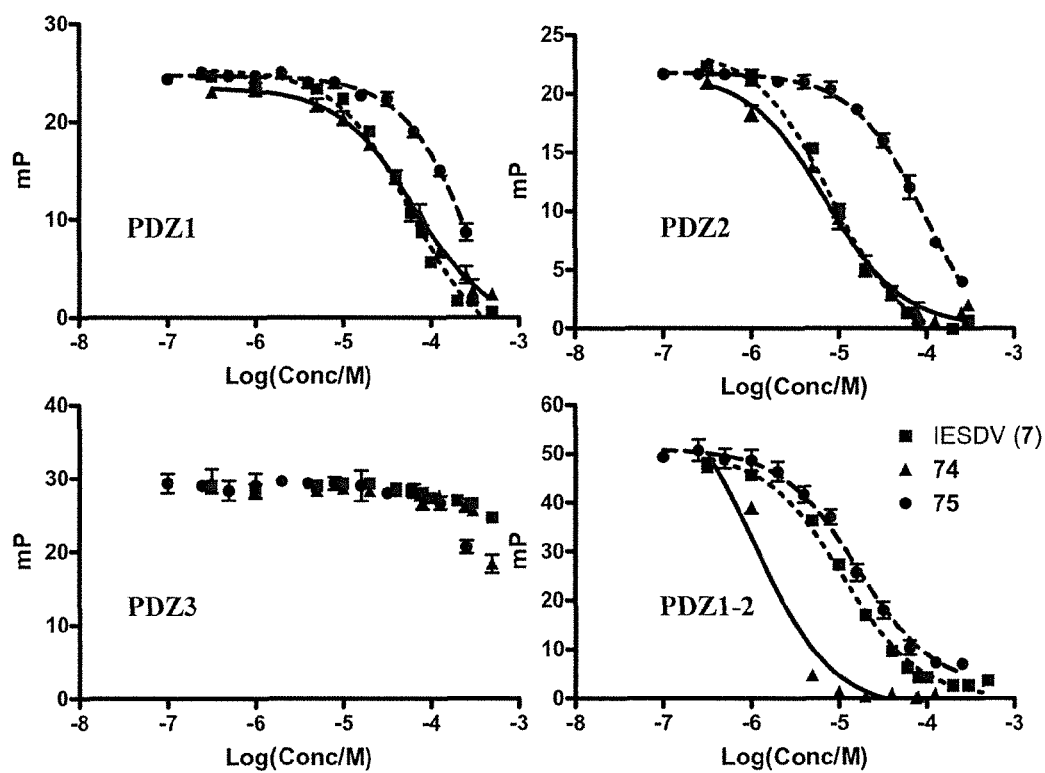
FIG. 8. Inhibition curves of dimeric peptide ligands 74 and 75 to PDZ1, PDZ2, PDZ3 and PDZ1-2 domains measured by fluorescence polarization (FP).

7). In both these examples a dramatic increase in affinity for the tandem construct PDZ1-2 is seen (See FIG. 8 and $K_i$ values in table 6), reflecting the synergistic effect that is obtained by linking two ligands together.

TABLE 6

$K_i$ values for dimeric peptide ligands measured by FP.[a]

| Compound | R, X, Y | PDZ1 | PDZ2 | PDZ1-2 | PDZ3 |
|---|---|---|---|---|---|
| NR2B (1) | — | 18 ± 0.92 | 4.1 ± 0.17 | 6.8 ± 0.20 | NA[b] |
| (IESDV)$_2$-PEG12 (SEQ ID NO: 33) (74) | R = H X = Ile Y = Ser | 22 ± 1.4 | 2.8 ± 0.32 | ~0.1[c] | NA[b] |

TABLE 6-continued $K_i$ values for dimeric peptide ligands measured by FP.[a]

| Compound | R, X, Y | PDZ1 | PDZ2 | PDZ1-2 | PDZ3 |
|---|---|---|---|---|---|
| (GE[R]TDV)$_2$-PEG12 (SEQ ID NO: 42) (75) | R = Cyclo-hexylethyl X = Gly Y = Thr | 83 ± 6.2 | 55 ± 2.1 | 5.5 ± 0.46 | NA[b] |

[a]$K_i$ values are shown as mean ± SEM in μM based on at least three individual measurements.
[b]NA: No affinity.
[c]Because of the very low affinity of this ligand, an exact $K_i$ value can not be calculated in the FP assay (See text).

An exact $K_i$ value for 74 could not be calculated using the FP assay, due to its very low $K_i$. However, the $K_i$ was found to be about 100 nM in a fluorescence titration assay (stopped-flow binding assay[25]).

Figure 9:
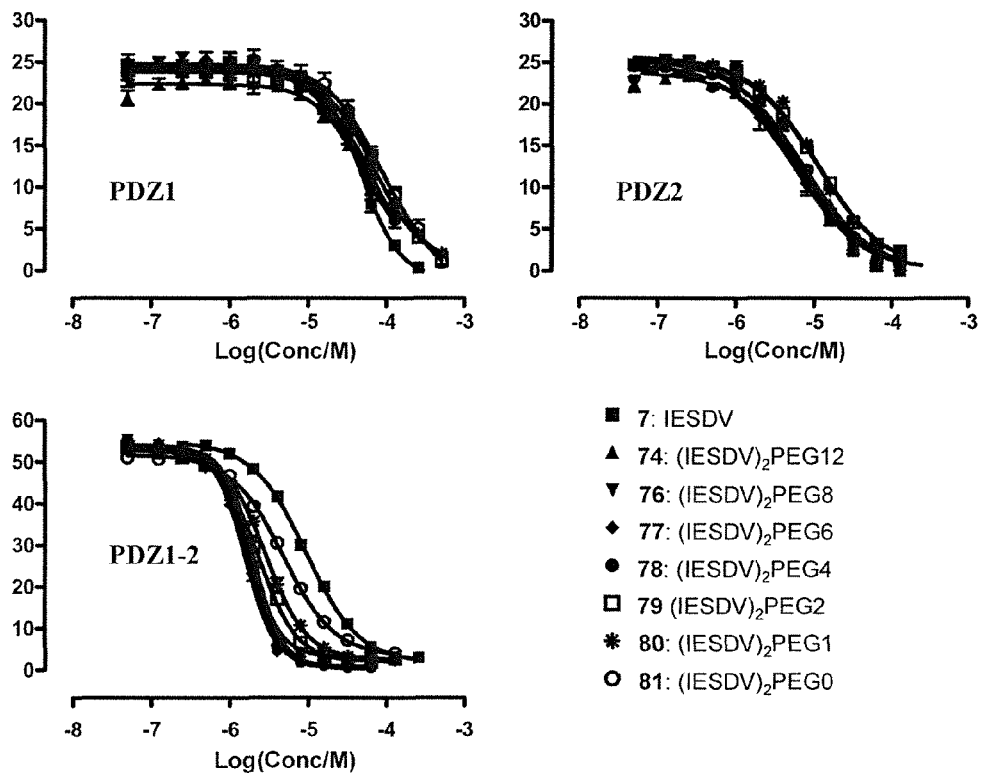
FIG. 9. Inhibition curves of dimeric peptide ligands 74, 76-81 to PDZ1, PDZ2, and PDZ1-2 domains measured by FP.

In order to optimize the length of the PEG-linker, IESDV (SEQ ID NO: 33) was further dimerized with a linker comprising PEG8-, 6-, 4-, 2-, 1-, or 0-diacids (76-81) and tested in FP and ITC. It was found that from PEG4 to PEG6 is the optimal linker size range (where PEG4 (78) has a $K_d$=32 nM towards PDZ1-2) and that further shortening of the linker resulted in lower affinity (FIG. 9, Table 7). It was also noticed that dimeric ligand and PDZ1-2 binds in a 1:1 ratio as expected.

TABLE 7

FP and ITC measurements for dimeric peptide ligands with the general structure:

| | | | FP ($K_i$/μM)[a] | | ITC ($K_d$/μM)[a] | |
|---|---|---|---|---|---|---|
| Compound | Peptide | X | PDZ2 | PDZ12 | PDZ2 | PDZ12 |
| 7 | IESDV (SEQ ID NO: 33) | monomeric | 3.1 ± 0.15 | 3.9 ± 0.12 | 2.6 ± 0.19 | 3.2 ± 0.16 |
| 8 | ESDV (SEQ ID NO: 32) | monomeric | 28 ± 0.92 | 28 ± 2.9 | ND | ND |
| 82 | IETAV (SEQ ID NO: 36) | monomeric | 1.7 ± 0.2 | 2.5 ± 0.13 | ND | 1.9 ± 0.11 |
| 86 | IATAV (SEQ ID NO: 54) | monomeric | 16 ± 0.33 | 18 ± 0.47 | ND | ND |
| 89 | IATA$_{Me}$V (SEQ ID NO: 55) | monomeric | 104 ± 9 | 142 ± 5 | ND | ND |
| 74 | IESDV (SEQ ID NO: 33) | 12 | 3.1 ± 0.13 | ~0.1[b] | ND[c] | 0.09 ± 0.014 |
| 76 | IESDV (SEQ ID NO: 33) | 8 | 2.6 ± 0.13 | ~0.1[b] | ND | 0.12 ± .027 |
| 77 | IESDV (SEQ ID NO: 33) | 6 | 2.0 ± 0.02 | ~0.1[b] | ND | 0.039 ± 0.01 |
| 78 | IESDV (SEQ ID NO: 33) | 4 | 2.7 ± 0.12 | ~0.1[b] | 3.3 ± 0.02 | 0.032 ± 0.01 |

TABLE 7-continued

FP and ITC measurements for dimeric peptide ligands with the general structure:

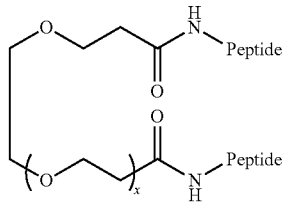

| | | | FP ($K_i$/μM)[a] | | ITC ($K_d$/μM)[a] | |
|---|---|---|---|---|---|---|
| Compound | Peptide | X | PDZ2 | PDZ12 | PDZ2 | PDZ12 |
| 79 | IESDV (SEQ ID NO: 33) | 2 | 4.7 ± 0.21 | 0.27 ± 0.03 | ND | 0.22 ± 0.01 |
| 80 | IESDV (SEQ ID NO: 33) | 1 | 4.7 ± 0.16 | 0.56 ± 0.06 | ND | 0.46 ± 0.02 |
| 81 | IESDV (SEQ ID NO: 33) | 0 | 3.1 ± 0.17 | 1.5 ± 0.09 | ND | 1.1 ± 0.09 |
| 83 | IETAV (SEQ ID NO: 36) | 4 | 1.1 ± 0.07 | ~0.1[b] | ND | 0.011 ± 0.01 |
| 84 | ESDV (SEQ ID NO: 32) | 12 | 22 ± 0.18 | 0.92 ± 0.03 | ND | ND |
| 85 | ESDV (SEQ ID NO: 32) | 8 | 19 ± 1.2 | 1.0 ± 0.05 | ND | ND |
| 87 | IATAV (SEQ ID NO: 54) | 12 | 13 ± 1.1 | 1.0 ± 0.06 | ND | ND |
| 88 | IATAV (SEQ ID NO: 54) | 4 | 25 ± 0.88 | 1.1 ± 0.07 | ND | ND |
| 90 | IATA$_{Me}$V (SEQ ID NO: 55) | 4 | 103 ± 1.1 | 13 ± 0.6 | ND | ND |

[a]$K_d$/$K_i$ values are shown as mean ± SEM based on at least three individual measurements.
[b]Because of the very low affinity of this ligand, an exact $K_i$ value can not be calculated in the FP assay (See tesx).
cND: Not determined.

The potency of the ligand was further enhanced by combining the PEG4 linker with an optimized peptide sequence, for example the ligand ((IETAV)$_2$PEG4 (SEQ ID NO: 36), 83) which has a $K_d$=11 nM towards PDZ1-2 of PSD-95. The exceptionally strong binding affinity of this ligand (Structure in FIG. 10) towards the tandem PDZ1-2 construct was achieved without compromising its affinity to the single PDZ1 and PDZ2 domains. As compared to the monomeric ligand IETAV (SEQ ID NO: 36) (82), dimerization increased ligand affinity by 176 fold (FIG. 9, Table 7). Compared to the clinical candidate Tat-NR2B (3, Table 1), 83 has about 1000-fold greater affinity towards PDZ1-2 of PSD-95, thereby demonstrating that 83 has the affinity required for a strong drug candidate (Table 7).

Since dimerization enhances the binding affinity of a ligand towards PDZ1-2, it can also be used to transform low affinity PDZ1/PDZ2 ligands into high affinity PDZ1-2 ligands. Thereby, shorter peptides (e.g. ESDV (SEQ ID NO: 32)), hydrophobic and more cell permeable peptides (e.g. IATAV (SEQ ID NO: 36) and IATA$_{Me}$V (SEQ ID NO: 55)), and proteolytically stable peptides (e.g. IATA$_{Me}$V (SEQ ID NO: 55)) can be dimerized to provide potent ligands in which their respective beneficial properties are preserved (Table 7).

In conclusion, dimeric linkage of peptide-ligands (N-alkylated or not) using PEG molecules facilitates simultaneous binding of the ligand to PDZ1 and 2 of PSD-95, whereby binding affinity is increased. Thereby, a potent ligand, specific for the PDZ1-2 protein motif is obtained, having increased selectivity towards PSD-95, together with improved pharmacokinetic properties.

Figure 11:
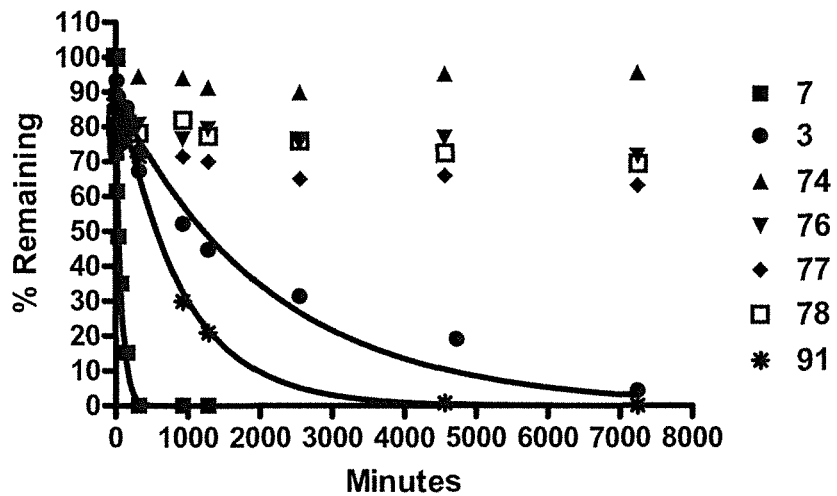
FIG. 11. Stability of the compounds 74 and 76-78 in human blood plasma is shown and compared with the stability of the corresponding monomeric ligand (7), the clinical candidate Tat-N2B (3), and the pegylated, monomeric ligand 91.

Example 9. PEG-Based Dimerization of Peptide Ligands Leads to Human Blood Plasma Stability Stability is a general concern in relation to peptide-based drugs, as proteases in human blood facilitate degradation of peptides. Accordingly, the time-dependent stability of key compounds was tested in a human blood plasma stability assay. Monomeric peptides were degraded relatively fast (compounds 7, 29, 82 and 86 had a half-life of about 17-55 minutes; Table 8), but PEG-based dimerization of these peptide ligands leads to highly plasma-stabile compounds (83, 87, 88) and in some cases (74, 76-78, 90) complete resistance towards degradation was achieved, as no significant degradation could be detected over a time period of 6 days (Table 8 and FIG. 11). For both the monomeric and dimeric ligands it is seen that the peptide sequence, IESDV (SEQ ID NO: 33), has a greater degree of stability compared to IETAV (SEQ ID NO: 36) and IATAV (SEQ ID NO: 54), and that N-methylation of P$^{-1}$ increases stability, since IATA$_{Me}$V (SEQ ID NO: 55) demonstrates a longer half-life compared to IATAV (SEQ ID NO: 54) (Table 8). Finally, it is noticed that the dimeric compounds, 74-76-78, and 90 display a longer half-life compared to the clinical candidate Tat-N2B (3) (Table 8 and FIG. 11).

The pegylated, monomeric ligand (91) also demonstrates an increased half life (about 10 fold) compared to non-pegylated peptide 7 (Table 8), thus the PEG-linker is instrumental for this effect. However, 91 is not completely resistant to plasma treatment, as seen for the IESDV-based (SEQ ID NO: 33) dimeric ligands (74, 76-78; Table 8), hence having two peptide ligands in one molecule contributes to

TABLE 8

Blood plasma half life ($T_{1/2}$) of key compounds

| Compound | $T_{1/2}$ (minutes) |
| --- | --- |
| Tat-N2B (3) | 1468 |
| IESDV (SEQ ID NO: 33) (7) | 53 |
| IETAV (SEQ ID NO: 36) (82) | 50 |
| IATAV (SEQ ID NO: 54) (86) | 17 |
| IATA$_{Me}$V (SEQ ID NO: 55) (89) | 32 |
| (IESDV)$_2$PEG12 (SEQ ID NO: 33) (74) | >8000 |
| (IESDV)$_2$PEG8 (SEQ ID NO: 33) (76) | >8000 |
| (IESDV)$_2$PEG6 (SEQ ID NO: 33) (77) | >8000 |
| (IESDV)$_2$PEG4 (SEQ ID NO: 33) (78) | >8000 |
| (IETAV)$_2$PEG4 (SEQ ID NO: 36) (83) | 409 |
| (IATAV)$_2$PEG12 (SEQ ID NO: 54) (87) | 183 |
| (IATAV)$_2$PEG4 (SEQ ID NO: 54) (88) | 123 |
| (IATA$_{Me}$V)$_2$PEG4 (SEQ ID NO: 55) (90) | >8000 |
| IESDV-PEG4 (SEQ ID NO: 33) (91) | 602 | improving stability in blood plasma.

Figure 12:
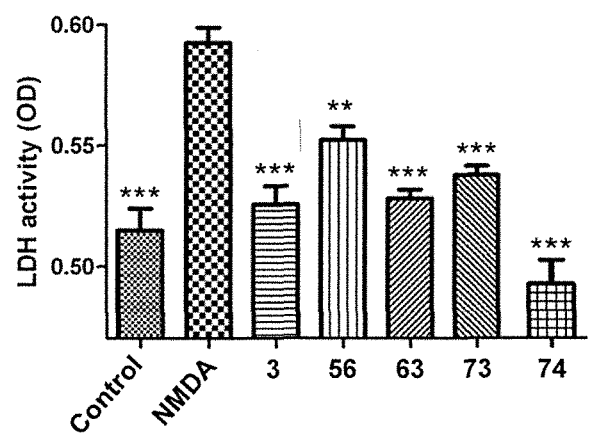
FIG. 12. Effect on NMDA-mediated excitotoxicity in cultured cortical neurons of compound 3, 56, 63, 73 and 74 at a concentration of 500 nM.

Example 10. Analysis of the Neuroprotective Effect of an NMDAR/PSD-95 Inhibitor of the Invention in Mammalian Neurons Ex Vivo In order to evaluate the therapeutical potential of dimeric ligands and N-alkylated tetrapeptides key compounds from each series were tested in a neuronal cell based ex vivo assay. This assay evaluates membrane permeability together with compound specificity and ability to attenuate NMDA-induced excitotoxicity. This assay thereby constitutes a direct model of the pathogenesis of e.g. stroke or traumatic brain injuries and measures important compound properties. These experiments show that both N-alkylated tetrapeptides (56, 63 and 73) and dimeric ligands (74), at a concentration of 500 nM, were able to permeate the neuronal plasma membrane and inhibit neuronal excitotoxicity, as efficiently as the clinical candidate Tat-N2B (3) (FIG. 12).

Example 11. Prevention of NMDA Evoked nNOS Activation

NMDA evoke changes in cGMP levels in neurons which provide a surrogate measure of NO production by nNOS. Samples of cortical neurons are prepared, cultured and incubated as previously described. Then, the level of cGMP in the neuron samples is measured, thereby providing a surrogate measure of the prevention of NOS activation by the NMDAR/PSD-95 inhibitor of the invention.

Example 12. Analysis of the Membrane Permeability of an NMDAR/PSD-95 Inhibitor of the Invention in Mammalian Cells A BRET$^2$ assay is used to analyse the ability of an NMDAR/PSD-95 inhibitor to permeate mammalian cells. Accordingly, 0.5 million COS-7 cells per well are seeded into a 6-well plate (in replicates) and grown in 10% fetal calf serum/Dulbecco's modified Eagle's medium (DMEM) and transfected with 3.7 μg of each DNA construct per well using COS7 transfection reagent (Altogen) according to the manufacturer's protocol. DNA constructs for transfection comprise a DNA sequence encoding a fusion protein designated as follows:

GFP-NR2B DNA [SEQ ID NO: 9] encoding GFP-NR2B protein [SEQ ID NO: 10];

GFP-NR2B AA DNA [SEQ ID NO: 11] encoding GFP-NR2B AA protein [SEQ ID NO: 12]

GFP-PDZ2 DNA [SEQ ID NO: 13] encoding GFP-PDZ2 protein [SEQ ID NO: 14]

PDZ2-GFP [SEQ ID NO: 15] encoding PDZ2-GFP protein [SEQ ID NO: 16]

Rluc-NR2B DNA [SEQ ID NO: 17] encoding Rluc-NR2B protein [SEQ ID NO: 18]

Rluc-NR2B AA DNA [SEQ ID NO: 19] encoding Rluc-NR2B AA protein [SEQ ID NO: 20]

Rluc-PDZ2 DNA [SEQ ID NO: 21] encoding Rluc-PDZ2 protein [SEQ ID NO: 22]

PDZ2-Rluc DNA [SEQ ID NO: 23] encoding PDZ2-Rluc DNA [SEQ ID NO: 24], each of which are individually cloned in the vector pcDNA3.1 vector (Invitrogen). Cells in each well are transfected with a pair of vectors, encoding one of the following alternative pairs of fusion proteins:

wild-type GFP-NR2B or mutant GFP-NR2B AA with Rluc-PDZ2 or PDZ2-Rluc;

wild-type Rluc-NR2B or mutant Rluc-NR2B AA with GFP-PDZ2 or PDZ2-GFP;

The total amount of transfection DNA is kept constant by adding empty pcDNA3.1 vector (Invitrogen). The cells are then incubated for 2 days, during which period samples of an NMDAR/PSD-95 inhibitor of the invention are added to the wells in replicate plates, at a final concentration of at least 1 μM, more than 1 μM, or between 5 μM and 1.0 mM. The constructs encoding fusion with the mutant NR2B AA are included as controls, since the mutant is unable to bind to a PDZ domain of PSD-95.

After 2 days, the cells are washed, detached and re-suspended in 666 μL 1×PBS (8 g NaCl 0.2 g KCl 1.44 g Na$_2$HPO$_4$ 0.24 g KH2PO$_4$ in 800 ml of distilled H2O, adjusted to pH 7.4 with HCl). The cells are then spilt into two portions in 96 well plates (1.5·10$^6$ cells/well):

The first portion (in black plates) is used to determine the GFP levels and RLUC expression levels using a Mithras LB 940 plate reader (Berthold Technologies, Bad Wildbad, Germany). Fluorescence excitation is performed at 425/20 nm and emission is measured at 530/10 nm. Luminescence is assayed by addition of Coelenterazine h (Biotium Inc., Hayward Calif., USA) to a final concentration of 5 μM. Background values obtained with cells transfected with empty pcDNA3.1 vector only are subtracted, and the mean luminesence of triplicate wells/sample are calculated.

The second portion of the cells (in white plates) is submitted to DeepBlueC (Coelenterazine 400a; Biotium Inc., Hayward Calif., USA) excitation at a final concentration of 5 M, and the luminescence at the dual bands (515/30 nm and 410/80) is measured on the Mithras LB 940 plate reader. Background values are obtained with cells transfected with empty pcDNA3.1 vector only, and the means of triplicate wells/sample are calculated. BRET ratios are calculated as (emission515 nm−background515 nm)/(emission410 nm−background410 nm).

The background signal from RLUC is determined by co-expressing the Rluc construct with empty vector, and the BRET$^2$ ratio generated from this transfection is subtracted from all other BRET$^2$ ratios.

For BRET2 saturation experiments, a range of transfections are made with a stable amount of PDZ2-RLUC cDNA and increasing amounts of cDNA encoding the GFP2-NR2B protein. All measurements are made at room temperature.

Example 13. NMDAR/PSD-95 Inhibitors of the Invention have a Neuroprotective Effect Against Stroke Damage in Mammalian In Vivo A. Neuroprotection Against Stroke Damage by Pretreatment with NMDAR/PSD-95 Inhibitors.

Adult male Sprague-Dawley rats are subjected to transient MCAO for approximately 90 minutes by the intraluminal suture method, as set out in (29). The animal subjects are pretreated with a single intravenous bolus injection with either saline alone (control), saline supplemented with either NR2B peptide or an NMDAR/PSD-95 inhibitor of the invention at a final concentration of 3 nM/g body weight, 45 minutes prior to MCAO. Body temperature, blood pressure and blood gases are monitored and maintained in the animal subjects. The extent of cerebral infarction is measured after about 24 hours after MCAO onset. Tests include the postural reflex test and the forelimb-placing test to establish the degree of neurological function in the animal subjects during and following MCAO.

B. Attenuation of Stroke Damage by Post-Treatment with NMDAR/PSD-95 Inhibitors.

Adult male Sprague-Dawley rats are subjected to transient MCAO as set out above (A), but the single intravenous bolus injection with saline alone or supplemented with either NR2B peptide or an NMDAR/PSD-95 inhibitor is first administered one hour after the onset of MCAO. The animal subjects are then monitored over the 24-hour period following onset of MCAO, as set out above.

REFERENCES

1. Aarts, M.; Liu, Y.; Liu, L.; Besshoh, S.; Arundine, M.; Gurd, J. W.; Wang, Y. T.; Salter, M. W.; Tymianski, M. Treatment of ischemic brain damage by perturbing NMDA receptor-PSD-95 protein interactions. *Science* 2002, 298, 846-850.
2. Aarts, M. M.; Tymianski, M. Novel treatment of excitotoxicity: targeted disruption of intracellular signalling from glutamate receptors. *Biochem. Pharmacol.* 2003, 66, 877-886.
3. Cui, H.; Hayashi, A.; Sun, H. S.; Belmares, M. P.; Cobey, C.; Phan, T.; Schweizer, J.; Salter, M. W.; Wang, Y. T.; Tasker, R. A.; Garman, D.; Rabinowitz, J.; Lu, P. S.; Tymianski, M. PDZ protein interactions underlying NMDA receptor-mediated excitotoxicity and neuroprotection by PSD-95 inhibitors. *J. Neurosci* 2007, 27, 9901-15.
4. Thomson Current Drugs (http://www.thomson.com).
5. Nikolovska-Coleska, Z.; Wang, R.; Fang, X.; Pan, H.; Tomita, Y.; Li, P.; Roller, P. P.; Krajewski, K.; Saito, N. G.; Stuckey, J. A.; Wang, S. Development and optimization of a binding assay for the XIAP BIR3 domain using fluorescence polarization. *Anal. Biochem.* 2004, 332, 261-273.
6. Fukuyama, T.; Jow, C.-K.; Mui, C. 2- and 4-nitrobenzenesulfonamides: Exceptionally Versatile Means for Preparation of Secondary Amines and Protection of Amines. *Tetrahedron Lett* 1995, 36, 6373-6374.
7. Yang, L.; Chiu, K. Solid Phase Synthesis of Fmoc N-Methyl Amino Acids: Application of the Fukuyama Amine Synthesis. *Tetrahedron Lett* 1997, 38, 7307-7310.
8. Paduch, M.; Biernat, M.; Stefanowicz, P.; Derewenda, Z. S.; Szewczuk, Z.; Otlewski, J. Bivalent peptides as models for multimeric targets of PDZ domains. *Chembiochem.* 2007, 8, 443-452.
9. Niethammer, M.; Valtschanoff, J. G.; Kapoor, T. M.; Allison, D. W.; Weinberg, R. J.; Craig, A. M.; Sheng, M. CRIPT, a novel postsynaptic protein that binds to the third PDZ domain of PSD-95/SAP90. *Neuron* 1998, 20, 693-707.
10. Doyle, D. A.; Lee, A.; Lewis, J.; Kim, E.; Sheng, M.; MacKinnon, R. Crystal structures of a complexed and peptide-free membrane protein-binding domain: molecular basis of peptide recognition by PDZ. *Cell* 1996, 85, 1067-1076.
11. DeLano, W. L. The PyMOL Molecular Graphics System on World Wide Web http://www.pymol.org
12. Lim, I. A.; Hall, D. D.; Hell, J. W. Selectivity and promiscuity of the first and second PDZ domains of PSD-95 and synapse-associated protein 102. *J. Biol. Chem.* 2002, 277, 21697-21711.
13. Chi, C. N.; Gianni, S.; Calosci, N.; Travaglini-Allocatelli, C.; Engström, K.; Jemth, P. A conserved folding mechanism for PDZ domains. *FEBS Lett* 2007, 581, 1109-13.
14. Gianni, S.; Engström, A.; Larsson, M.; Calosci, N.; Malatesta, F.; Eklund, L.; Ngang, C. C.; Travaglini-Allocatelli, C.; Jemth, P. The kinetics of PDZ domain-ligand interactions and implications for the binding mechanism. *J. Biol. Chem.* 2005, 280, 34805-12.
15. Stiffler, M. A.; Chen, J. R.; Grantcharova, V. P.; Lei, Y.; Fuchs, D.; Allen, J. E.; Zaslavskaia, L. A.; MacBeath, G. PDZ domain binding selectivity is optimized across the mouse proteome. *Science* 2007, 317, 364-9.
16. Saro, D.; Li, T.; Rupasinghe, C.; Paredes, A.; Caspers, N.; Spaller, M. R. A thermodynamic ligand binding study of the third PDZ domain (PDZ3) from the mammalian neuronal protein PSD-95. *Biochemistry* 2007, 46, 6340-52.
17. Harris, B. Z.; Lau, F. W.; Fujii, N.; Guy, R. K.; Lim, W. A. Role of electrostatic interactions in PDZ domain ligand recognition. *Biochemistry* 2003, 42, 2797-805.
18. Hruby, V. J. Designing peptide receptor agonists and antagonists. *Nat. Rev. Drug Discov.* 2002, 1, 847-858.
19. Clemons, P. A. Design and discovery of protein dimerizers. *Curr. Opin. Chem. Biol.* 1999, 3, 112-5.
20. Hopfner, K. P.; Ayala, Y.; Szewczuk, Z.; Konishi, Y.; Di Cera, E. Chemical compensation in macromolecular bridge-binding to thrombin. *Biochemistry* 1993, 32, 2947-53.
21. Szewczuk, Z.; Gibbs, B. F.; Yue, S. Y.; Purisima, E.; Zdanov, A.; Cygler, M.; Konishi, Y. Design of a linker for trivalent thrombin inhibitors: interaction of the main chain of the linker with thrombin. *Biochemistry* 1993, 32, 3396-404.
22. Harris, J. M.; Martin, N. E.; Modi, M. Pegylation: a novel process for modifying pharmacokinetics. *Clin. Pharmacokinet.* 2001, 40, 539-51.
23. Long, J. F.; Tochio, H.; Wang, P.; Fan, J. S.; Sala, C.; Niethammer, M.; Sheng, M.; Zhang, M. Supramodular structure and synergistic target binding of the N-terminal tandem PDZ domains of PSD-95. *J. Mol. Biol.* 2003, 327, 203-214.
24. Wen, W.; Wang, W.; Zhang, M. Targeting PDZ domain proteins for treating NMDA receptor-mediated excitotoxicity. *Curr. Top. Med. Chem.* 2006, 6, 711-721.
25. Chi, C. N.; Engström, A.; Gianni, S.; Larsson, M.; Jemth, P. Two conserved residues govern the salt and pH dependencies of the binding reaction of a PDZ domain. *J. Biol. Chem.* 2006, 281, 36811-8.

The invention claimed is:

1. A compound comprising a first peptide or peptide analogue linked to a second peptide or peptide analogue by a linker, wherein the first and the second peptide or peptide analogue comprise at least four amide-bonded residues having the sequence of SEQ ID NO: 25 or SEQ ID NO: 26, wherein
   a. $Xaa_1$ is selected from among E, Q, and A, and
   b. $Xaa_3$ is selected from among A, Q, D, N, N-Me-A, N-Me-Q, N-Me-D, and N-Me-N.

2. The compound according to claim 1, wherein the first peptide or peptide analogue, the second peptide or peptide analogue, or both is N-alkylated in position $p^{-3}$ in the sequence.

3. The compound according to claim 1, wherein the linker is a PEG linker comprising 1 to 28 moieties (N=1-28) of ethylene glycol.

4. The compound according to claim 3, wherein the PEG linker comprises from 1 to 12 moieties (N=1-12) of ethylene glycol.

5. The compound according to claim 1, wherein the first peptide or peptide analogue, the second peptide or peptide analogue, or both is from 4 to 10 amide-bonded residues in length.

6. The compound according to claim 1, wherein the first peptide or peptide analogue, the second peptide or peptide analogue, or both is comprised of at least 4 L-amino acid residues.

7. The compound according to claim 1, wherein $Xaa_3$ is selected from among A, Q, and D.

8. The compound according to claim 1, wherein the first peptide or peptide analogue, the second peptide or peptide analogue, or both is N-alkylated with a cyclohexane substituent, and further comprises a spacer group between the substituent and the terminal amino group of the first peptide or peptide analogue, the second peptide or peptide analogue, or both, wherein the spacer is an alkyl group.

9. The compound according to claim 8, wherein the alkyl group is selected from among methylene, ethylene, propylene and butylene.

10. The compound according to claim 1, wherein the first peptide or peptide analogue, the second peptide or peptide analogue, or both is N-alkylated with an aromatic substituent, and further comprises a spacer group between the substituent and the terminal amino group of the first peptide or peptide analogue, the second peptide or peptide analogue, or both.

11. The compound according to claim 10, wherein the spacer group is selected from ethylene, propylene and butylene.

12. The compound according to claim 11, wherein the aromatic substituent is a naphthalen-2-yl moiety.

13. The compound according to claim 11, wherein the aromatic substituent is an aromatic ring substituted with one or two halogen and/or alkyl groups.

14. The compound according to claim 1, wherein the first peptide or peptide analogue, the second peptide or peptide analogue, or both is covalently bonded to a polyamine or a diamine.

15. The compound according to claim 1, wherein said compound is selected from the group consisting of:

a)

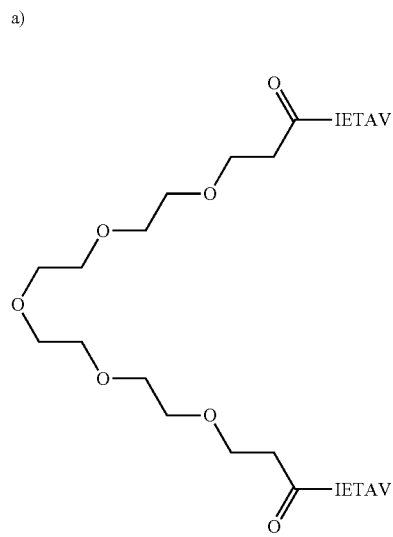
(83)

b)

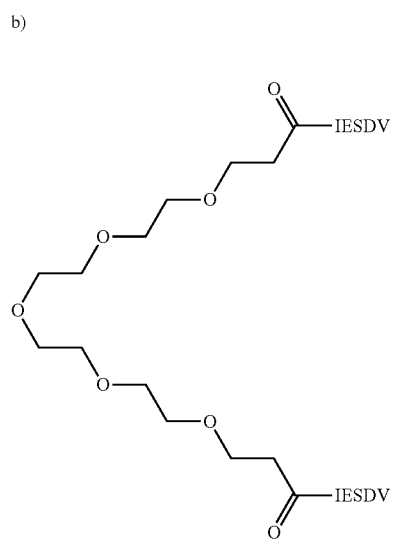
(78)

c)

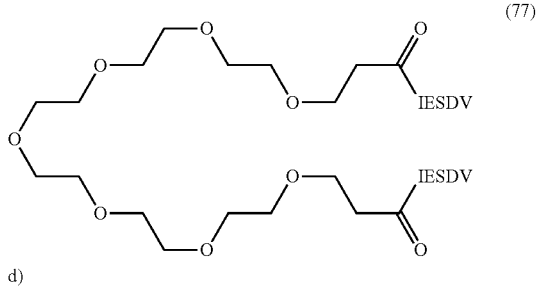
(77)

d)

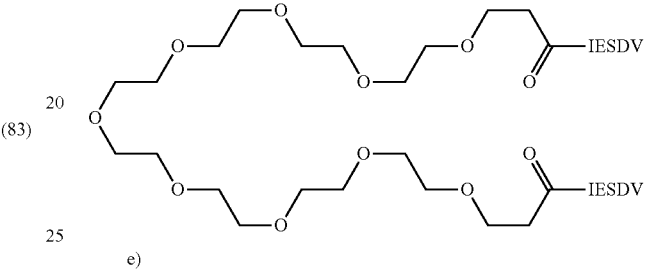
(76)

e)

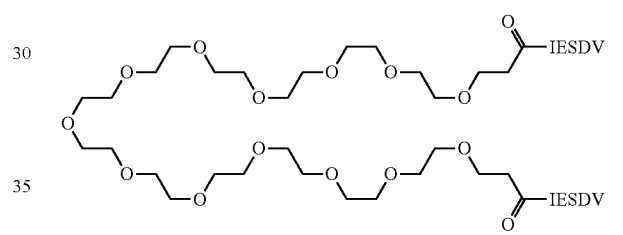
(74)

f)

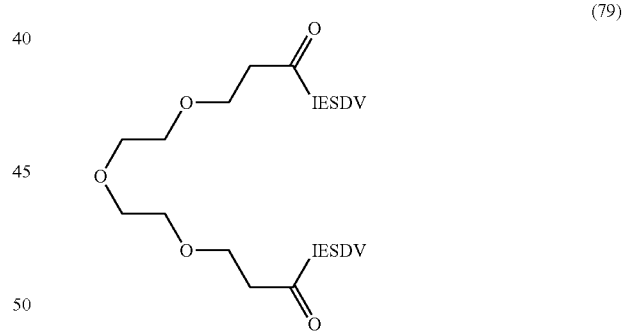
(79)

g)

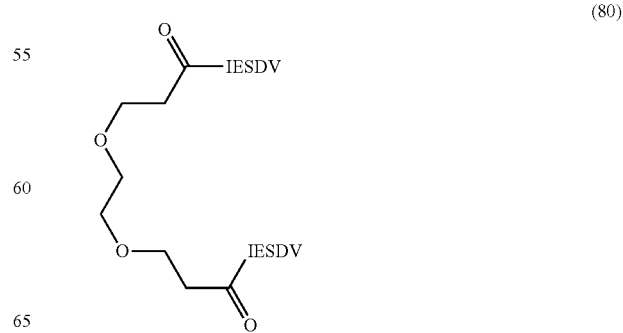
(80)

h) (88)

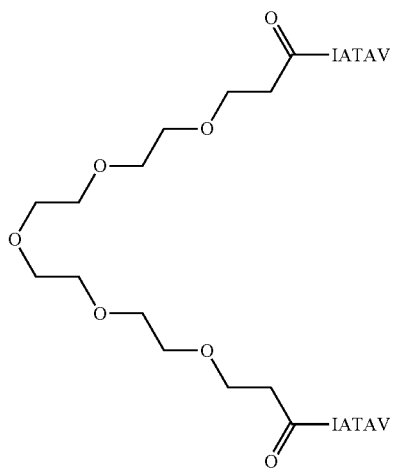

i) (90)

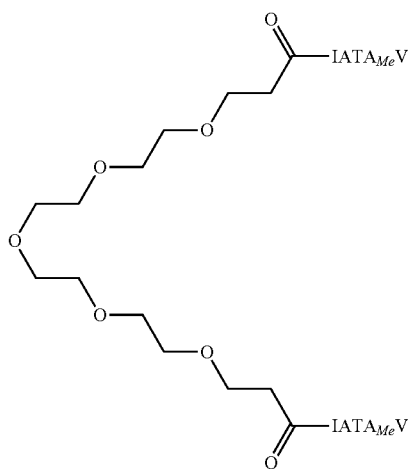

j) (75)

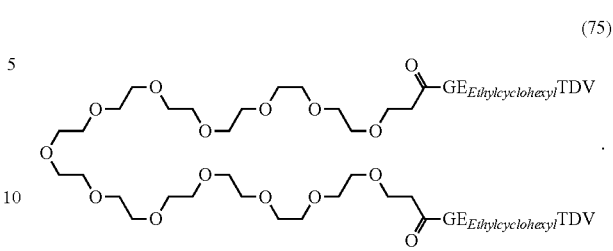

16. A method of inhibiting protein-protein interaction between a protein and a PDZ domain, comprising contacting the PDZ domain with the compound of claim 1.

17. The method according to claim 16, wherein said interaction is between an NMDAR and PSD-95 and wherein the NMDAR is comprised in a cell.

18. A method of treating or providing prophylaxis against an excitotoxic-related disease in a subject, comprising administering a compound to a subject in need thereof, wherein said compound comprises a first peptide or peptide analogue linked to a second peptide or peptide analogue by a linker, wherein said first and said second peptide or peptide analogue comprise at least four amide-bonded residues having a sequence of SEQ ID NO: 25 or SEQ ID NO: 26, wherein a. $Xaa_1$ is selected from among E, Q, and A, and
 b. $Xaa_3$ is selected from among A, Q, D, N, N-Me-A, N-Me-Q, N-Me-D, and N-Me-N.

19. The method according to claim 18, wherein the excitotoxic-related disease is selected from the group consisting of stroke, traumatic brain injury, ischemic or traumatic injury of the central nervous system (CNS), spinal cord injury, epilepsy, and neurodegenerative diseases of the CNS.

* * * * *